United States Patent
Sun et al.

(10) Patent No.: US 11,008,331 B2
(45) Date of Patent: May 18, 2021

(54) HEPATITIS B VIRUS SURFACE ANTIGEN INHIBITOR

(71) Applicant: FUJIAN COSUNTER PHARMACEUTICAL CO., LTD., Ningde (CN)

(72) Inventors: Fei Sun, Shanghai (CN); Jinhua Du, Shanghai (CN); Yanbin Hu, Shanghai (CN); Lili Zhou, Shanghai (CN); Charles Z. Ding, Shanghai (CN); Shuhhui Chen, Shanghai (CN)

(73) Assignee: FUJIAN COSUNTER PHARMACEUTICAL CO., LTD., Fujian (CN)

( * ) Notice: Subject to any disclaimer, the term of this patent is extended or adjusted under 35 U.S.C. 154(b) by 45 days.

(21) Appl. No.: 16/491,769

(22) PCT Filed: Mar. 9, 2018

(86) PCT No.: PCT/CN2018/078581
§ 371 (c)(1),
(2) Date: Sep. 6, 2019

(87) PCT Pub. No.: WO2018/161960
PCT Pub. Date: Sep. 13, 2018

(65) Prior Publication Data
US 2020/0039995 A1     Feb. 6, 2020

(30) Foreign Application Priority Data
Mar. 9, 2017   (CN) .......................... 201710138275.5

(51) Int. Cl.
*C07D 491/052*   (2006.01)
*A61P 31/20*   (2006.01)

(52) U.S. Cl.
CPC .......... *C07D 491/052* (2013.01); *A61P 31/20* (2018.01)

(58) Field of Classification Search
CPC ............................. C07D 491/052; A61P 31/20
See application file for complete search history.

(56) References Cited

U.S. PATENT DOCUMENTS

| | | |
|---|---|---|
| 2013/0251647 A1 | 9/2013 | Subkowski et al. |
| 2015/0210682 A1 | 7/2015 | Han et al. |

FOREIGN PATENT DOCUMENTS

| | | |
|---|---|---|
| CN | 103450184 A | 12/2013 |
| CN | 107759585 A | 3/2018 |
| WO | 2016128335 A1 | 8/2016 |
| WO | 2017013046 A | 1/2017 |
| WO | 2017017043 A | 9/2019 |

OTHER PUBLICATIONS

Edward J. G., et al., "The oral toll-like receptor-7 agonist GS-9620 in patients with chronic hepatitis B virus infection", Journal of Hepatology, 2015, vol. 63, p. 320-328.
Zhang Chunhong, "Application of Interferon in the Treatment of Hepatitis B", Chinese Medicine Guide, 2013, vol. 11, p. 475-476 (with English Abstract).
Eble B.E. et al., "Multiple topogenic sequences determine the transmernbrane orientation of the hepatitis B surface antigen", Mol Cell Biol, 1987, vol. 7, No. 10, p. 3591-3601.
Eble B.E. et al., "The N-terminal (pre-S2) domain of a hepatitis B virus surface glycoprotein is translocated across membranes by downstream signal sequences", Journal of Virology, 1990, vol. 64, No. 3, p. 1414-1419.
Schmitt S. et al., "Structure of pre-S2 N- and O-linked glycans in surface proteins from different genotypes of hepatitis B virus", Journal of General Virology, 2004, vol. 85, p. 2045-2053.
Huovila A. J. et al., "Hepatitis B surface antigen assembles in a post-ER, pre-Golgi compartment", The Journal of Cell Biology, 1992, vol. 118, No. 6, p. 1305-1320.
Chisari F.V. et al., "Expression of hepatitis B virus large envelope polypeptide inhibits hepatitis B surface antigen secretion in transgenic mice", Journal of Virology, 1986, vol. 60, No. 3, p. 880-887.
Bruss V., "A short linear sequence in the pre-S domain of the large hepatitis B virus envelope protein required for virion formation", Journal of Virology, 1997, vol. 71, No. 12, p. 9350-9357.
Bruss V., "Envelopment of the hepatitis B virus nucleocapsid", Virus Research, 2004, vol. 106, p. 199-209.
Lunsdorf H et al., "Virus-like particle production with yeast: ultrastructural and immunocytochemical insight into Pichia pastoris producing high levels of the Hepatitis B surface antigen", Microbial Cell Factories, 2011,vol. 10, No. 48, p. 1-10.
Bruns M. et al., "Enhancement of hepatitis B virus infection by noninfectious subviral particles", Journal of Virology, 1998, vol. 72, No. 2, p. 1462-1468.
D. Ganem et al.,"Hepatitis B virus infection—natural history and clinical consequences", The New England Journal of Medicine, 2004, vol. 350, p. 118-1129

(Continued)

*Primary Examiner* — Marcos L Sznaidman
(74) *Attorney, Agent, or Firm* — Houston Beshining Law Office PLLC; Liangang Ye

(57) ABSTRACT

10-oxo-6,1-dihydrobenzo[e]pyrido[1,2-c][1,3]oxazine-9-carboxylic acid derivatives of formula (I) as hepatitis B surface antigen inhibitors or pharmaceutically acceptable salts thereof, and uses of a compound of formula (I) or pharmaceutically acceptable salts thereof and pharmaceutical compositions thereof in preparation of medicaments for treatment of viral hepatitis B.

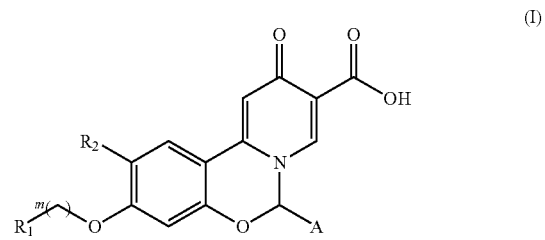

23 Claims, No Drawings
Specification includes a Sequence Listing.

(56) References Cited

OTHER PUBLICATIONS

Vanlandschoot P. et al., "Hepatitis B virus surface antigen suppresses the activation of monocytes through interaction with a serum protein and a rnonocyte-specific receptor", Journal of General Virology, 2002, vol. 83, p. 1281-1289.

Op den Brouw M.L. et al., "Hepatitis B virus surface antigen impairs myeloid dendritic cell function: a possible immune escape mechanism of hepatitis B virus", Immunology, vol. 126, p. 280-289.

Chisari F.V. et al., "Molecular pathogenesis of hepatocelluar carcinoma in hepatitis B virus transgenic mice", Cell, 1989, vol. 59, p. 1145-1156.

Wang et al,, "Characterization of HBV integrants in 14 hepatocellular carcinomas: association of truncated X gene and hepatocellular carcinogenesis", Oncogene, 2004, vol. 23, p. 142-148.

Chen Chien-Jen et al., "Hepatitis B virus DNA levels and outcomes in chronic hepatitis B", Hepatology, Suppl. 2009, vol. 49, No. 5, S72-S84.

Xie Kun-Lin et al., "MicroRNAs associated with HBV infection and HBV-related HCC", Theranostics, 2014, vol. 4, Issue 12, p. 1176-1192.

Janssen H.L A et al., "Pegylated interferon alfa-2b alone or in combination with lamivudine for HBeAg-positive chronic hepatitis B: a randomised trial", Lancet, 2005, vol. 365, p. 123-129.

Marcellin P. et al., "Peginterferon alfa-2a alone, lamivudine alone, and the two in combination in patients with HBeAg-negative chronic hepatitis B", The New England Journal of Medicine, 2004, vol. 351, p. 1206-1217.

Buster E.H.C.J. et al., "Peginterferon aifa-2b is safe arid effective in HBeAg-positive chronic hepatitis B patients with advanced fibrosis", Hepatology, 2007, vol. 46, No. 2, p. 388-394.

Berge et al., "Pharmaceutical salts", Journai of Pharmaceutical Sciences, 1977, vol. 66, No. 1, p. 1-19.

International Search Report and Written Opinion of PCT/CN2018/078581 dated Jun. 6, 2018.

First Office Action and Search Report issued in the counterpart Chinese application No. 201880001647.2 dated May 8, 2019.

Jul. 2, 2020 Office Action issued in counterpart Canadian application No. 3,055,442.

Jul. 31, 2020 Office Action issued in counterpart Eurasia application No. 201992082.

Examination Report and Search Report issued in the counterpart Malaysian application No. PI2019005107 dated Feb. 26, 2020.

Notification of Reasons for Refusal issued in the counterpart Japanese application No. 2019-548977 dated Feb. 12, 2020.

HEPATITIS B VIRUS SURFACE ANTIGEN INHIBITOR

CROSS REFERENCE TO RELATED APPLICATION

The present application claims priority to the Chinese Patent Application No. CN201710138275.5 filed on Mar. 9, 2017, the contents of which are incorporated herein by reference in their entireties.

REFERENCE TO AN ELECTRONIC SEQUENCE LISTING

The contents of the electronic sequence listing (P1941200US-16491769-2-SEQ.txt; Size: 999 bytes; and Date of Creation: Mar. 12, 2020) is herein incorporated by reference in its entirety.

FIELD OF INVENTION

The present disclosure relates to a novel 10-oxo-6,10-dihydrobenzo[e]pyrido[1,2-c][1,3]oxazine-9-carboxylic acid derivative serving as a hepatitis B virus surface antigen inhibitor, specifically relates to a compound represented by formula (I) or a pharmaceutically acceptable salt thereof, and a use of the compound represented by formula (I) or the pharmaceutically acceptable salt thereof and a pharmaceutical composition thereof in the treatment of viral hepatitis B.

PRIOR ARTS

Viral hepatitis B, abbreviated as hepatitis B, is a disease caused by Hepatitis B Virus (HBV) infection in the body. Hepatitis B virus is a hepadnaviridae that mainly exists in hepatocytes and damages hepatocytes, causing inflammation, necrosis and fibrosis of hepatocytes. Viral hepatitis B is divided into two types, acute hepatitis B and chronic hepatitis B. Most adults with acute hepatitis B can heal themselves through their inherent immune function. However, chronic hepatitis B (CHB) has become a major challenge for global health care, and a major cause of chronic liver disease, cirrhosis and hepatocellular carcinoma (HCC) (Edward J. G., et al., The oral toll-like receptor-7 agonist GS-9620 in patients with chronic hepatitis B virus infection. Journal of Hepatology (2015); 63: 320-328). It is estimated that 2 billion people worldwide are infected with chronic hepatitis B virus, and more than 350 million people have progressed to hepatitis B. Nearly 600,000 people die each year from the complications of chronic hepatitis B (Edward J. G., et al., The oral toll-like receptor 7 agonist GS-9620 in patients with chronic hepatitis B virus infection. Journal of Hepatology (2015)). China is a high-prevalence area of hepatitis B, and accumulated a lots of patients with hepatitis B, which is a serious hazard. According to the data, there are about 93 million people infected with hepatitis B virus in China, and about 20 million of them are diagnosed with chronic hepatitis B, among them, 10%-20% can progress to cirrhosis, and 1%-5% can progress to HCC. (Zhang Chunhong, Application of Interferon in the Treatment of Hepatitis B. Chinese Medicine Guide (2013); 11: 475-476.)

The key to functional cure for hepatitis B is to clear HBsAg (hepatitis B virus surface antigen) and produce surface antibodies. Quantification of HBsAg is a very important biological indicator. In chronically infected patients, a decrease in HBsAg and seroconversion are rarely observed, which is the end point of current treatment.

The surface antigen protein of hepatitis B virus (HBV) plays a very important role in the process of HBV invasion into liver cells, and is of great significance for the prevention and treatment of HBV infection. Surface antigen proteins include large (L), medium (M) and small (S) surface antigen proteins that share a common C-terminal S region. They are expressed in an open reading frame, the different lengths of which are determined by the three AUG start codons of the reading frame. These three surface antigen proteins include pre-S1/pre-S2/S, pre-S2/S and S domains. The HBV surface antigen protein is integrated into the endoplasmic reticulum (ER) membrane and initiated by the N-terminal signal sequence (Eble et al., 1987, 1990; Schmitt et al., 2004). They not only constitute the basic structure of virions, but also form globular and filamentous subviral particles (SVPs, HBsAg), aggregated in ER, host ER and pre-Golgi apparatus (Huovila et al., 1992), SVP contains mostly S Surface antigen protein (Chisari et al., 1986). The L protein (Bruss, 1997, 2004) is critical in the aspects of morphogenesis of the virus and the interaction of the nucleocapsid, but is not necessary for the formation of SVP. (Lunsdorf et al., 2011). Because of their lack of nucleocapsids, the SVPs are non-infectious. SVPs are heavily involved in disease progression, especially in immune response to hepatitis B virus, in the blood of infected people, the content of SVPs is at least 10, 000 times the number of viruses (Bruns et al., 1998; Ganem and Prince, 2004), and it traps the immune system and weakens the body's immune response to hepatitis B virus. HBsAg also inhibits human innate immunity, inhibits the production of cytokines induced by polysaccharides (LPS) and IL-2 (Vanlandschoot et al., 2002), inhibits DC function of dendritic cells, and inhibits the induced activity of LPS against the interference kinase -1/2 in ERK-1/2 and c-Jun N-terminal in monocytes (Op den Brouw et al., 2009). It is worth noting that disease progression of cirrhosis and hepatocellular carcinoma is also largely associated with persistent secretion of HBsAg (Chisari et al., 1989; Wang et al., 2004; Yang et al., 2009; Wu et al., 2014). These researches suggest that HBsAg plays an important role in the progress of chronic hepatitis.

The currently approved anti-HBV drugs are mainly immunomodulators (interferon-$\alpha$ and pegylated interferon-$\alpha$-2$\alpha$) and antiviral therapeutic drugs (Lamivudine, Adefovir Dipivoxil, Entecavir, Telbivudine, Tenofovir, Clevudine, etc.). Among them, antiviral therapeutic drugs belong to nucleotides, and their mechanism of action is to inhibit the synthesis of HBV DNA, instead of directly reducing HBsAg levels. Like prolonged treatment, nucleotides drugs has shown HBsAg clearance rate which is similar to natural observations (Janssen et al. Lancet (2005), 365, 123-129; Marcellin et al. N. Engl. J. Med. (2004), 351, 1206-1217; Buster et al. Hepatology (2007), 46, 388-394).

Clinically available therapies exhibit a poor efficacy in reducing HBsAg, therefore, the development of small molecule oral inhibitors that can effectively reduce HBsAg is currently required for clinical use.

Even though WO2016128335A1 has disclosed a series of 2-oxo-6,7-dihydrobenzo[a]quinazine-3-carboxylic acid derivatives for the treatment or prevention of hepatitis B virus infection (the general structure is shown as follows), this series of fused ring compounds still have the problems of strong molecular rigidity, insufficient solubility, and easy aromatization. Therefore, for clinical applications, the demand for drugs with better druggability still exists.

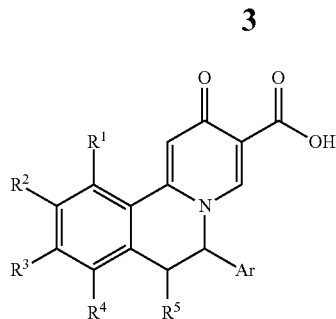

Content of the Present Invention

The present disclosure provides a compound represented by formula (I) or a pharmaceutically acceptable salt thereof,

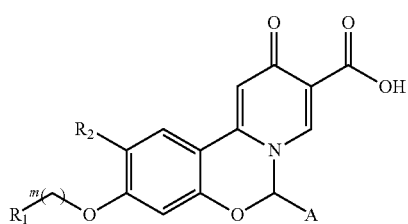

(I)

wherein, $R_1$ is selected from H, OH, CN, $NH_2$, or selected from the group consisting of $C_{1-5}$ alkyl, $C_{1-5}$ heteroalkyl, $C_{2-5}$ alkynyl, $C_{3-6}$ alkyl and 3-6 membered heterocycloalkyl, each of which is optionally substituted by 1, 2 or 3 R;

$R_2$ is selected from H, halogen, or selected from the group consisting of $C_{1-3}$ alkyl and $C_{1-3}$ heteroalkyl, each of which is optionally substituted by 1, 2 or 3 R;

m is selected from the group consisting of 0, 1, 2, 3, 4 and 5;

A is selected from the group consisting of phenyl and 5-6 membered heteroaryl, each of which is optionally substituted by 1, 2 or 3 R;

R is selected from the group consisting of H, halogen, OH, CN, $NH_2$, =O, $CH_3$, $CH_3CH_2$, $CH_3O$, $CF_3$, $CHF_2$ and $CH_2F$;

the "hetero" in the $C_{1-5}$ heteroalkyl, 3-6 membered heterocycloalkyl, $C_{1-3}$ heteroalkyl, 5-6 membered heteroaryl is independently selected from the group consisting of N, —O—, =O, —S—, —NH—, —(C=O)—, —(S=O)— and —(S=O)$_2$—;

In any one of the cases above, the number of the heteroatom or the heteroatom group is independently selected from 1, 2 or 3.

In some embodiments of the present disclosure, R is selected from the group consisting of H, F, Cl, Br, OH, $CH_3$, $CH_3O$, $CF_3$, $CHF_2$ and $CH_2F$.

In some embodiments of the present disclosure, $R_1$ is selected from H, OH, CN, $NH_2$, or selected from the group consisting of $CH_3$, $CH_3CH_2$, $CH_3CH_2CH_2$, $CH_3CH_2CH_2CH_2$, $CH_3O$, $CH_3CH_2O$, $CH_3S$, $CH_3S(=O)$, $CH_3S(=O)_2$, $CH_3SCH_2$, $CH_3CH_2S$, $CH_3NH$,

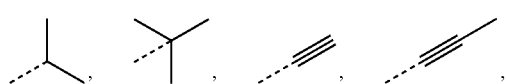

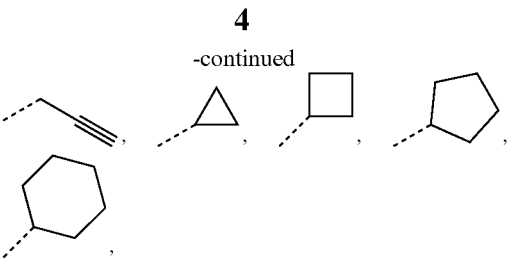

pyrrolidinyl, piperidyl, tetrahydropyranyl, morpholinyl, 2-pyrrolidonyl and 3-pyrrolidonyl, each of which is optionally substituted by 1, 2 or 3 R.

In some embodiments of the present disclosure, $R_1$ is selected from H, OH, CN, $NH_2$, or selected from the group consisting of $CH_3$, $CH_3CH_2$, $CH_3CH_2CH_2$, $CH_3CH_2CH_2CH_2$, $CH_3O$, $CH_3CH_2O$, $CH_3S$, $CH_3S(=O)$, $CH_3S(=O)_2$, $CH_3SCH_2$, $CH_3CH_2S$, $CH_3NH$,

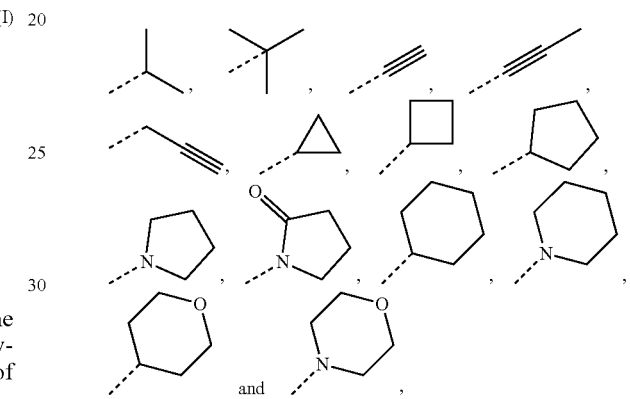

each of which is optionally substituted by 1, 2 or 3 R.

In some embodiments of the present disclosure, $R_1$ is selected from the group consisting of H, OH, $CH_3$, $CHF_2$, $CH_3O$,

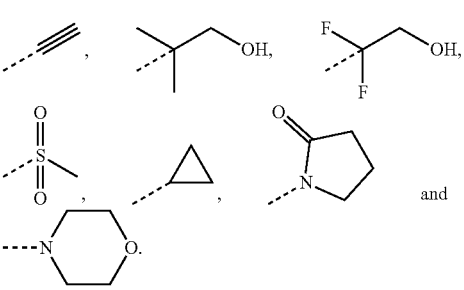

In some embodiments of the present disclosure, $R_2$ is selected from H, F, Cl, Br, or selected from the group consisting of $CH_3$, $CH_3CH_2$, $CH_3O$, $CH_3CH_2O$ and

each of which is optionally substituted by 1, 2 or 3 R.

In some embodiments of the present disclosure, $R_2$ is selected from the group consisting of Cl and $CH_3O$.

In some embodiments of the present disclosure, A is selected from the group consisting of phenyl, thienyl, thiazolyl, isothiazolyl, oxazolyl and isoxazolyl, each of which is optionally substituted by 1, 2 or 3 R.

In some embodiments of the present disclosure, A is selected from the group consisting of

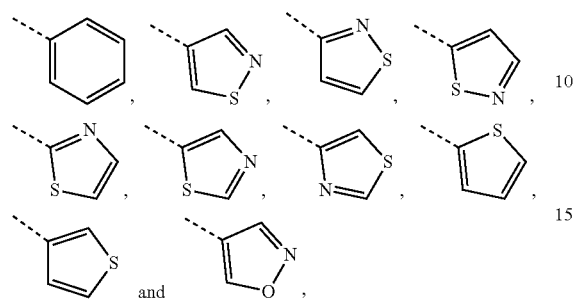

each of which is optionally substituted by 1, 2 or 3 R.

In some embodiments of the present disclosure, A is selected from the group consisting

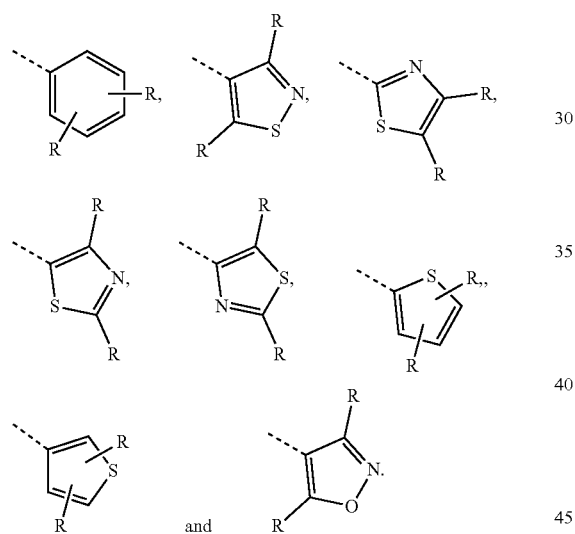

In some embodiments of the present disclosure, A is selected from the group consisting of

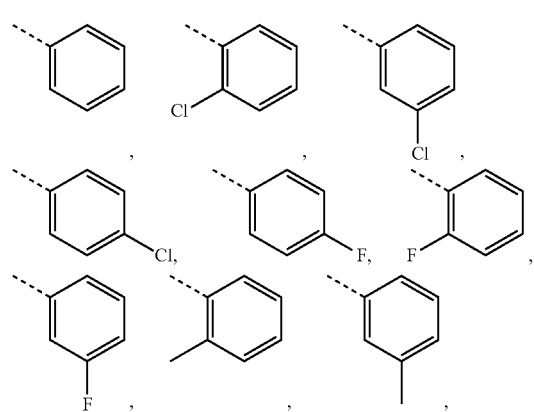

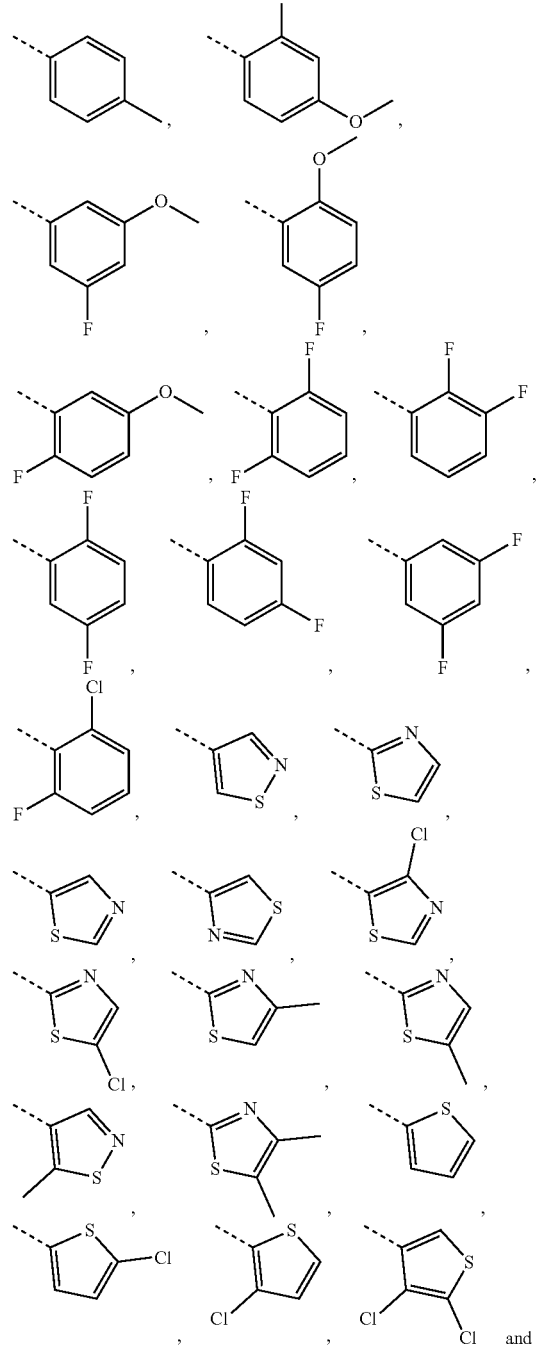

In some embodiments of the present disclosure, m is 3.
In some embodiments of the present disclosure, $R_2$ is selected from the group consisting of Cl and $CH_3O$.
In some embodiments of the present disclosure, $R_1$ is $CH_3O$.
In some embodiments of the present disclosure, m is 1.
In some embodiments of the present disclosure, $R_2$ is Cl.
In some embodiments of the present disclosure, $R_1$ is

In some embodiments of the present disclosure, A is selected from the group consisting of

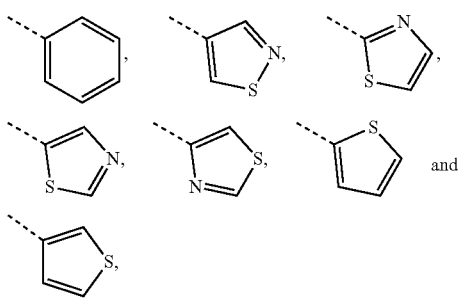

and each of which is optionally substituted by 1, 2 or 3 R.

In some embodiments of the present disclosure, the compound or the pharmaceutically acceptable salt thereof, is selected from the group consisting of

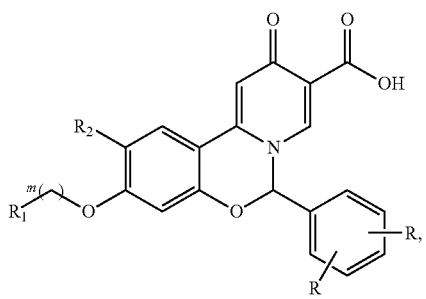

(II)

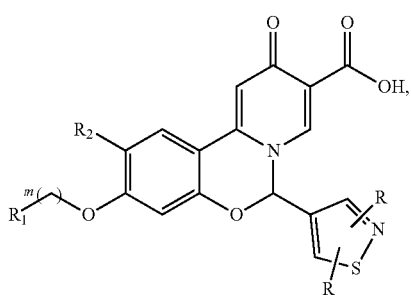

(III)

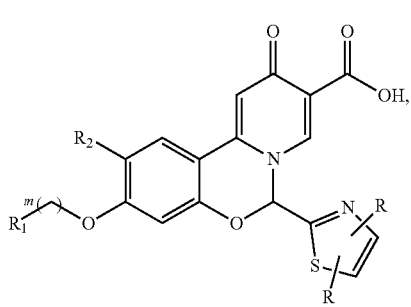

(IV)

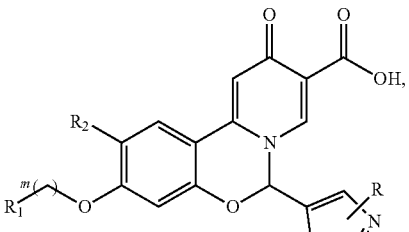

(V)

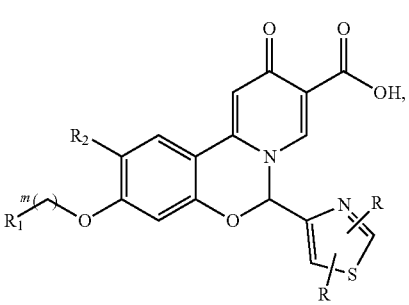

(VI)

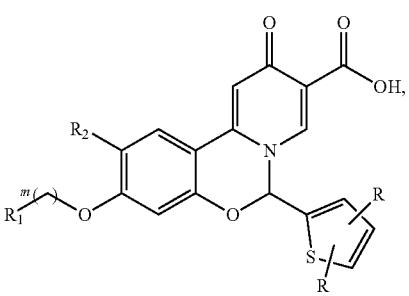

(VII)

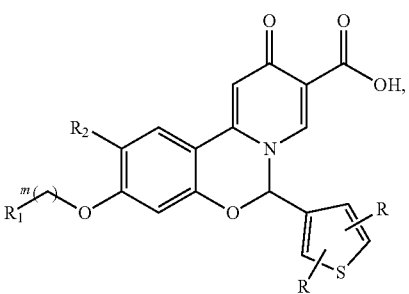

(VIII) and

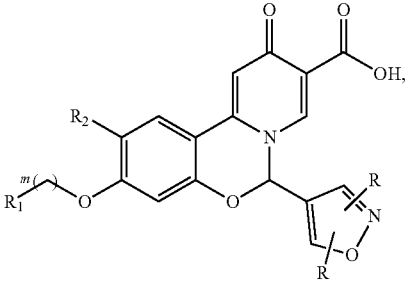

(IX)

wherein, $R_1$, $R_2$, A, R and m are as defined above.

In some embodiments of the present disclosure, the compound or the pharmaceutically acceptable salt thereof, is selected from the group consisting of

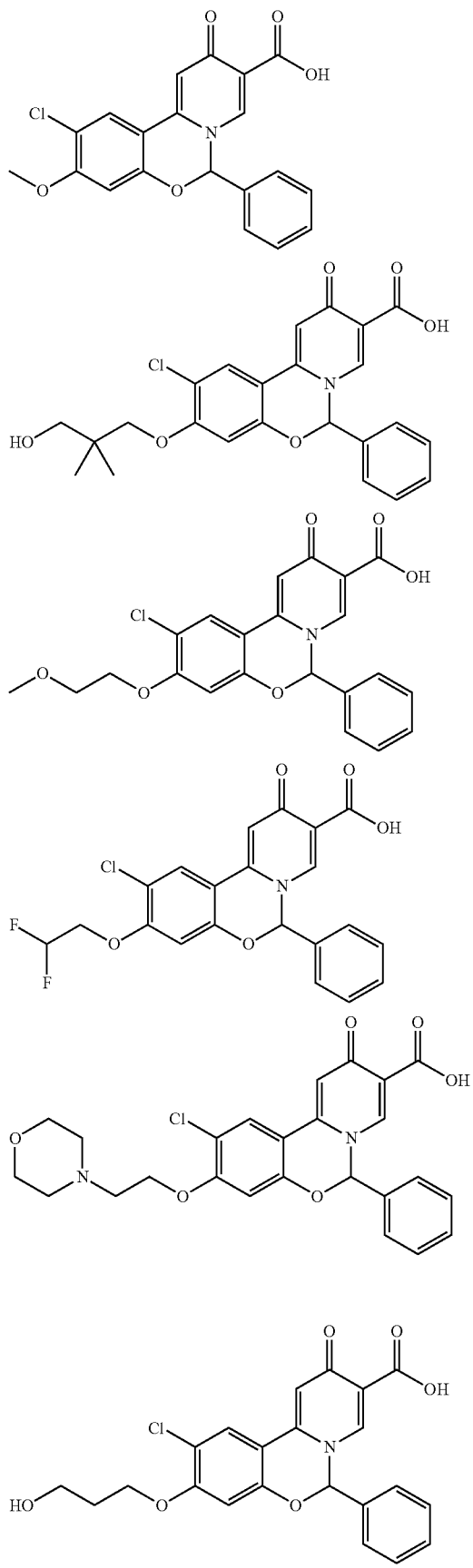
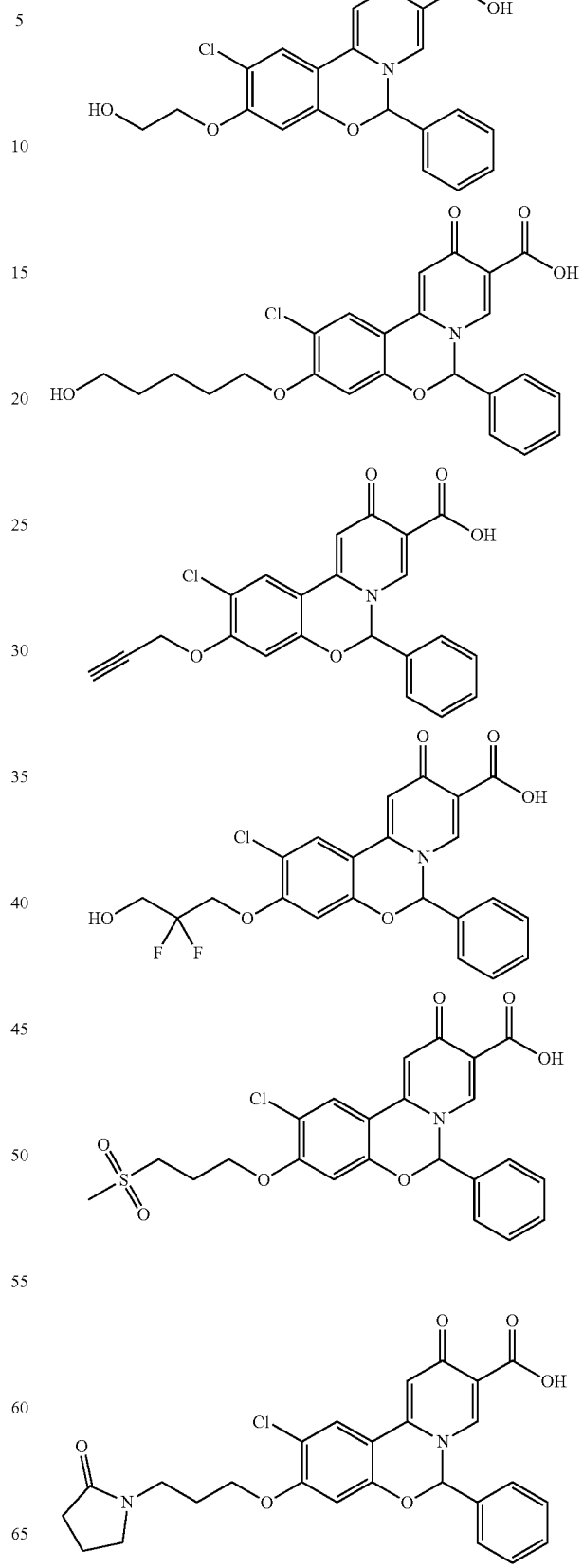

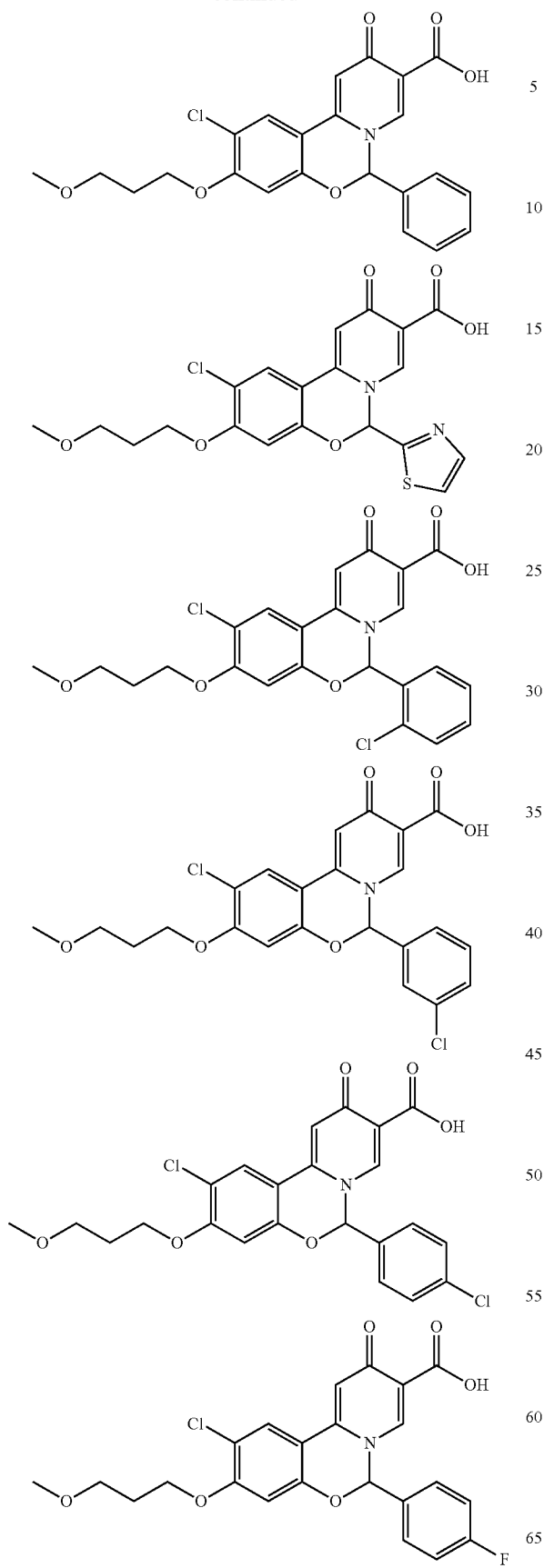
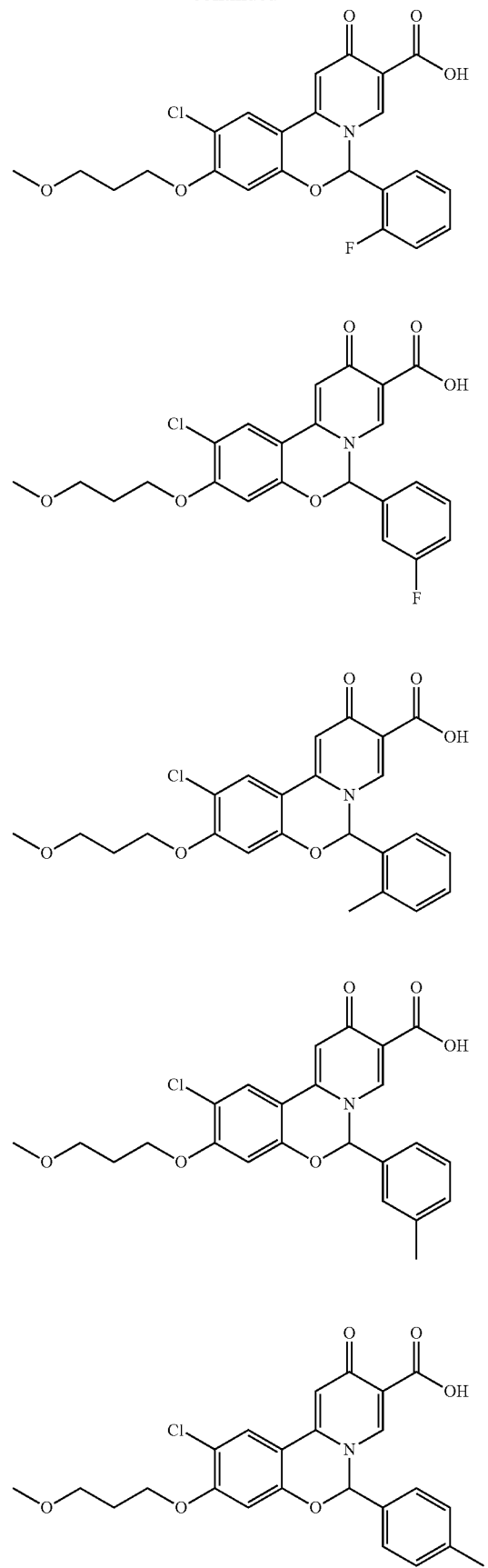

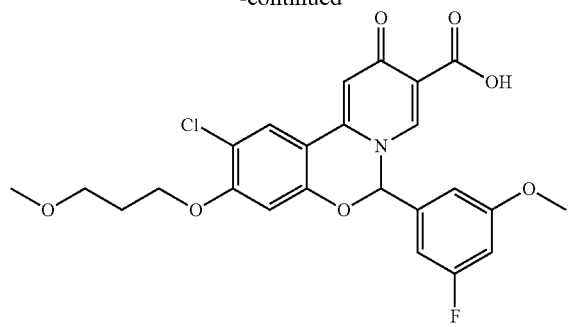
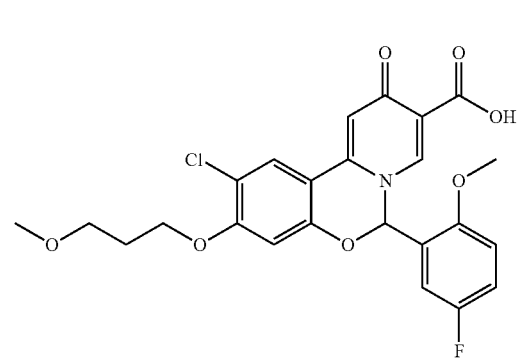
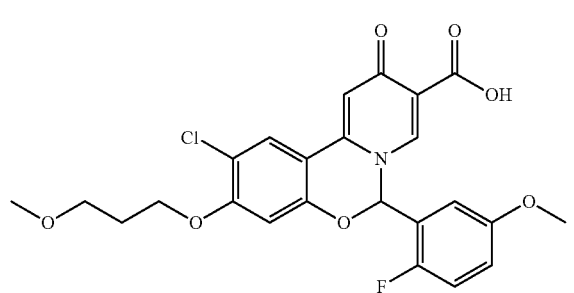
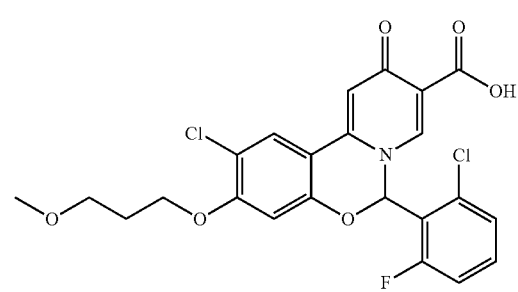
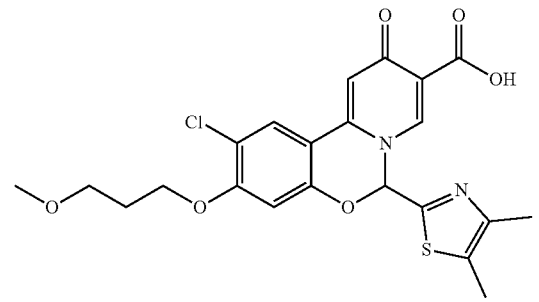
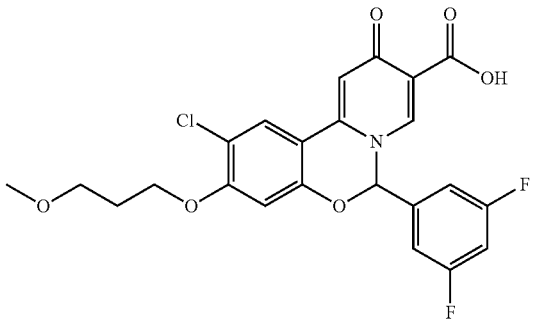
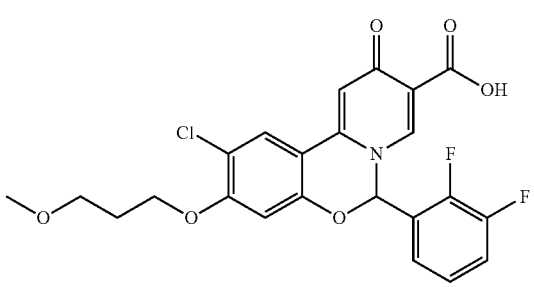
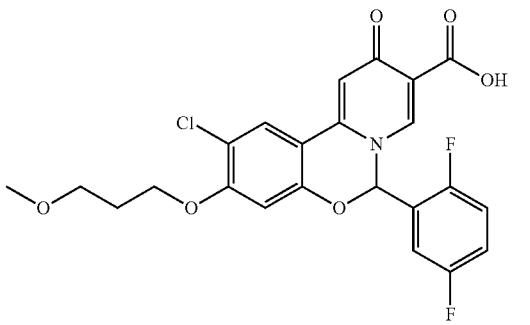
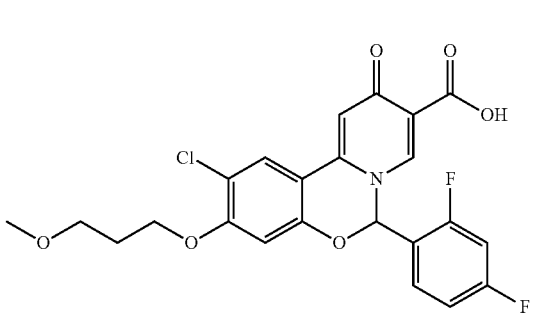
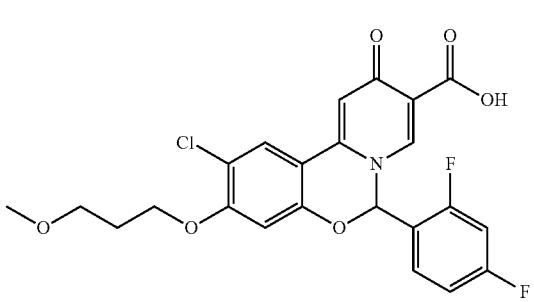

15
-continued
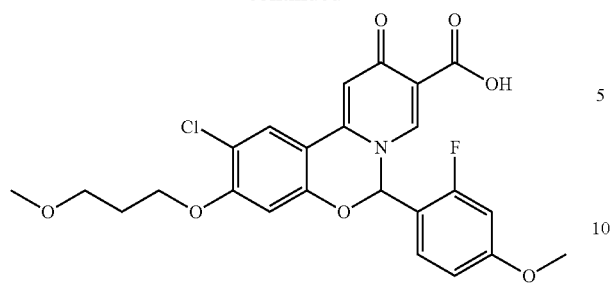
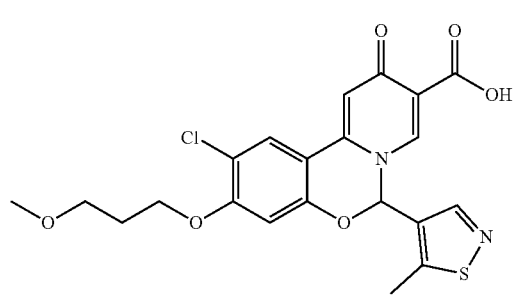
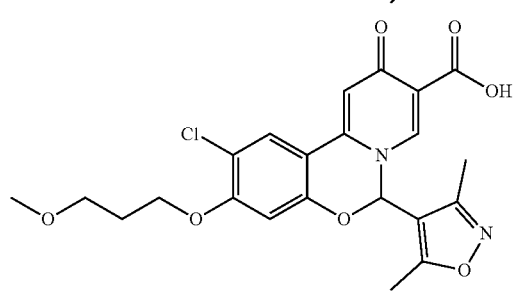
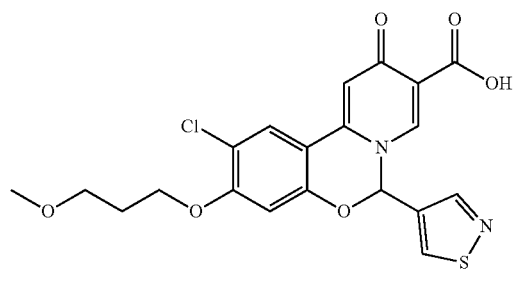
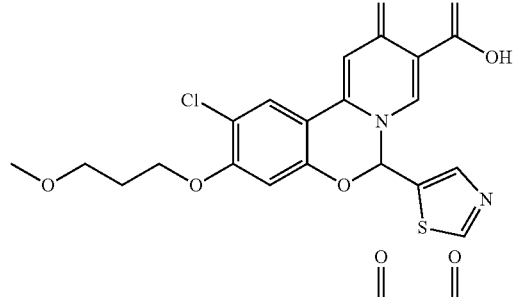
16
-continued
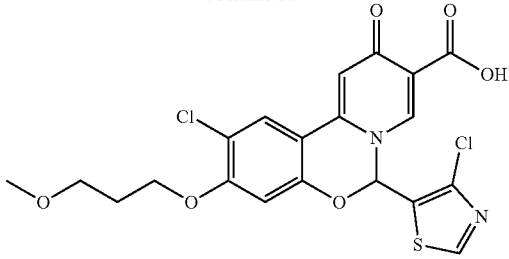
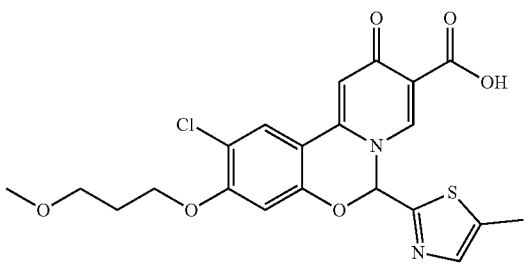
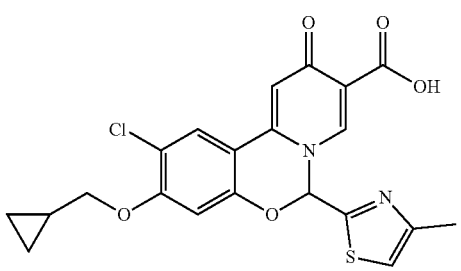
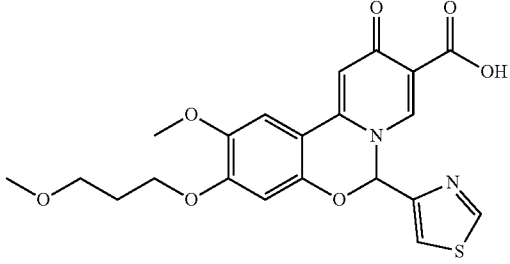
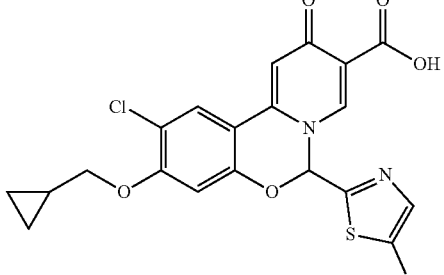
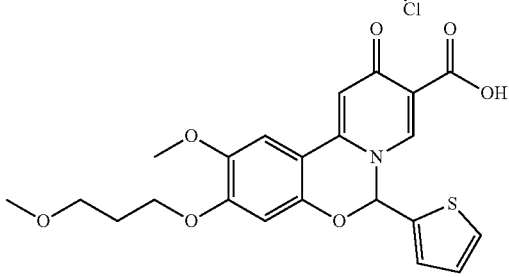

17
-continued
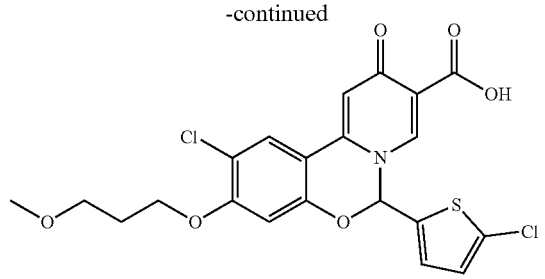
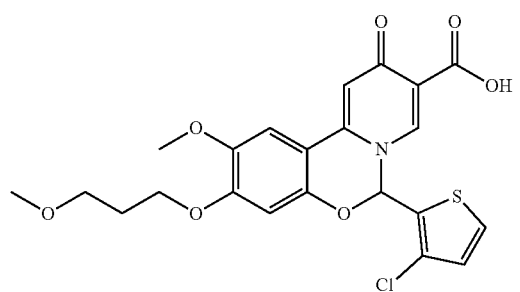
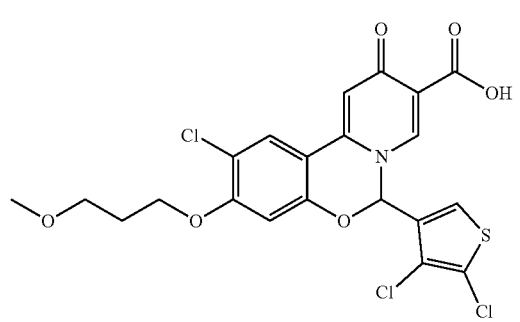
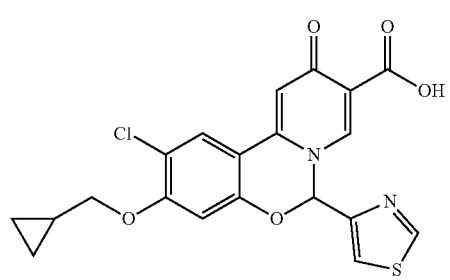
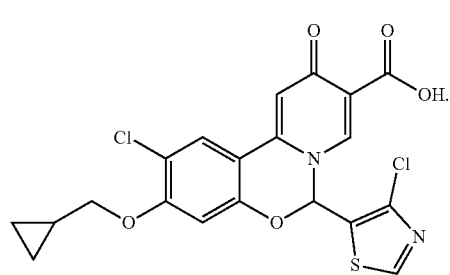
and
18
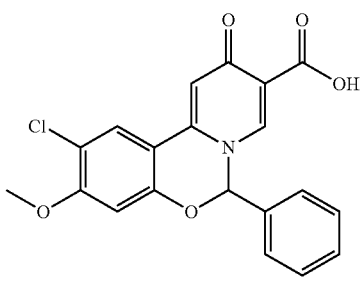
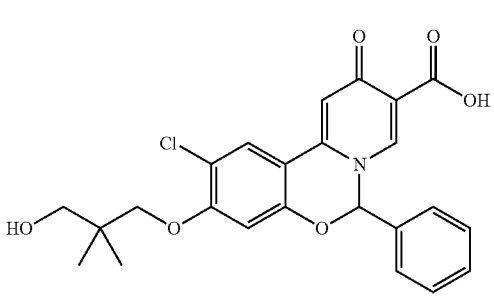
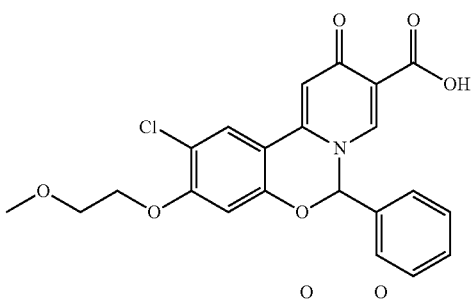
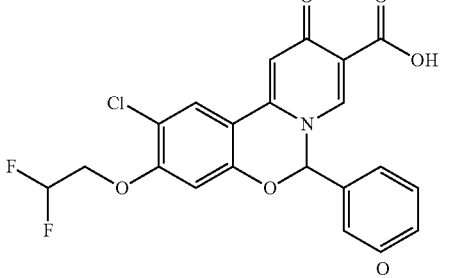
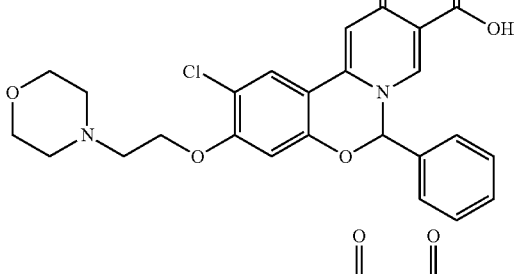
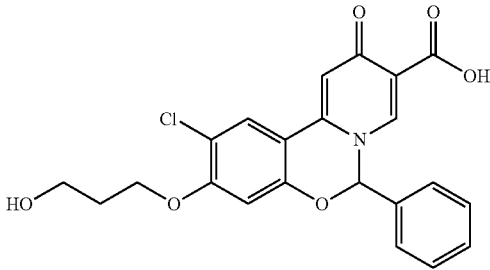
The present disclosure also provides the compound or the pharmaceutically acceptable salt thereof, which is selected from the group consisting of

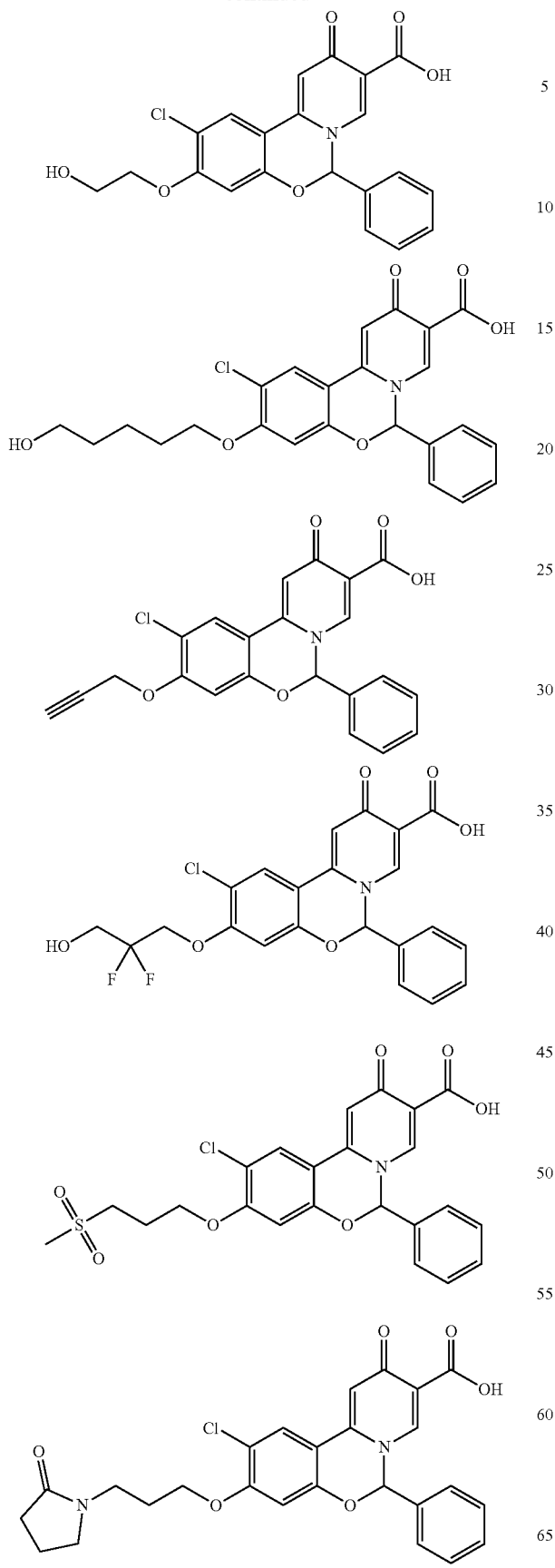
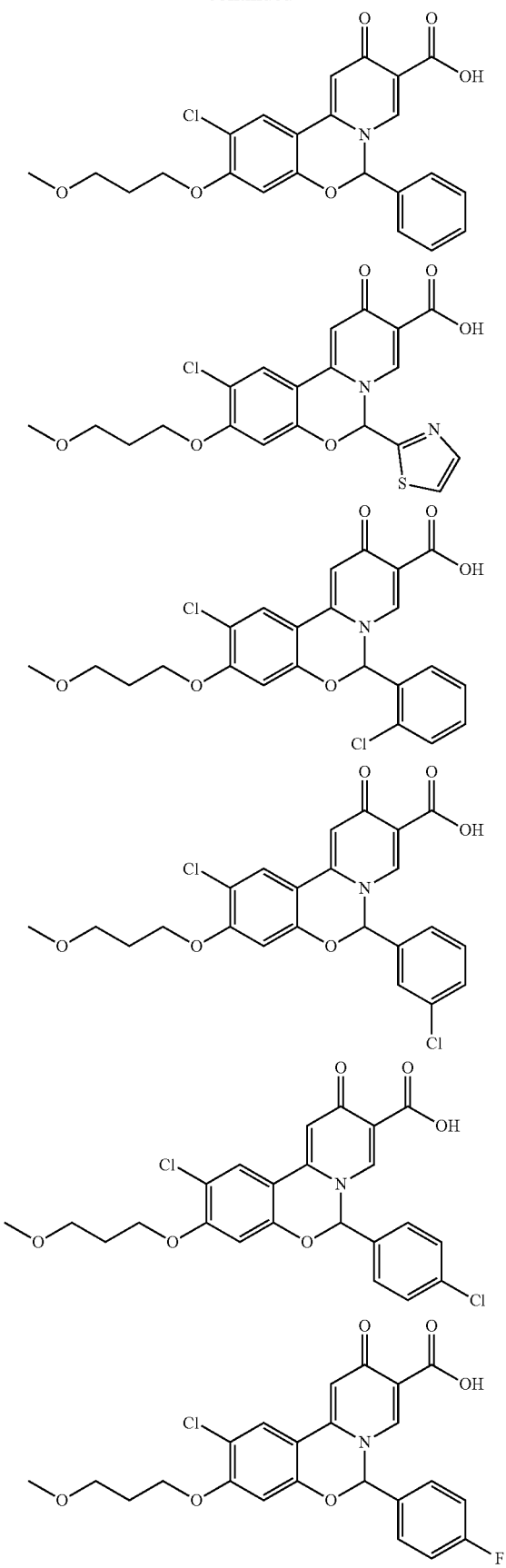

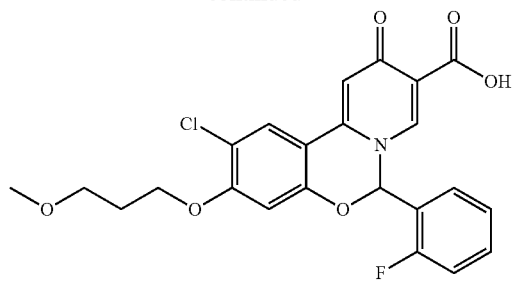
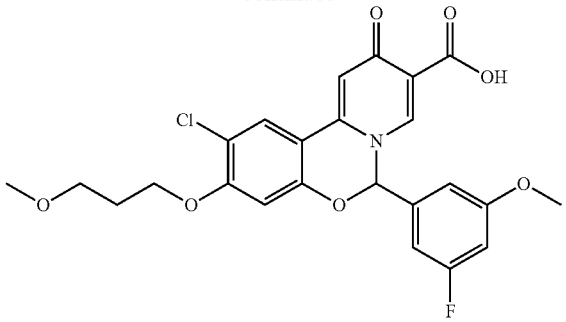
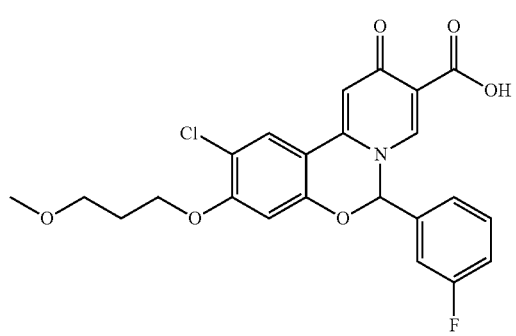
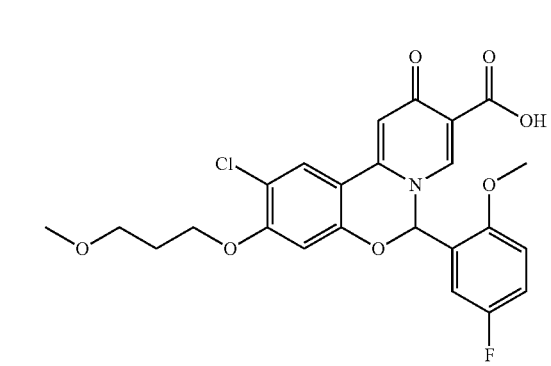
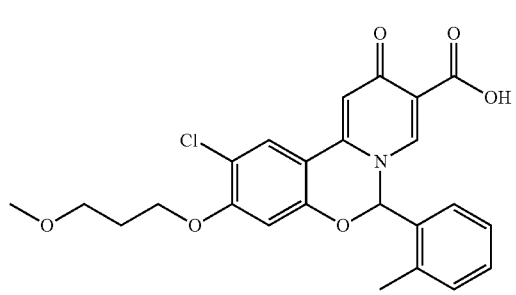
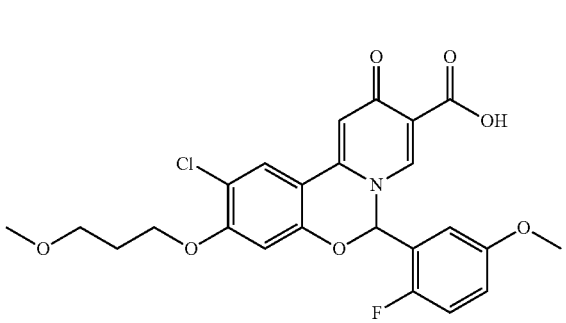
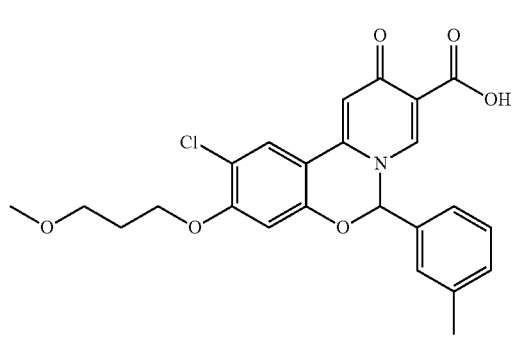
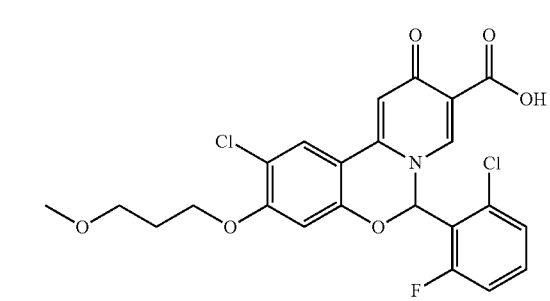
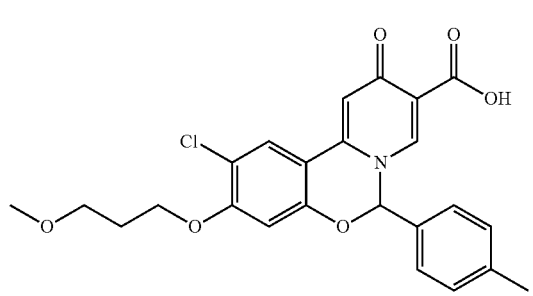
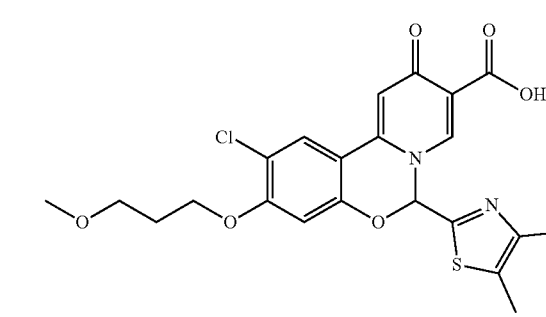

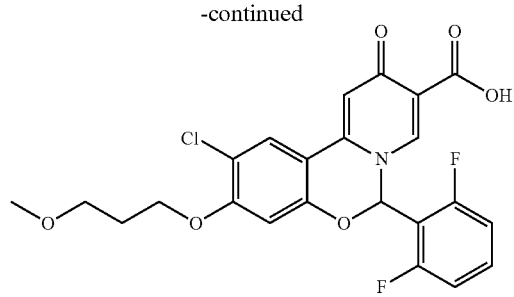
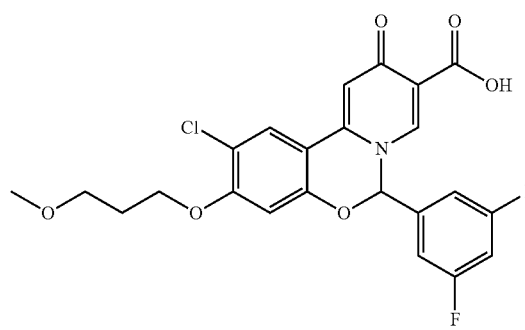
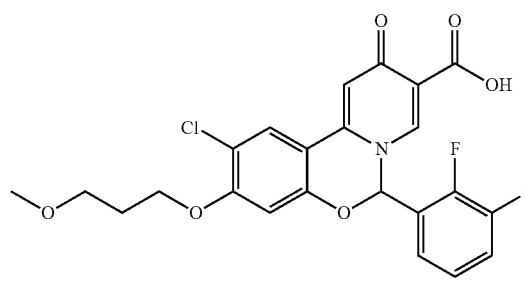
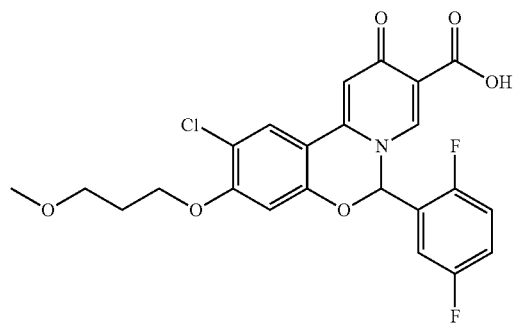
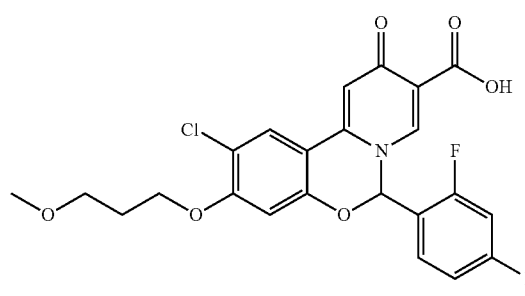
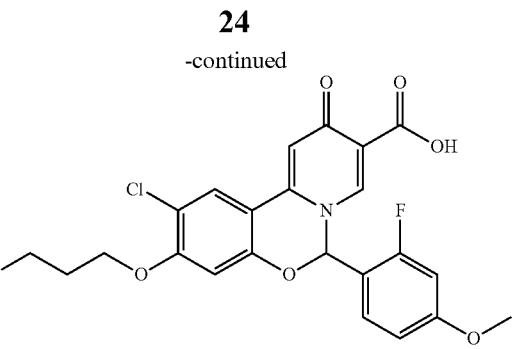
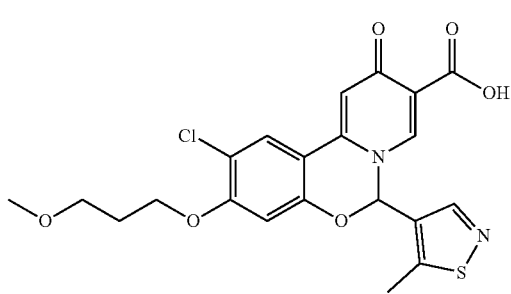
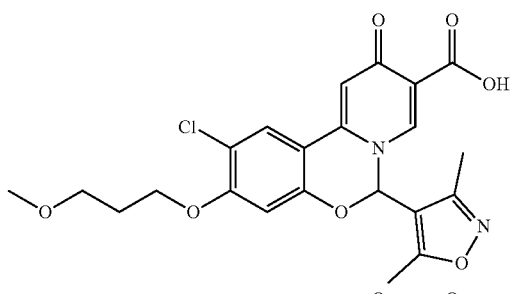
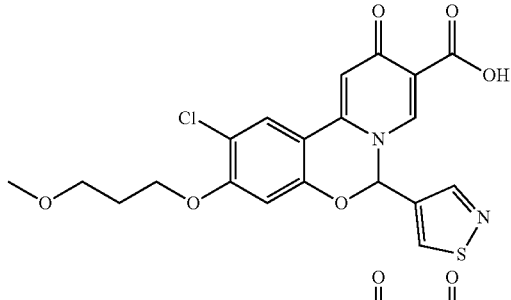
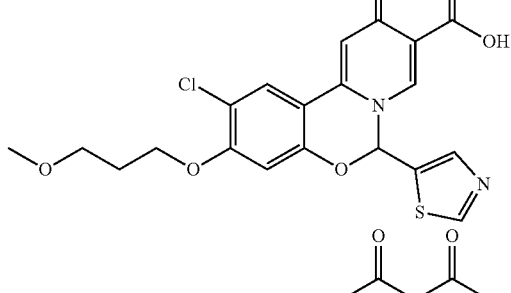
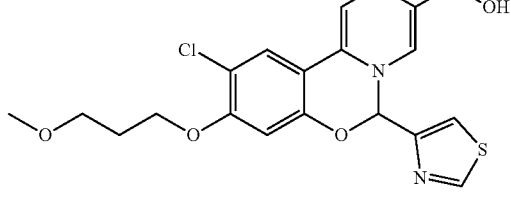

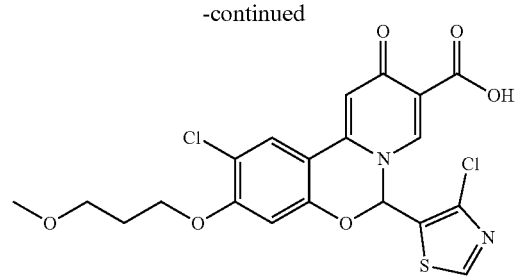
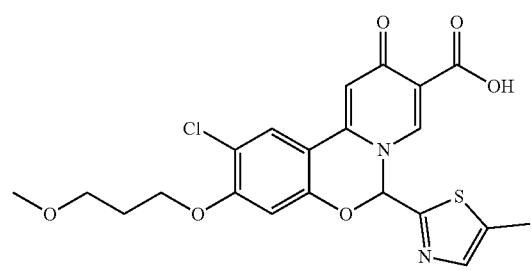
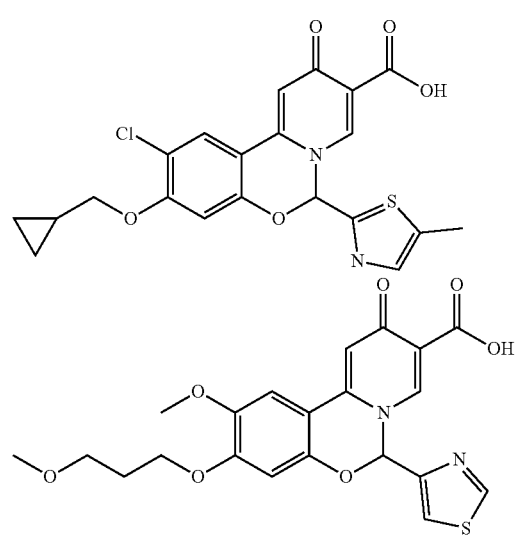
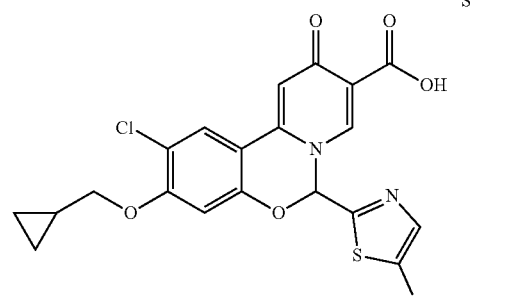
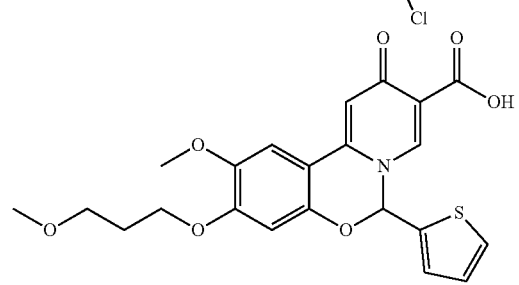
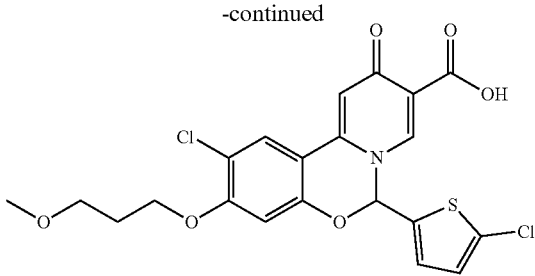
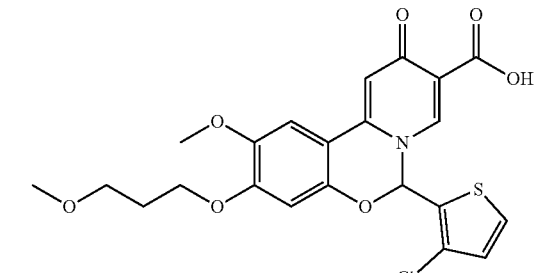
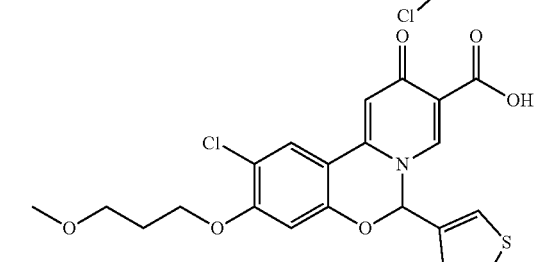
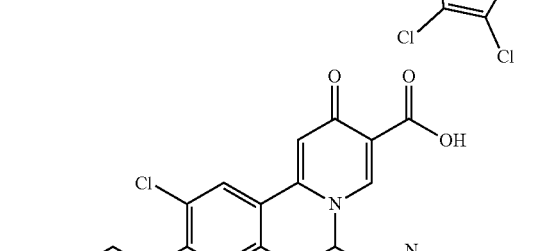
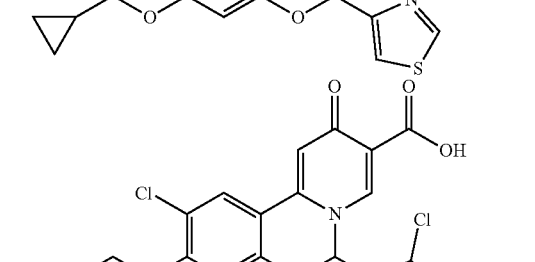
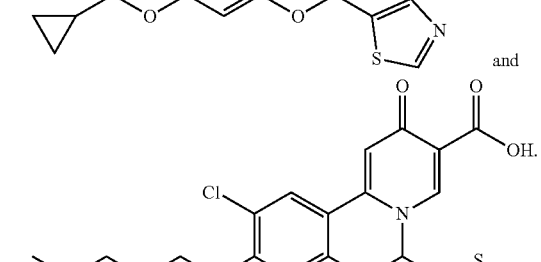
and
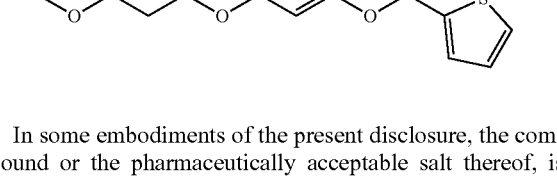
In some embodiments of the present disclosure, the compound or the pharmaceutically acceptable salt thereof, is selected from the group consisting of

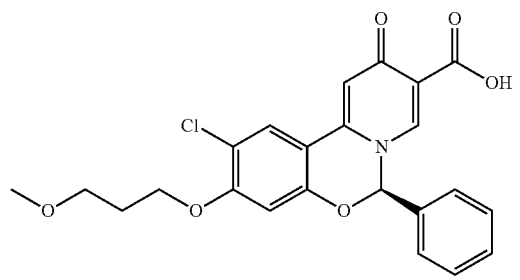
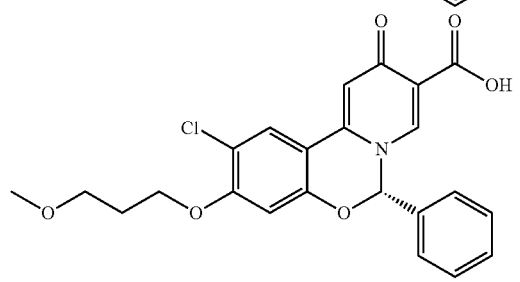
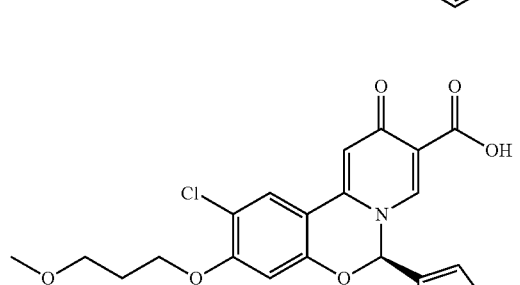
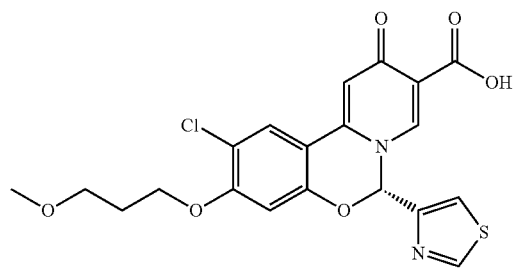
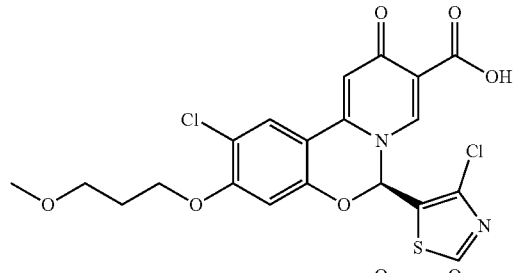
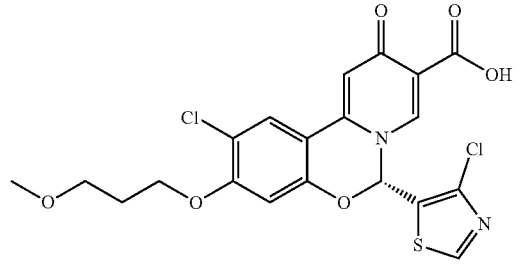
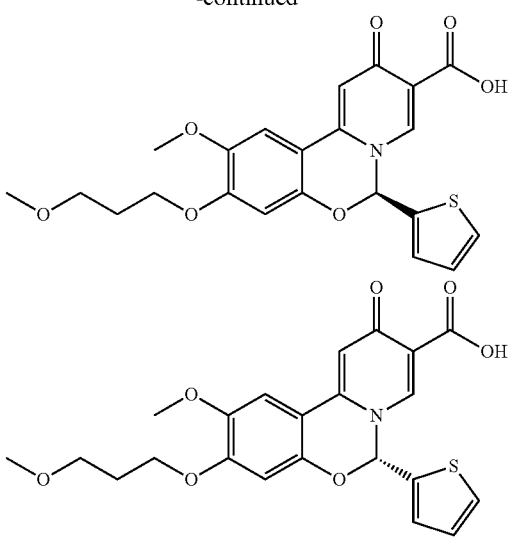
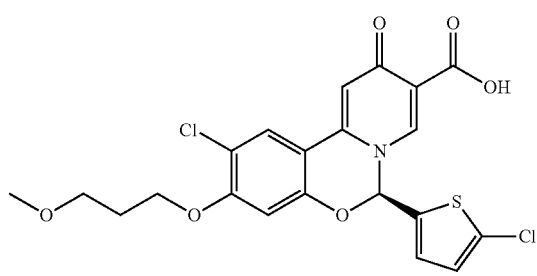
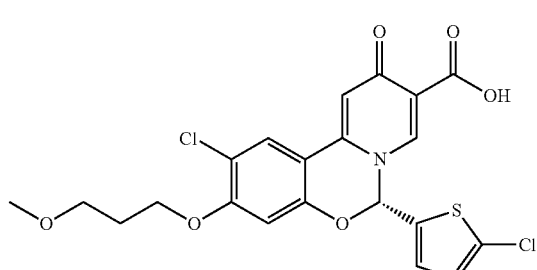
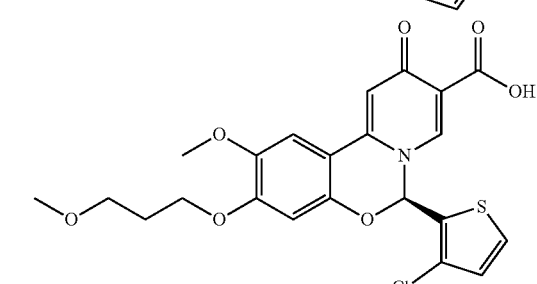
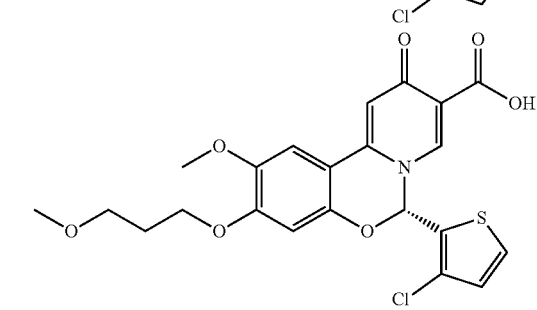

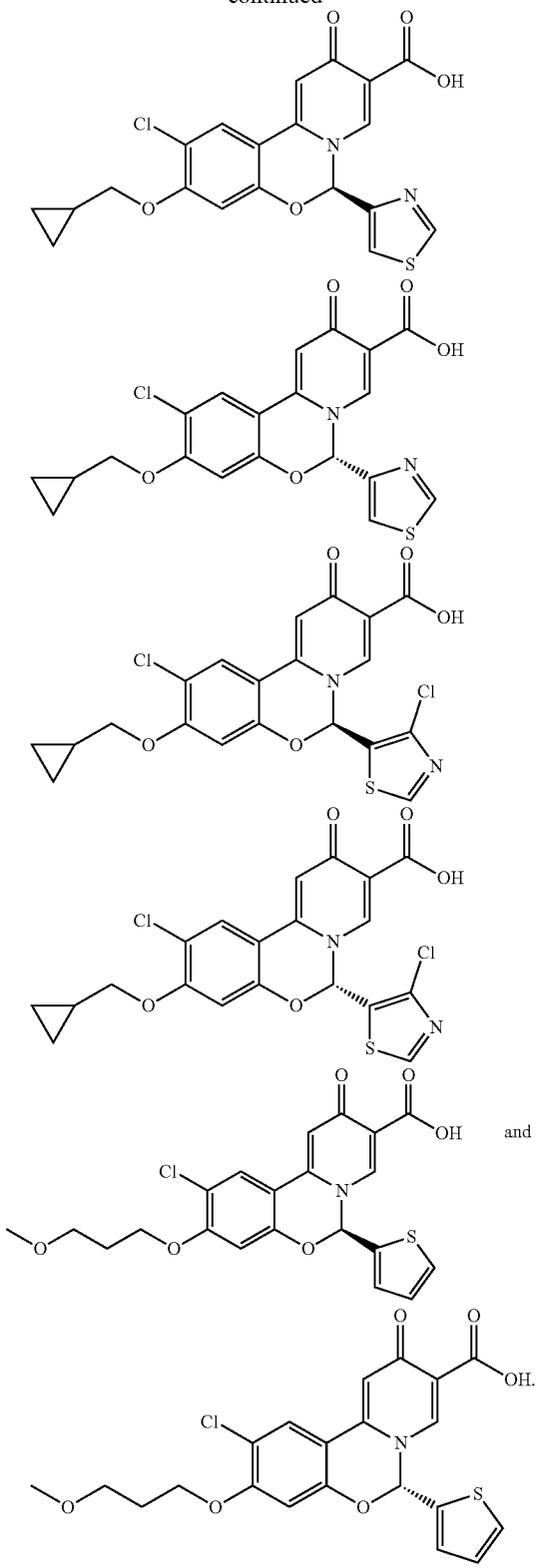

The present disclosure also provides a pharmaceutical composition comprising a therapeutically effective amount of the compound or the pharmaceutically acceptable salt thereof according to claims, and a pharmaceutically acceptable carrier.

The present disclosure also provides the compound or the pharmaceutically acceptable salt thereof, or the pharmaceutical composition in manufacturing a medicament for treating hepatitis B.

Some of the other embodiments of the present disclosure are arbitrarily combined from the above variants.

Technical Effects

The present disclosure creatively designed and synthesized a novel series of compounds having a six-membered nitroxide acetal as a core structure. The compound of the present disclosure overcomes the defect that the six-membered ring nitroxide acetal core structure may be unstable and easily hydrolyzed in the acidic environment of the body through ingenious design. It has been confirmed by relevant experiments that the compound of the present disclosure has good stability in a certain temperature range and acid range. Furthermore, after creatively replacing a carbon atom with an oxygen atom, the activity of the series of compounds of the present disclosure can be well maintained comparing to the prior art. This was verified in an in vitro inhibition experiment on hepatitis B surface antigen activity. At the same time, the design of the oxygen atom replacing the carbon atom prevents the mother nucleus from being dehydrogenated and aromatized as the presence of the carbon atom, and the aqueous solubility of the compound of the present disclosure was improved, so that more excellent druggability properties may be obtained.

Definitions and Descriptions

Unless otherwise indicated, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present disclosure contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present disclosure, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present disclosure can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present disclosure also exists in prodrug form. The prodrug of the compound described herein is the compound that readily undergoes chemical change under physiological condition to be converted into the compound of the present disclosure. Additionally, the prodrug can be converted to the compound of the present disclosure by a chemical or biochemical method in vivo environment.

Certain compounds of the present disclosure can exist in an unsolvated form or a solvated form, including a hydrated form. Generally, the solvated form is equivalent to the unsolvated form, and both are encompassed within the scope of the present disclosure.

Certain compounds of the present disclosure can have an asymmetric carbon atom (optical center) or a double bond. The racemate, diastereomer, geometric isomer and individual isomer are all encompassed within the scope of the present disclosure.

Unless otherwise specified, a wedged bond and a dashed bond ( ) are used to indicate the absolute configuration of a stereogenic center, and are used to indicate the relative configuration of a stereogenic center. When the compound described herein contains an olefinic double bond or other geometric asymmetric centers, E and Z geometric isomers are included unless otherwise specified. Likewise, all tautomeric forms are encompassed within the scope of the present disclosure.

The compound of the present disclosure may present in a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present disclosure. The substituent such as alkyl may have an additional asymmetric carbon atom. All these isomers and mixtures thereof are encompassed within the scope of the present disclosure.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present disclosure may contain an unnatural proportion of atomic isotope at one or more than one atom (s) that constitute the compound. For example, the compound can be radiolabeled with a radioactive isotope, such as tritium ($^3$H), iodine-125 ($^{125}$I) or C-14 ($^{14}$C). All isotopic variations of the compound of the present disclosure, whether radioactive or not, are encompassed within the scope of the present disclosure.

"Optional" or "optionally" means that the subsequent event or condition may occur but not requisite, that the term includes the instance in which the event or condition occurs and the instance in which the event or condition does not occur.

The term "substituted" means one or more than one hydrogen atom (s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to two atoms on a ring, such substituent can be bonded to any atom on the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the structural unit

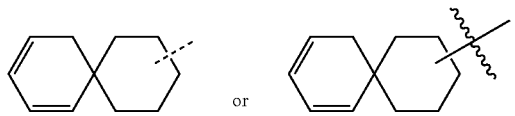

means that it can be substituted at any position on cyclohexyl or cyclohexadiene.

Unless otherwise specified, the term "hetero" represents a heteroatom or a heteroatom group (e. g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N (H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i. e., NO and S (O)p, p is 1 or 2). Nitrogen atom can be substituted or unsubstituted (i. e., N or NR, wherein R is H or other substituents already defined herein). The heterocycle can be attached to the pendant group of any heteroatom or carbon atom to form a stable structure. If the resulting compound is stable, the heterocycle described herein may have a displacement at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1.

As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S (O)p, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Fused-ring compounds and spiro compounds are also included.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2F$) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo ($C_1$-$C_4$)alkyl" is meant to include, but not limited to, trifluoromethyl, 2,2,2-trifluoroethyl, 4-chlorobutyl, 3-bromopropyl and the like. Unless otherwise specified, examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl"

refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy) propyl, and the like.

The term "leaving group" refers to a functional group or atom which can be replaced by another functional group or atom through a displacement reaction (such as affinity displacement reaction). For example, representative leaving groups include: chlorine, bromine; sulfonate group, such as mesylate and tosylate.

The term "protecting group" includes, but is not limited to "amino protecting group", "hydroxy protecting group".

The term "hydroxy protecting group" refers to a protecting group suitable for blocking the side reaction on hydroxy. Representative hydroxy protecting groups include, but are not limited to: alkyl such as methyl; acyl such as benzyl (Bn), and the like.

The compound of the present disclosure can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present disclosure.

All of the solvents used in the present disclosure are commercially available. The present disclosure employs the following abbreviations: HATU represents O-(7-azabenzotriazol-1-yl)-N,N,N',N'-tetramethyluronium hexafluorophosphate.

Compounds are named manually or by ChemDraw® software, the commercially available compounds use their vendor directory names.

DETAILED DESCRIPTION OF THE PREFERRED EMBODIMENT

The following examples further illustrate the present disclosure, but the present disclosure is not limited thereto. The present disclosure has been described in detail herein, specific embodiments thereof are also disclosed herein, it is obvious for the persons skilled in the art that various modifications and improvement may be made to the embodiments of the present disclosure without departing from the spirit and scope of the disclosure.

Embodiment 1

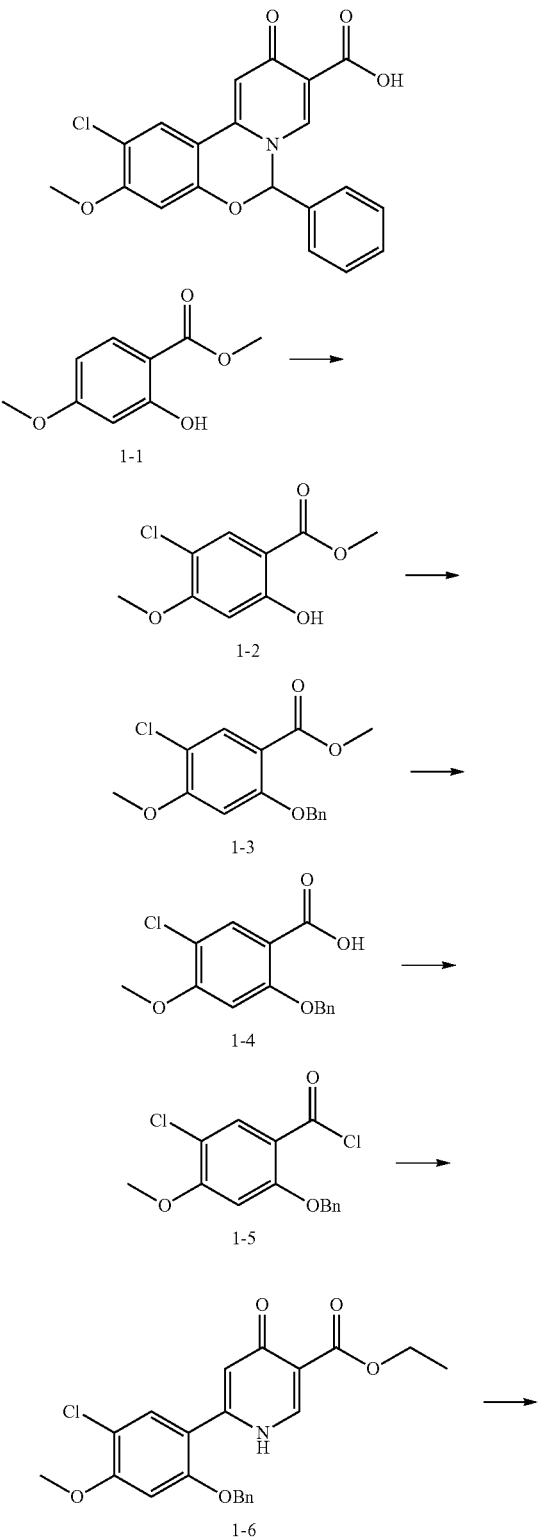

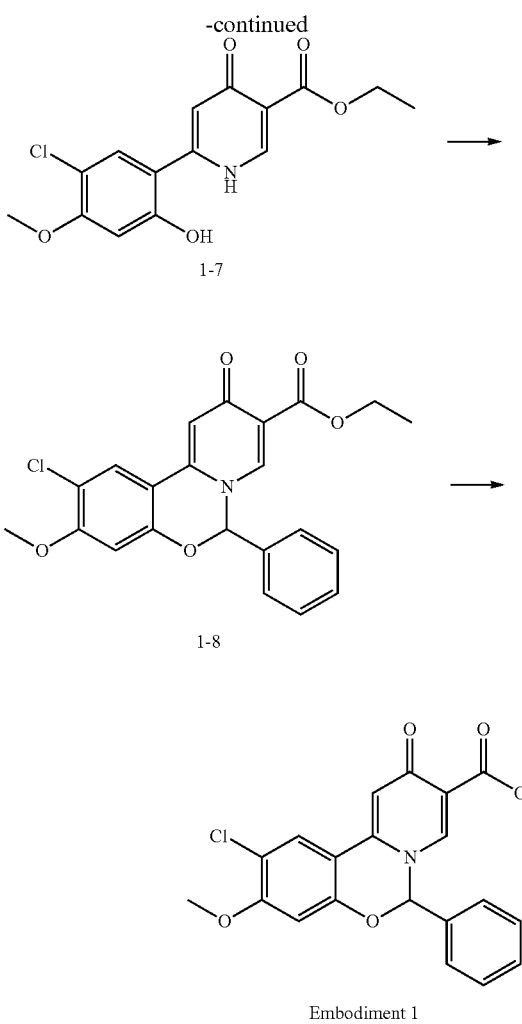

Embodiment 1

Step A: 1-1 (50.00 g, 274.47 mmol) was dissolved in dichloromethane (250 mL), then sulfonyl chloride (44.45 g, 329.36 mmol) was added while stirring, the temperature was controlled between 25-30° C. The system was stirred at 25-30° C. for 48 hours. After completion of the reaction, the system was poured into 300 mL saturated sodium bicarbonate solution, then extracted by EtOAc (150 mL*3), the organic phases was combined, and washed with saturated brine (40 mL*3), dried over anhydrous sodium sulfate, then filtered and concentrated under reduced pressure. The residue was purified by a silica gel column (eluent: PE/EtOAc=10/1-2/1), giving 1-2.

Step B: 1-2 (20.00 g, 92.33 mmol) was dissolved in N,N-dimethylformamide (60 mL), then benzyl bromide (14.26 mL, 120.03 mmol) and potassium carbonate (33.18 g, 240.06 mmol) were added while stirring, the temperature was controlled between 25-30° C. The system was stirred at 25-30° C. for 48 hours. After the completion of the reaction, EtOAc (200 mL) and water (500 mL) were added thereto, then separated to give organic phase. The organic phase was washed with water (50 mL*2) and brine (60 mL*2), dried over anhydrous sodium sulfate, then filtered and concentrated under reduced pressure, giving 1-3.

Step C: 1-3 (36 g, 117.36 mmol) was dissolved in tetrahydrofuran (40 mL) and water (40 mL), then lithium hydroxide monohydrate (29.55 g, 704.18 mmol) was added. The system was stirred at 30° C. for 48 hours. After the completion of the reaction, water (200 mL) was added thereto, then extracted by EtOAc (50 mL*3). The aqueous phase was adjusted pH=1-2, and extracted by EtOAc (50 mL*3), the organic phases were combined, dried over anhydrous sodium sulfate, then filtered and concentrated under reduced pressure, giving 1-4.

Step D: 1-4 (15 g, 51.25 mmol) was dissolved in dichloromethane (150 mL), oxalyl chloride (9.76 g, 76.88 mmol) and N,N-dimethylformamide (394.26 µL, 5.13 mmol) were added under nitrogen atmosphere. The system was stirred at 25° C. for 2 hours, concentrated under reduced pressure to remove the solvent, giving 1-5.

Step E: Lithium hexamethyldisilazide (1 mol/L, 101.06 mL) was added dropwise into 1-5 (15.72 g, 50.53 mmol) and ethyl 2-acetyl-3-dimethylaminoacrylate (7.8 g, 42.11 mmol) in tetrahydrofuran (93 mL) solution at −70° C. The dry ice acetone bath was removed, and acetic acid (84.22 mL, 1.47 mol) and ammonium acetate (4.22 g, 54.74 mmol) were added into the system, tetrahydrofuran was removed by concentration under reduced pressure, then stirred at 60-65° C. for 1.5 hours. After concentration under reduced pressure and evaporation to dryness, the residue was washed with methyl tert-butyl ether (150 mL) and PE (200 mL), then filtered, the filter cake was dried under reduced pressure, giving 1-6.

Step F: 1-6 (5 g, 12.08 mmol) was dissolved in tetrahydrofuran (1.25 L), palladium on carbon (10%, 500 mg) was added under nitrogen atmosphere, after the system was charged by hydrogen for several times, the system was stirred at 25° C. for 15 mins under hydrogen atmosphere (15 Psi). Then after filtration, the residue was dissolved in the mixture of dichloromethane/methanol=10/1 (1500 mL), then filtered to remove palladium on carbon, the filtrate was concentrated under reduced pressure to give 1-7.

$^1$H NMR (400 MHz, DMSO-d6) δ 8.54 (s, 1H), 7.72 (s, 1H), 6.78 (s, 1H), 6.51 (s, 1H), 4.23 (q, J=7.1 Hz, 2H), 3.83 (s, 3H), 1.30 (t, J=7.1 Hz, 3H).

Step G: 1-7 (3 g, 9.27 mmol) was dissolved in N,N-dimethylformamide (60 mL), then potassium carbonate (10.25 g, 74.16 mmol) and dibromotoluene (6.59 g, 27.81 mmol) were added, the system was stirred at 100° C. for 32 hours. The reaction mixture was quenched by water (300 mL), then extracted by EtOAc (300 mL*2). The organic phases were combined and washed with water (300 mL*2), dried over anhydrous sodium sulfate, then filtered and concentrated under reduced pressure, and purified by silica gel column (eluent: PE/EtOAc=10:1-1:0), giving 1-8.

$^1$H NMR (400 MHz, CDCl$_3$) 7.96 (s, 1H), 7.63 (s, 1H), 7.51-7.44 (m, 3H), 7.34 (dd, J=1.9, 7.5 Hz, 2H), 6.83 (s, 1H), 6.63 (s, 1H), 6.59 (s, 1H), 4.31 (q, J=7.1 Hz, 2H), 3.92 (s, 3H), 1.33 (t, J=7.1 Hz, 3H).

Step H: 1-8 (100.00 mg, 242.81 µmol) was dissolved in methanol (2 mL) and water (1 mL), then sodium hydroxide (19.42 mg, 485.62 µmol) was added and stirred at 25° C. for 16 hours. The reaction mixture was adjusted by 1 mol/L hydrochloric acid to pH=3, and extracted by dichloromethane (15 mL*2). The organic phases were combined, and washed with brine, dried over anhydrous sodium sulfate, then filtered and concentrated under reduced pressure. The residue was washed with PE/EtOAc=5/1, filtered to give the filter cake which was dried under reduced pressure, giving embodiment 1.

$^1$H NMR (400 MHz, DMSO-d6) δ 16.12 (s, 1H), 8.72 (s, 1H), 8.26 (s, 1H), 7.54 (s, 1H), 7.51 (s, 1H), 7.47-7.43 (m, 3H), 7.27 (dd, J=2.6, 6.4 Hz, 2H), 7.11 (s, 1H), 3.92 (s, 3H).

Embodiment 2

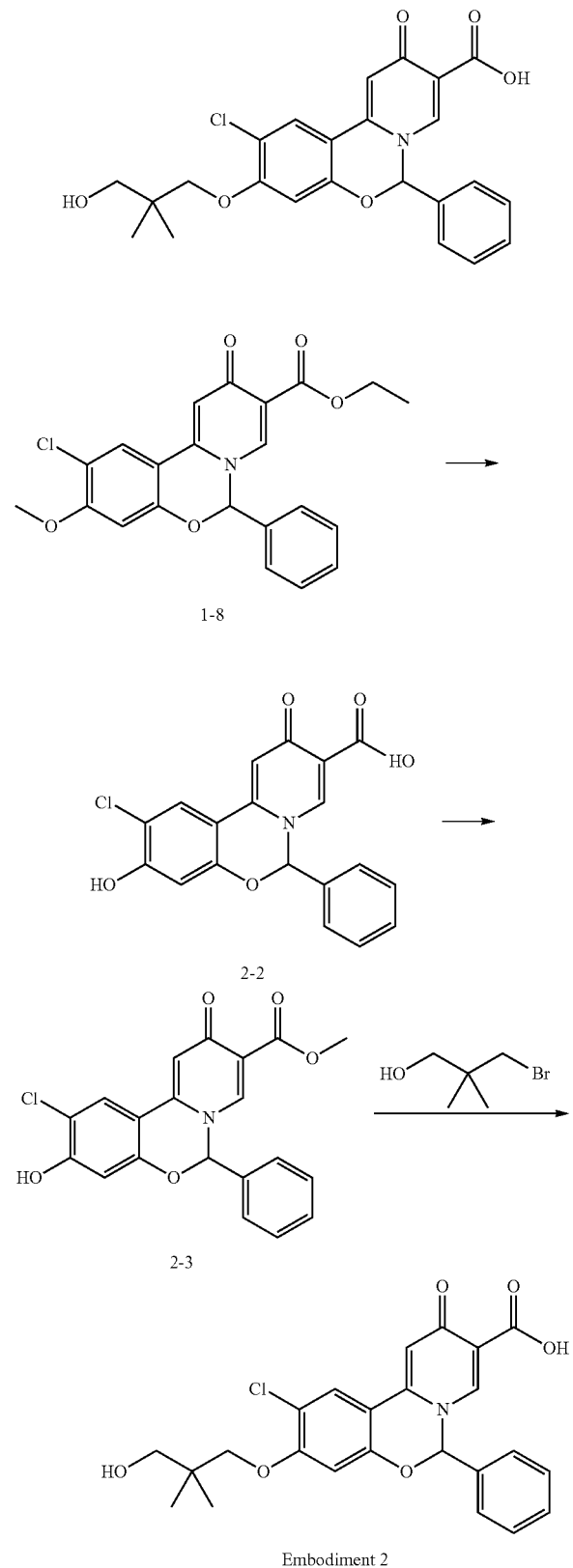

Step A: 1-8 (1.60 g, 3.89 mmol) was dissolved in dichloromethane (160 mL), boron tribromide (2.25 mL, 23.34 mmol) was added dropwise at 70° C., and stirred at 25° C. for 16 hours. The reaction mixture was quenched by methanol (60 mL) at 0° C., after concentration under reduced pressure and evaporation to dryness, water (50 mL) and dichloromethane (30 mL) were added, then filtered to give a solid, which was then dried under reduced pressure, giving 2-2.

$^1$H NMR (400 MHz, DMSO-d6) δ 11.53 (br s, 1H), 8.73 (s, 1H), 8.18 (s, 1H), 7.51 (s, 1H), 7.46-7.41 (m, 5H), 7.21 (dt, J=2.4, 3.5 Hz, 2H), 6.75 (s, 1H).

Step B: 2-2 (1.20 g, 3.25 mmol) was dissolved in methanol (30 mL), thionyl chloride (2.36 mL, 32.50 mmol) was added at 0° C., the reaction mixture was stirred at 50° C. for 16 hours. The system was concentrated under reduced pressure and evaporated to dryness, the solid was washed with PE/EtOAc=3/1 (12 mL), and filtered to give the filter cake, which was dried under reduced pressure, giving 2-3.

Step C: 2-3 (100.00 mg, 260.57 μmol), 3-bromo-2,2-dimethyl-1-propanol (65.29 mg, 390.86 μmol), sodium iodide (7.81 mg, 52.11 μmol), potassium carbonate were mixed in N,N-dimethylformamide (2 mL), and stirred at 120° C. for 16 hours. The reaction mixture was adjusted by 1 mol/L hydrochloric acid to pH=3-4, then extracted by dichloromethane (15 mL*2), the organic phases was combined and washed with water (20 mL*2), dried over anhydrous sodium sulfate, then filtered and concentrated under reduced pressure. The solid obtained was purified by HPLC (column: Boston Green ODS 150*30 5 μm; mobile phase: [water (0.225% formic acid)-acetonitrile]; elution gradient: 35%-65%, 12 mins), giving embodiment 2 (20.90 mg, 44.24 mmol, 16.98%).

$^1$H NMR (400 MHz, DMSO-d6) δ 8.74 (br s, 1H), 8.35 (s, 1H), 8.21 (br d, J=0.7 Hz, 1H), 7.55 (s, 1H), 7.45-7.41 (m, 3H), 7.21 (br s, 2H), 7.05 (s, 1H), 3.83 (s, 2H), 3.28 (s, 2H), 0.93 (s, 6H).

Embodiments 3 to 9 were obtained according to the same method as embodiment 2.

Embodiment 3

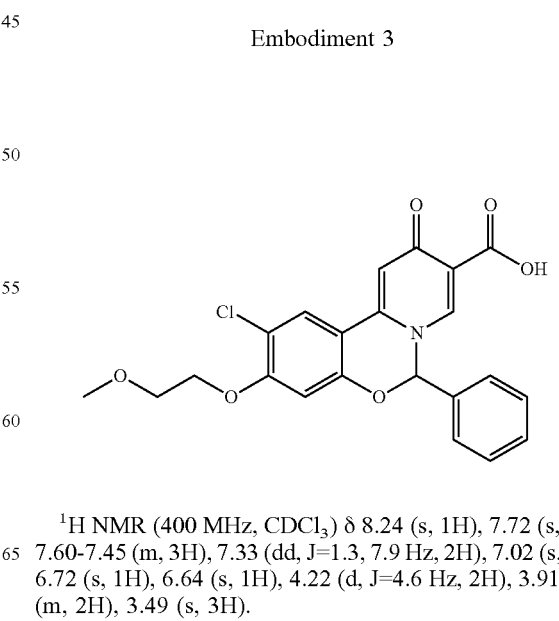

$^1$H NMR (400 MHz, CDCl$_3$) δ 8.24 (s, 1H), 7.72 (s, 1H), 7.60-7.45 (m, 3H), 7.33 (dd, J=1.3, 7.9 Hz, 2H), 7.02 (s, 1H), 6.72 (s, 1H), 6.64 (s, 1H), 4.22 (d, J=4.6 Hz, 2H), 3.91-3.73 (m, 2H), 3.49 (s, 3H).

Embodiment 4

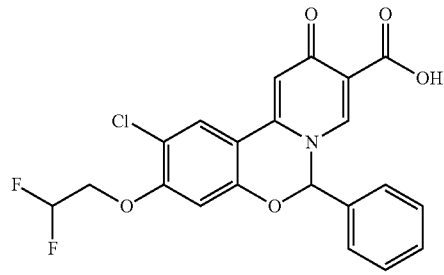 [SMILES: O=C(O)c1cn2c(cc1=O)-c1cc(Cl)c(OCC(F)F)cc1OC2c1ccccc1]

<sup>1</sup>H NMR (400 MHz, CDCl<sub>3</sub>) δ 8.25 (s, 1H), 7.76 (s, 1H), 7.57-7.51 (m, 3H), 7.33 (br d, J=6.5 Hz, 2H), 7.05 (s, 1H), 6.70 (s, 1H), 6.65 (s, 1H), 6.32 (s, 0.25H), 6.19 (s, 0.45H), 6.05 (s, 0.3H), 4.29 (dt, J=3.8, 12.6 Hz, 2H).

Embodiment 5

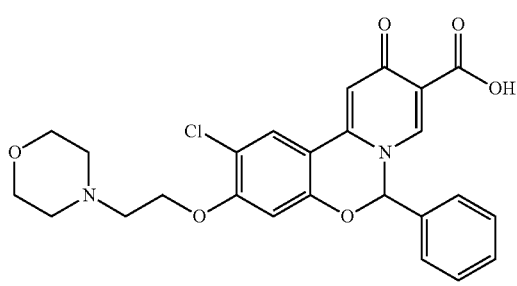 [SMILES: O=C(O)c1cn2c(cc1=O)-c1cc(Cl)c(OCCN3CCOCC3)cc1OC2c1ccccc1]

<sup>1</sup>H NMR (400 MHz, DMSO-d6) δ 8.35 (s, 1H), 7.54 (s, 2H), 7.46-7.43 (m, 4H), 7.24 (br s, 1H), 7.14 (s, 1H), 7.13-7.13 (m, 1H), 4.25 (br t, J=5.3 Hz, 3H), 3.61-3.53 (m, 6H), 2.73 (t, J=5.6 Hz, 3H).

Embodiment 6

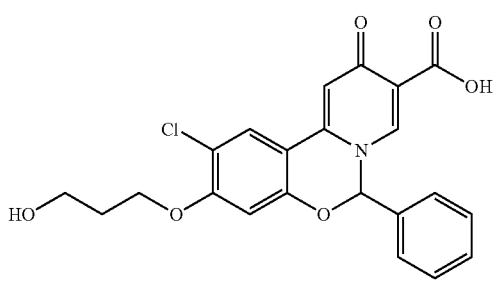 [SMILES: O=C(O)c1cn2c(cc1=O)-c1cc(Cl)c(OCCCO)cc1OC2c1ccccc1]

<sup>1</sup>H NMR (400 MHz, CD<sub>3</sub>OD) δ 8.51 (br s, 1H), 8.35 (s, 1H), 7.99 (br s, 1H), 7.49 (br s, 3H), 7.37 (br s, 2H), 7.19 (br s, 2H), 6.96 (s, 1H), 4.23 (br t, J=6.0 Hz, 2H), 3.79 (t, J=6.1 Hz, 2H), 2.05 (br t, J=6.1 Hz, 3H).

Embodiment 7

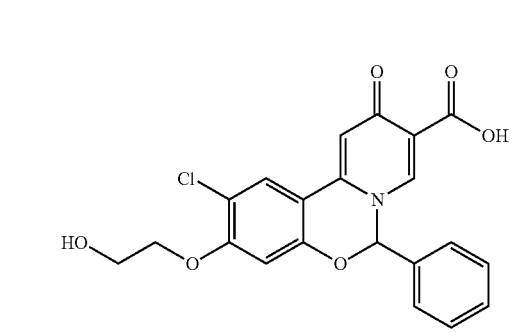 [SMILES: O=C(O)c1cn2c(cc1=O)-c1cc(Cl)c(OCCO)cc1OC2c1ccccc1]

<sup>1</sup>H NMR (400 MHz, CD<sub>3</sub>OD) δ 8.55-8.41 (m, 2H), 7.98 (br s, 1H), 7.48 (br s, 3H), 7.37 (br s, 2H), 7.19 (br s, 2H), 6.97 (br s, 1H), 4.20 (br s, 2H), 3.94 (br s, 2H).

Embodiment 8

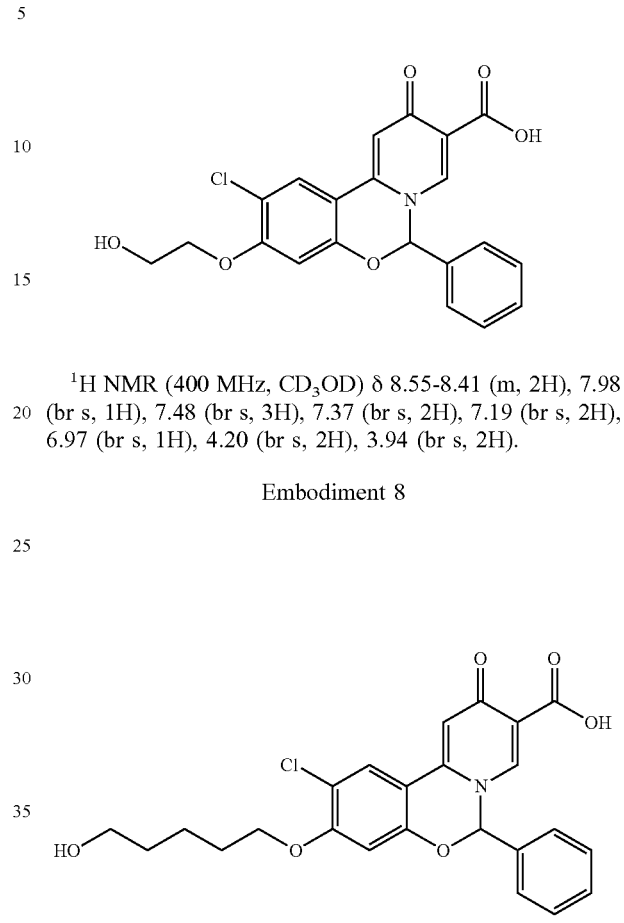

<sup>1</sup>H NMR (400 MHz, CD<sub>3</sub>OD) δ 8.50 (br s, 1H), 7.99 (br s, 1H), 7.54-7.32 (m, 6H), 7.22 (br s, 1H), 6.93 (br s, 1H), 5.13-5.06 (m, 1H), 4.19-4.07 (m, 1H), 4.13 (br s, 1H), 3.60 (br t, J=5.8 Hz, 2H), 1.88 (br s, 2H), 1.61 (br s, 5H).

Embodiment 9

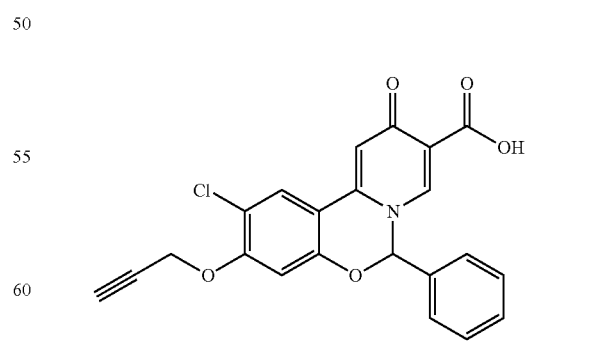

<sup>1</sup>H NMR (400 MHz, CDCl<sub>3</sub>) δ 8.22 (s, 1H), 7.75 (s, 1H), 7.61-7.48 (m, 3H), 7.37 (d, J=6.5 Hz, 2H), 7.04 (s, 1H), 6.88 (s, 1H), 6.63 (s, 1H), 4.85 (t, J=2.4 Hz, 2H), 2.63 (t, J=2.4 Hz, 1H).

Embodiment 10

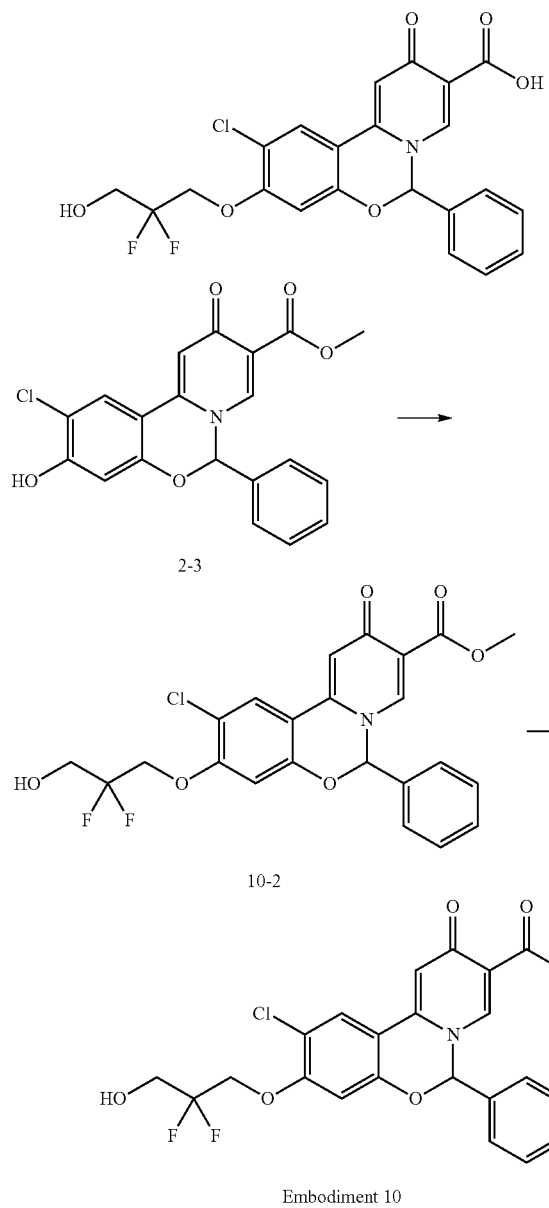

Embodiment 10

Step A: 2-3 (50.00 mg, 130.28 mol) was dissolved in DMF (2 mL), and potassium carbonate (36.01 mg, 260.56 mmol), (2,2-difluoro-3-hydroxy-propyl) 4-p-toluenesulfonic acid (34.69 mg, 130.28 μmol) were added, the system was stirred at 100° C. for 12 hours. The reaction mixture was adjusted by 1 mol/L hydrochloric acid to pH=3-4, and extracted by dichloromethane (15 mL*2), the organic phases were combined and washed with water (20 mL*2), dried over anhydrous sodium sulfate, then filtered and concentrated under reduced pressure. Then the residue was purified by silica gel plate (silicon dioxide, dichloromethane:methanol=15:1), giving 10-2.

Step B: 10-2 (40.00 mg, 26.79 μmol) was dissolved in tetrahydrofuran (1 mL), methanol (1 mL) and water (1 mL), lithium hydroxide monohydrate (1.12 mg, 26.79 μmol) was added, the system was stirred at 25° C. for 1 hours. The reaction mixture was adjusted to pH=3-4, then purified by HPLC (column: Boston Green ODS 150*30 5 μm; mobile phase: [water (0.225% formic acid)-acetonitrile]; elution gradient: 30%-54%, 10 mins), giving embodiment 10.

$^1$H NMR (400 MHz, CD$_3$OD) δ 8.51 (s, 1H), 8.08 (s, 1H), 7.50 (br d, J=3.3 Hz, 3H), 7.38 (br d, J=4.4 Hz, 2H), 7.24 (br d, J=18.3 Hz, 2H), 7.07 (s, 1H), 4.45 (br t, J=11.4 Hz, 2H), 3.91 (t, J=13.1 Hz, 2H).

Embodiments 11-12 were obtained according to the same method as embodiment 10.

Embodiment 11

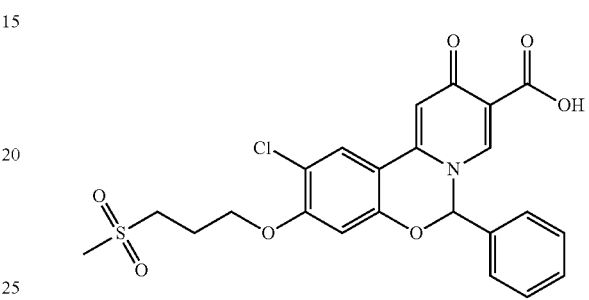

$^1$H NMR (400 MHz, DMSO-d6) δ 8.73 (s, 1H), 8.27 (s, 1H), 7.54 (s, 1H), 7.52 (s, 1H), 7.47-7.43 (m, 3H), 7.26 (dd, J=2.6, 6.5 Hz, 2H), 7.13 (s, 1H), 4.26 (t, J=6.1 Hz, 2H), 3.28-3.24 (m, 2H), 3.03 (s, 3H), 2.23-2.13 (m, 2H).

Embodiment 12

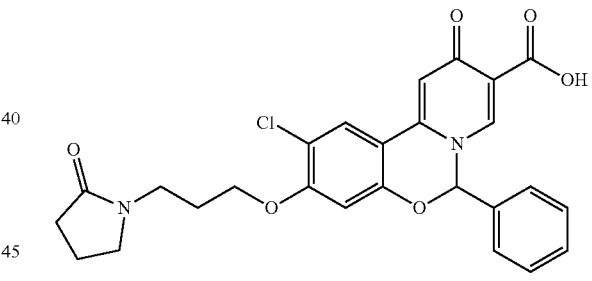

$^1$H NMR (400 MHz, CD$_3$OD) δ 8.35 (br s, 1H), 7.91 (s, 1H), 7.38 (br s, 3H), 7.27 (br s, 2H), 7.09 (br d, J=17.0 Hz, 2H), 6.86-6.81 (m, 1H), 4.04 (br s, 2H), 3.45-3.37 (m, 5H), 2.29-2.21 (m, 2H), 2.02-1.97 (m, 2H), 1.96-1.92 (m, 2H).

Embodiment 13 (13_A and 13_B)

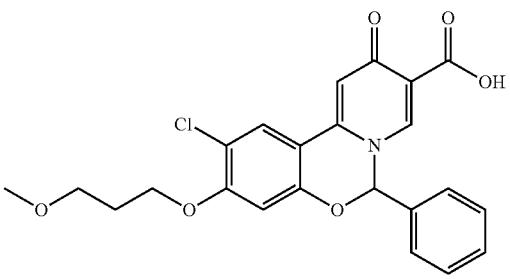

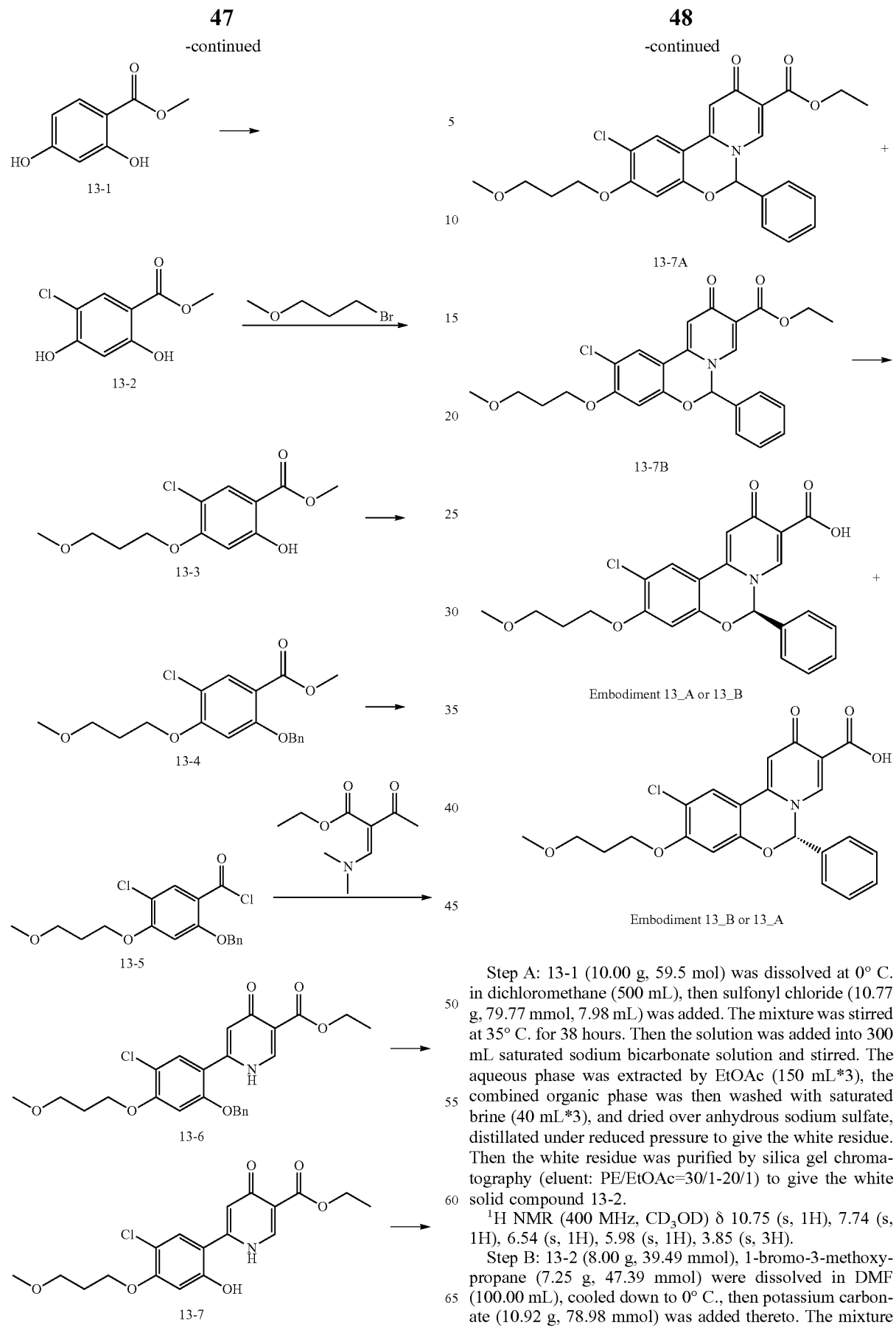

Step A: 13-1 (10.00 g, 59.5 mol) was dissolved at 0° C. in dichloromethane (500 mL), then sulfonyl chloride (10.77 g, 79.77 mmol, 7.98 mL) was added. The mixture was stirred at 35° C. for 38 hours. Then the solution was added into 300 mL saturated sodium bicarbonate solution and stirred. The aqueous phase was extracted by EtOAc (150 mL*3), the combined organic phase was then washed with saturated brine (40 mL*3), and dried over anhydrous sodium sulfate, distilled under reduced pressure to give the white residue. Then the white residue was purified by silica gel chromatography (eluent: PE/EtOAc=30/1-20/1) to give the white solid compound 13-2.

$^1$H NMR (400 MHz, CD$_3$OD) δ 10.75 (s, 1H), 7.74 (s, 1H), 6.54 (s, 1H), 5.98 (s, 1H), 3.85 (s, 3H).

Step B: 13-2 (8.00 g, 39.49 mmol), 1-bromo-3-methoxypropane (7.25 g, 47.39 mmol) were dissolved in DMF (100.00 mL), cooled down to 0° C., then potassium carbonate (10.92 g, 78.98 mmol) was added thereto. The mixture was heated to 25° C. and stirred for 10 hours. Then EtOAc (300 mL) and water (50 mL) were added into the solution, and stirred at 25° C. for 10 mins. The organic phase was separated and washed with saturated brine (40 mL*3), and dried over anhydrous sodium sulfate, then concentrated under reduced pressure to give a yellow liquid. The yellow liquid was purified by silica gel chromatography (eluent: PE/EtOAc=30/1-20/1) to give white solid compound 13-3.

$^1$H NMR (400 MHz, CDCl$_3$) δ 10.90 (s, 1H), 7.82 (s, 1H), 6.52 (s, 1H), 4.16 (t, J=6.0 Hz, 2H), 3.94 (s, 3H), 3.60 (t, J=6.0 Hz, 2H), 3.38 (s, 3H), 2.13 (t, J=6.0 Hz, 2H).

Step C: Potassium carbonate (4.76 g, 34.45 mmol) was added into 13-3 (3.64 g, 13.25 mmol), benzyl chloride (2.18 g, 17.23 mmol, 1.98 mL) in DMF (10.00 mL). The mixture was stirred at 25° C. for 20 hours. EtOAc (150 mL) and water (30 mL) were added into the solution, the solution was stirred at 20° C. for 10 mins. The organic phase was separated and washed with water (30 mL*2) and saturated brine (30 mL*2), then dried over anhydrous sodium sulfate, and concentrated under reduced pressure to give yellow liquid compound 13-4.

Step D: 13-4 (2.00 g, 5.48 mmol) and lithium hydroxide monohydrate (1.38 g, 32.89 mmol) in tetrahydrofuran (20 mL) and water (10 mL) were stirred at 10-20° C. for 10 hours. Then the solution was washed with EtOAc/PE 1/1 (5 mL*3). The aqueous phase was adjusted to PH=1-2. Then the mixture was extracted by dichloromethane (50 mL*3), the organic phase was combined and dried over anhydrous sodium sulfate, then concentrated under reduced pressure to give white solid compound 2-benzyloxy-5-chloro-4-(3-methoxypropane) benzoic acid (1.30 g, 3.71 mmol, 67.63%). Thionyl chloride (508.60 mg, 4.28 mmol, 310.12 μL) was added into 2-benzyloxy-5-chloro-4-(3-methoxypropane) benzoic acid (1.00 g, 2.85 mmol) in dichloromethane (10.00 mL). The mixture was stirred at 25° C. for 1 hours. Then the mixture was concentrated under reduced pressure to give a residue. Then the residue was dissolved in toluene, and then further concentrated under reduced pressure to give a residue. The residue 13-5 was kept under nitrogen atmosphere.

$^1$H NMR (400 MHz, DMSO-d$_6$) δ 12.87-12.22 (m, 1H), 7.74 (s, 1H), 7.53 (br d, J=7.2 Hz, 2H), 7.40 (t, J=7.6 Hz, 2H), 7.36-7.30 (m, 1H), 6.94 (s, 1H), 5.27 (s, 2H), 4.20 (s, 2H), 3.50 (s, 2H), 3.26 (s, 3H), 1.98 (t, J=6.4 Hz, 2H).

Step E: 13-5 (2.94 g, 7.96 mmol) and ethyl 2-(dimethylaminomethylene)-3-oxobutanoate (1.62 g, 8.6 mmol, 1.10 eq) in tetrahydrofuran (20 mL) was added dropwise in 5 mins into lithium hexamethyldisilazide (1 mol/L, 23.88 mL) in tetrahydrofuran (20 mL) at −70° C. Then the cooling bath was removed and the mixture was continuously stirred for 5 mins. Then ammonium acetate (3.23 g, 41.95 mmol) and acetic acid (67.85 g, 1.13 mmol) were added into the mixture, and most of the tetrahydrofuran was removed by rotary evaporator at 60° C. Then the residue was heated to 60-65° C. for 1.5 hours. The reaction mixture was cooled down and water (40 mL) and dichloromethane (200 mL) were added thereto. The mixture was stirred for 10 mins and then separated, the organic phase was washed with water (10 mL*3) and sodium dicarbonate solution, dried and then concentrated to give the yellow residue. The residue was then purified by silica gel chromatography (eluent: PE/EtOAc=10/1) to give the compound 13-6.

Step F: Activated wet palladium on carbon (500 mg) was added into 13-6 (3.00 g, 6.36 mmol) in tetrahydrofuran (20 mL). The mixture was stirred at 25° C. under hydrogen atmosphere (15 psi) for 2 hours. Then the brown suspension was filtered to give a yellow liquid, then concentrated under reduced pressure to give a yellow residue. The yellow residue was triturated twice in PE/EtOAc (4/1) and then filtered to give the pale yellow solid compound 13-7.

Step G: 13-7 (800.00 mg, 2.10 mmol), potassium carbonate (580.48 mg, 4.20 mmol) and dibromotoluene (551.10 mg, 2.21 mmol) in DMF (20.00 mL) solution were stirred at 100° C. for 10 hours. Then EtOAc (60 mL) and water (10 mL) were added into the reaction mixture, the organic phase was then separated, the aqueous phase was extracted by EtOAc (20 mL*3), all of the organic phase was combined and washed with water (10 mL*3) and saturated brine (10 mL*3), then concentrated under reduced pressure to give a yellow liquid. The yellow liquid was purified by silica gel chromatography (eluent: PE/EtOAc=10/1-5/1) to give a white solid. Then the solid was separated by chiral chromatography column (column: AD (250 mm*30 mm, 10 μm); mobile phase: [0.1% NH$_3$H$_2$O-MeOH]; elution gradient: 50%-50%, 5.9 min; 800 min), giving embodiment 13-7A (t=3.831 min) and embodiment 13-7B (t=4.552 min).

Step H: Lithium hydroxide monohydrate (107.15 mg, 2.55 mmol) was added into 13-7A (240.00 mg, 510.74 mmol) in methanol (9 mL) and water (3 mL). Then the mixture was stirred at 25° C. for 19 hours. Then the mixture was washed with EtOAc/PE (¼) (5 mL), and adjusted by diluted hydrochloric acid solution (1 mol/L) to pH=2-3. Then the mixture was extracted by dichloromethane (40 mL*3). The organic phases were combined and concentrated under reduced pressure to give a yellow liquid. The yellow liquid was purified by HPLC (column: Agela ASB 150*25 mm*5 μm; mobile phase: [water (0.1% TFA)-ACN]; elution gradient: 42%-72%, 10 min) to give embodiment 13_A.

$^1$H NMR (400 MHz, CDCl$_3$) δ 15.46 (br s, 1H), 8.15 (s, 1H), 7.62 (s, 1H), 7.49-7.37 (m, 3H), 7.24 (br d, J=7.0 Hz, 2H), 6.93 (s, 1H), 6.61 (s, 1H), 6.55 (s, 1H), 4.67 (br s, 3H), 4.08 (t, J=6.2 Hz, 2H), 3.51 (t, J=5.9 Hz, 2H), 3.28 (s, 3H), 2.08-1.93 (m, 2H).

Step I: Lithium hydroxide monohydrate (129.48 mg, 3.09 mmol) was added into 13-7B (290.00 mg, 617.14 mmol) in methanol (9 mL) and water (3 mL). Then the solution was stirred at 25° C. for 19 hours. Then the mixture was washed with EtOAc/PE (¼) (5 mL), and adjusted by hydrochloric acid solution (1 mol/L) to pH=2-3. Then the mixture was extracted by dichloromethane (40 mL*3). The organic phases were combined and concentrated under reduced pressure to give a liquid. The yellow liquid was purified by HPLC (column: Agela ASB 150*25 mm*5 μm; mobile phase: [water (0.1% TFA)-ACN]; elution gradient: 42%-72%, CO$_2$, 11 min) to give embodiment 13_B.

$^1$H NMR (400 MHz, CDCl$_3$) δ 8.14 (s, 1H), 7.62 (s, 1H), 7.50-7.36 (m, 3H), 7.24 (br d, J=7.0 Hz, 1H), 7.26-7.22 (m, 1H), 6.93 (s, 1H), 6.61 (s, 1H), 6.54 (s, 1H), 4.08 (t, J=6.2 Hz, 2H), 3.51 (t, J=5.9 Hz, 2H), 3.28 (s, 3H), 2.04 (t, J=6.1 Hz, 2H).

Embodiment 14

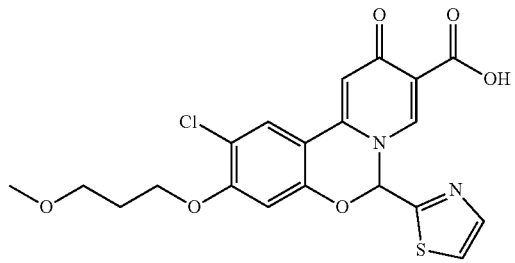

-continued

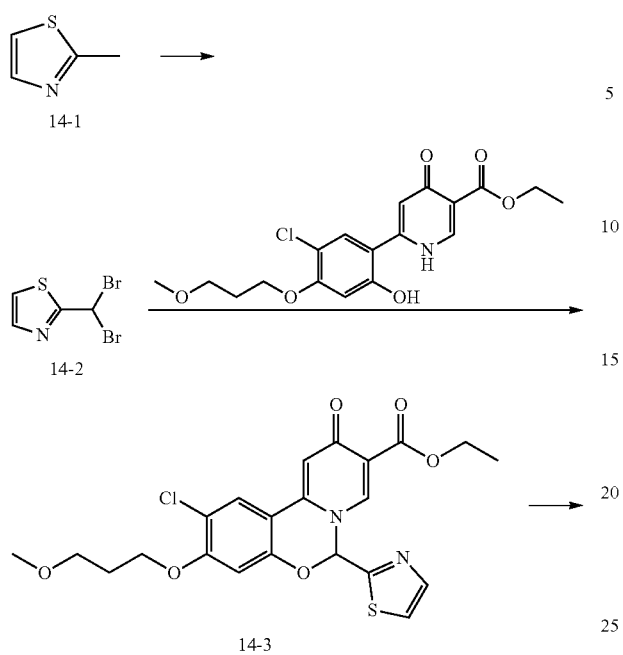

Step A: Benzoyl peroxide (122.21 mg, 504.50 mmol) was added into 14-1 (1.00 g, 10.09 mmol) and bromo succinimide (3.77 g, 21.19 mmol) in tetrachloromethane (10.00 mL), the mixture obtained was illuminated at 80° C. and stirred for 16 hours. After the completion of the reaction, the solvent in the mixture was removed, then the mixture was dissolved in 60 mL water, and extracted by EtOAc (50 mL*3), the organic phases was combined and washed with 60 mL saturated brine, and dried over anhydrous sodium sulfate, then filtered and concentrated to give the residue. The residue was purified by silica gel chromatography (eluent: PE/EtOAc=1/0-10/1) to give compound 14-2.

$^1$H NMR (400 MHz, CDCl$_3$) δ 7.82 (d, J=8.0 Hz 1H), 7.50 (d, J=7.6 Hz 1H), 6.66 (s, 1H).

Embodiment 14 was obtained according to the method of Step B, C in embodiment 13.

Embodiment 14: $^1$H NMR (400 MHz, CDCl$_3$) δ 15.44 (br s, 1H), 8.60 (br s, 1H), 7.76 (br d, J=2.7 Hz, 1H), 7.64 (s, 1H), 7.47 (br d, J=2.4 Hz, 1H), 7.11 (br s, 1H), 6.97 (s, 1H), 6.76 (s, 1H), 4.19 (br t, J=6.0 Hz, 2H), 3.60 (br t, J=5.2 Hz, 2H), 3.37 (s, 3H), 2.17-2.10 (m, 2H).

Embodiments 15-24 may be obtained according to the method in embodiment 14.

Embodiment 15

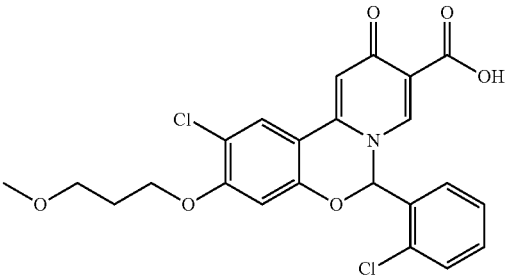 [SMILES: COCCCOc1cc2c(cc1Cl)-c1cc(=O)c(C(=O)O)cn1C(c1ccccc1Cl)O2]

$^1$H NMR (400 MHz, CDCl$_3$) δ 15.47 (s, 1H), 8.00 (s, 1H), 7.78 (s, 1H), 7.63-7.52 (m, 2H), 7.50-7.39 (m, 2H), 7.02 (s, 1H), 6.84 (s, 1H), 6.70 (s, 1H), 4.16 (t, J=6.2 Hz, 2H), 3.59 (t, J=5.9 Hz, 2H), 3.39-3.31 (m, 3H), 2.12 (quin, J=6.1 Hz, 2H).

Embodiment 16

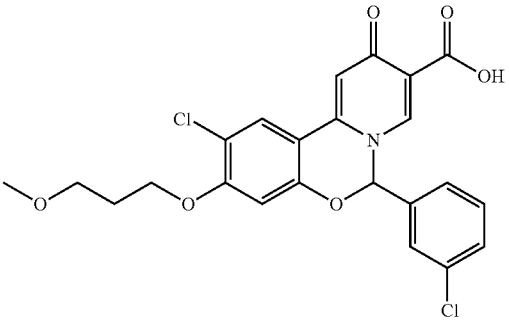 [SMILES: COCCCOc1cc2c(cc1Cl)-c1cc(=O)c(C(=O)O)cn1C(c1cccc(Cl)c1)O2]

$^1$H NMR (400 MHz, CDCl$_3$) δ 15.46 (br s, 1H), 8.28 (s, 1H), 7.69 (s, 1H), 7.52-7.46 (m, 1H), 7.44-7.37 (m, 1H), 7.32 (s, 1H), 7.12 (br d, J=7.2 Hz, 1H), 7.01 (s, 1H), 6.73-6.62 (m, 2H), 4.16 (t, J=6.0 Hz, 2H), 3.59 (t, J=6.0 Hz, 2H), 3.36 (s, 3H), 2.13 (t, J=6.4 Hz, 2H).

Embodiment 17

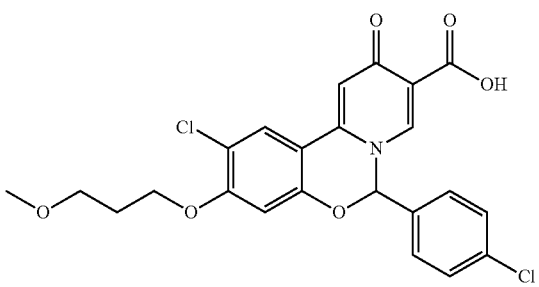 [SMILES: COCCCOc1cc2c(cc1Cl)-c1cc(=O)c(C(=O)O)cn1C(c1ccc(Cl)cc1)O2]

$^1$H NMR (400 MHz, CDCl$_3$) δ 15.49 (br s, 1H), 8.26 (s, 1H), 7.68 (s, 1H), 7.46 (br d, J=8.0 Hz, 2H), 7.23 (br d, J=8.0 Hz, 2H), 7.00 (s, 1H), 6.75-6.58 (m, 2H), 4.15 (t, J=6.0 Hz, 2H), 3.59 (t, J=6.0 Hz, 2H), 3.36 (s, 3H), 2.12 (br t, J=6.0 Hz, 2H).

Embodiment 18

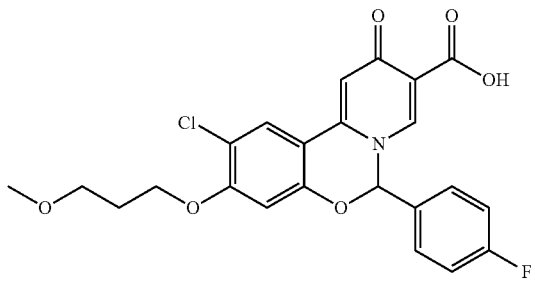 [SMILES: COCCCOc1cc2c(cc1Cl)-c1cc(=O)c(C(=O)O)cn1C(c1ccc(F)cc1)O2]

$^1$H NMR (400 MHz, CDCl$_3$) δ 8.21 (s, 1H), 7.70 (s, 1H), 7.37-7.29 (m, 2H), 7.23-7.15 (m, 2H), 7.00 (s, 1H), 6.68 (s, 1H), 6.62 (s, 1H), 4.16 (br t, J=6.0 Hz, 2H), 3.59 (t, J=6.0 Hz, 2H), 3.36 (s, 3H), 2.17-2.09 (m, 2H).

Embodiment 19

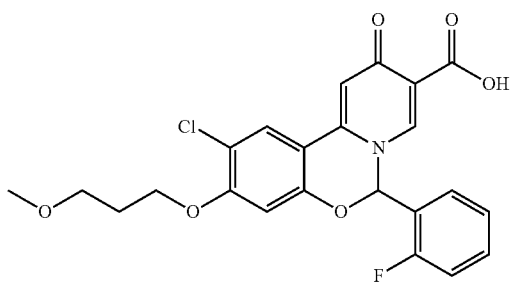 [SMILES: COCCCOc1cc2c(cc1Cl)-c1cc(=O)c(C(=O)O)cn1C(c1ccccc1F)O2]

$^1$H NMR (400 MHz, CDCl$_3$) δ 15.46 (br s, 1H), 8.14 (s, 1H), 7.76 (s, 1H), 7.63-7.56 (m, 1H), 7.32-7.29 (m, 2H), 7.28 (br s, 1H), 7.02 (s, 1H), 6.81 (s, 1H), 6.69 (s, 1H), 4.15 (t, J=6.0 Hz, 2H), 3.58 (t, J=6.0 Hz, 2H), 3.35 (s, 3H), 2.12 (t, J=6.0 Hz, 2H).

Embodiment 20

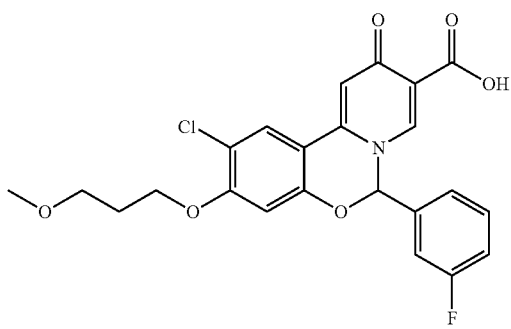

$^1$H NMR (400 MHz, CDCl$_3$) δ 15.46 (br s, 1H), 8.29 (s, 1H), 7.68 (s, 1H), 7.49-7.42 (m, 1H), 7.24-7.18 (m, 1H), 7.05 (br d, J=9.2 Hz, 1H), 7.03-6.99 (m, 2H), 6.71-6.64 (m, 2H), 4.16 (t, J=6.0 Hz, 2H), 3.59 (t, J=6.0 Hz, 2H), 3.36 (s, 3H), 2.13 (quin, J=6.0 Hz, 2H).

Embodiment 21

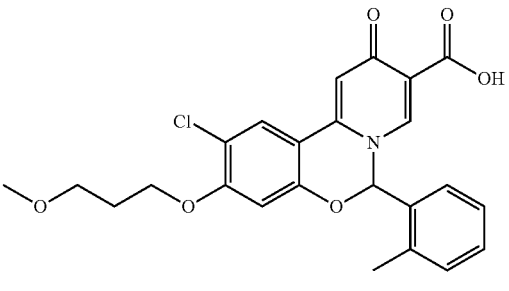 [SMILES: COCCCOc1cc2c(cc1Cl)-c1cc(=O)c(C(=O)O)cn1C(c1ccccc1C)O2]

$^1$H NMR (400 MHz, CDCl$_3$) δ 15.55 (br s, 1H), 8.05 (s, 1H), 7.76 (s, 1H), 7.47 (t, J=7.0 Hz, 1H), 7.37 (d, J=7.5 Hz, 1H), 7.33 (t, J=7.6 Hz, 1H), 7.21 (d, J=7.7 Hz, 1H), 7.02 (s, 1H), 6.68-6.61 (m, 2H), 4.15 (t, J=6.2 Hz, 2H), 3.58 (t, J=5.9 Hz, 2H), 3.35 (s, 3H), 2.44 (s, 3H), 2.12 (t, J=6.0 Hz, 2H).

Embodiment 22

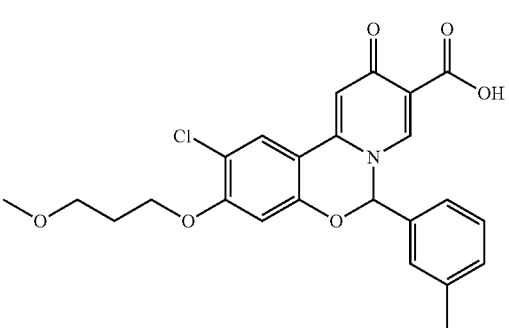 [SMILES: COCCCOc1cc2c(cc1Cl)-c1cc(=O)c(C(=O)O)cn1C(c1cccc(C)c1)O2]

$^1$H NMR (400 MHz, CDCl$_3$) δ 15.58 (br s, 1H), 8.19 (s, 1H), 7.71 (s, 1H), 7.43-7.30 (m, 2H), 7.16-7.10 (m, 2H), 7.00 (s, 1H), 6.69 (s, 1H), 6.54 (s, 1H), 4.15 (t, J=6.0 Hz, 2H), 3.59 (t, J=6.0 Hz, 2H), 3.36 (s, 3H), 2.40 (s, 3H), 2.12 (t, J=6.0 Hz, 2H).

Embodiment 23

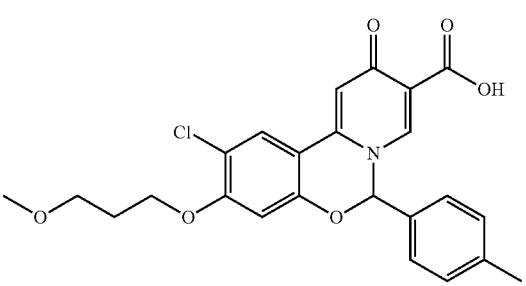

$^1$H NMR (400 MHz, CDCl$_3$) δ 15.59 (br s, 1H), 8.19 (s, 1H), 7.70 (s, 1H), 7.33-7.28 (m, 2H), 7.25-7.19 (m, 2H), 6.99 (s, 1H), 6.68 (s, 1H), 6.55 (s, 1H), 4.15 (br t, J=6.1 Hz, 2H), 3.58 (t, J=5.8 Hz, 2H), 3.35 (s, 3H), 2.41 (s, 3H), 2.14-2.09 (m, 2H).

Embodiment 24

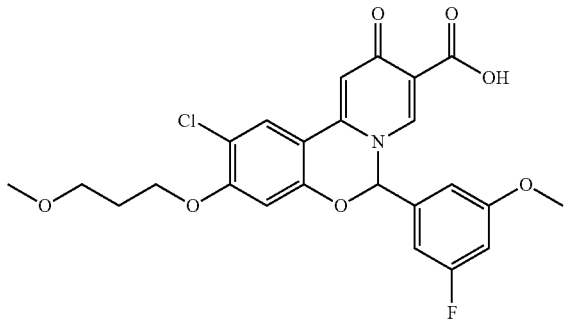

$^1$H NMR (400 MHz, CDCl$_3$) δ 15.49 (br s, 1H), 8.29 (s, 1H), 7.70 (s, 1H), 7.01 (s, 1H), 6.77-6.67 (m, 2H), 6.65-6.56 (m, 3H), 4.18 (t, J=6.2 Hz, 2H), 3.82 (s, 3H), 3.60 (t, J=5.9 Hz, 2H), 3.38 (s, 3H), 2.14 (quin, J=6.1 Hz, 2H).

Embodiments 25-34 may be obtained according to the method in embodiment 35.

Embodiment 25

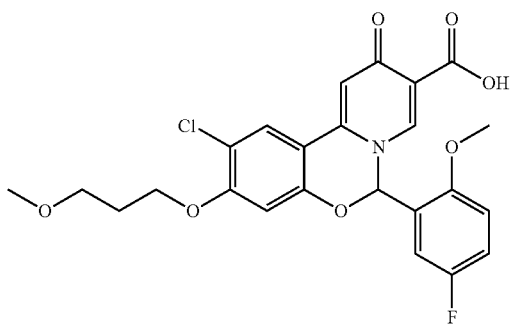

$^1$H NMR (400 MHz, CDCl$_3$) δ 15.59 (br s, 1H), 8.01 (s, 1H), 7.79 (s, 1H), 7.34-7.29 (m, 1H), 7.27 (s, 1H), 7.07 (dd, J=4.0, 9.0 Hz, 1H), 7.00 (s, 1H), 6.75 (s, 1H), 6.70 (s, 1H), 4.19 (t, J=6.2 Hz, 2H), 3.90 (s, 3H), 3.61 (t, J=5.9 Hz, 2H), 3.38 (s, 3H), 2.15 (quin, J=6.1 Hz, 2H).

Embodiment 26

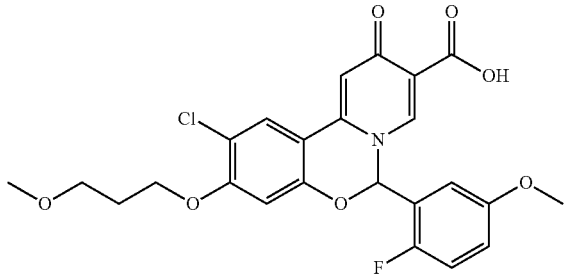

$^1$H NMR (400 MHz, CDCl$_3$) δ 15.59 (br s, 1H), 8.01 (s, 1H), 7.79 (s, 1H), 7.34-7.29 (m, 1H), 7.27 (s, 1H), 7.07 (dd, J=4.0, 9.0 Hz, 1H), 7.00 (s, 1H), 6.75 (s, 1H), 6.70 (s, 1H), 4.19 (t, J=6.2 Hz, 2H), 3.90 (s, 3H), 3.61 (t, J=5.9 Hz, 2H), 3.38 (s, 3H), 2.15 (quin, J=6.1 Hz, 2H).

Embodiment 27

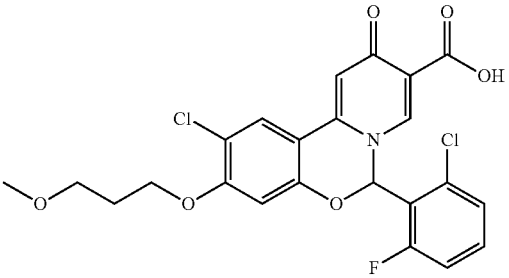

$^1$H NMR (400 MHz, CDCl$_3$) δ 7.99 (s, 1H), 7.70 (s, 1H), 7.54 (dt, J=5.9, 8.3 Hz, 1H), 7.38 (d, J=8.2 Hz, 1H), 7.19-7.13 (m, 1H), 6.95 (s, 1H), 6.87 (s, 1H), 6.63 (s, 1H), 4.14-4.04 (m, 2H), 3.51 (t, J=5.8 Hz, 2H), 3.28 (s, 3H), 2.05 (quin, J=6.0 Hz, 2H).

Embodiment 28

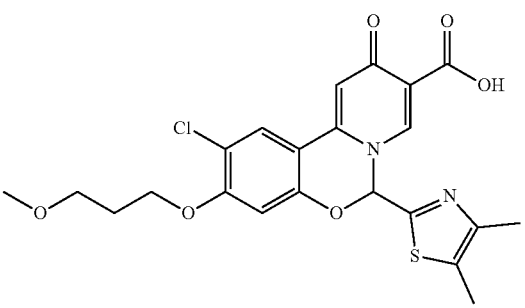

$^1$H NMR (400 MHz, CDCl$_3$) δ=15.51 (br s, 1H), 8.53 (s, 1H), 7.68 (s, 1H), 6.98-6.89 (m, 2H), 6.75 (s, 1H), 4.24-4.15 (m, 2H), 3.66-3.57 (m, 2H), 3.39 (s, 3H), 2.33 (s, 3H), 2.25 (s, 3H), 2.15 (quin, J=6.1 Hz, 2H).

Embodiment 29

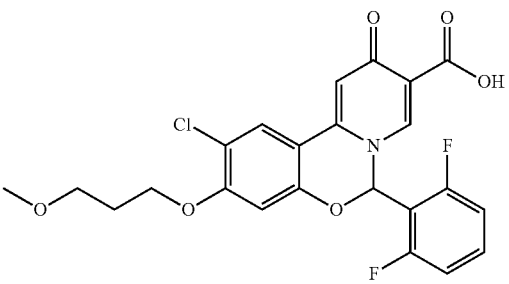

$^1$H NMR (400 MHz, CDCl$_3$) δ 8.18 (s, 1H), 7.79 (s, 1H), 7.71-7.63 (m, 1H), 7.16 (t, J=8.6 Hz, 2H), 7.03 (s, 1H), 6.83 (s, 1H), 6.71 (s, 1H), 4.22-4.12 (m, 2H), 3.63-3.62 (m, 1H), 3.60 (t, J=5.9 Hz, 1H), 3.37 (s, 3H), 2.14 (quin, J=6.1 Hz, 2H).

Embodiment 30

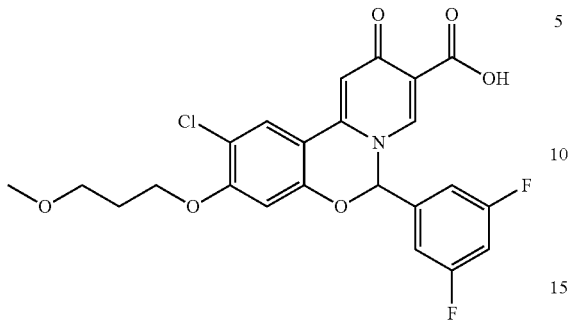

¹H NMR (400 MHz, CDCl₃) δ 15.38 (br s, 1H), 8.35 (s, 1H), 7.69 (s, 1H), 7.02 (s, 1H), 6.95 (br t, J=8.3 Hz, 1H), 6.79 (br d, J=5.0 Hz, 2H), 6.71 (s, 2H), 4.19 (t, J=6.0 Hz, 2H), 3.61 (t, J=6.0 Hz, 2H), 3.38 (s, 3H), 2.15 (t, J=6.0 Hz, 2H).

Embodiment 31

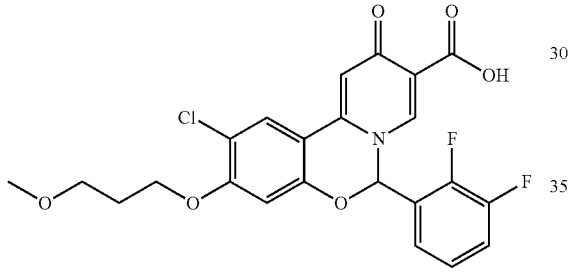

¹H NMR (400 MHz, CDCl₃) δ 15.37 (br s, 1H), 8.19 (s, 1H), 7.74 (s, 1H), 7.45-7.35 (m, 1H), 7.25-7.19 (m, 1H), 7.03 (s, 1H), 6.94 (br t, J=6.9 Hz, 1H), 6.87 (s, 1H), 6.68 (s, 1H), 4.16 (t, J=6.2 Hz, 2H), 3.58 (t, J=5.9 Hz, 2H), 3.35 (s, 3H), 2.12 (t, J=6.1 Hz, 2H).

Embodiment 32

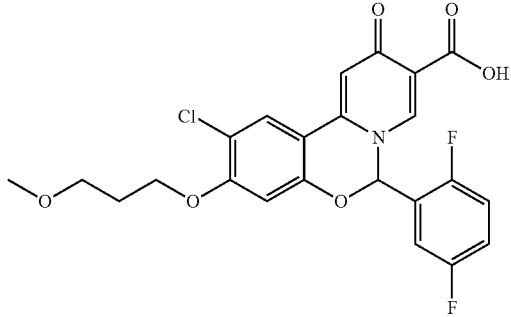 [SMILES: COCCCOc1cc2c(cc1Cl)-c1cc(=O)c(C(=O)O)cn1C(c1cc(F)ccc1F)O2]

¹H NMR (400 MHz, CDCl₃) δ 15.38 (br s, 1H), 8.14 (s, 1H), 7.76 (s, 1H), 7.29 (br s, 1H), 7.09-6.93 (m, 3H), 6.78 (s, 1H), 6.70 (s, 1H), 4.17 (t, J=6.0 Hz, 2H), 3.59 (t, J=6.0 Hz, 2H), 3.36 (s, 3H), 2.13 (t, J=6.0 Hz, 2H).

Embodiment 33

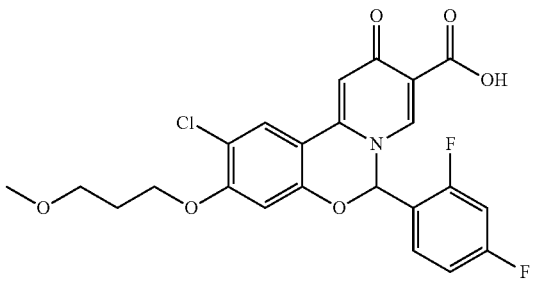 [SMILES: COCCCOc1cc2c(cc1Cl)-c1cc(=O)c(C(=O)O)cn1C(c1ccc(F)cc1F)O2]

¹H NMR (400 MHz, CDCl₃) δ 15.41 (br s, 1H), 8.13 (s, 1H), 7.75 (s, 1H), 7.30 (br d, J=6.1 Hz, 1H), 7.07-7.00 (m, 3H), 6.77 (s, 1H), 6.69 (s, 1H), 4.16 (t, J=6.2 Hz, 2H), 3.59 (t, J=5.9 Hz, 2H), 3.35 (s, 3H), 2.13 (quin, J=6.1 Hz, 2H).

Embodiment 34

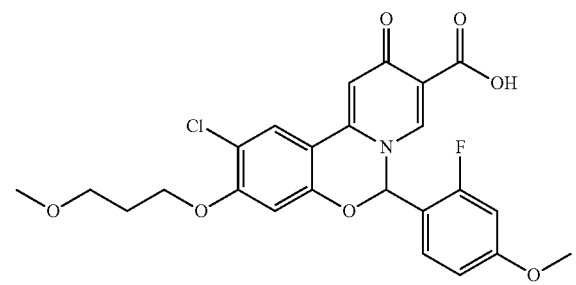

¹H NMR (400 MHz, CDCl₃) δ 15.51 (br s, 1H), 8.13 (s, 1H), 7.78 (s, 1H), 7.25-7.19 (m, 1H), 7.10 (td, J=3.8, 8.8 Hz, 1H), 7.02 (s, 1H), 6.84 (dd, J=3.1, 5.3 Hz, 1H), 6.75-6.71 (m, 1H), 6.73 (d, J=2.5 Hz, 1H), 4.18 (t, J=6.2 Hz, 2H), 3.82 (s, 3H), 3.60 (t, J=5.9 Hz, 2H), 3.37 (s, 3H), 2.14 (quin, J=6.1 Hz, 2H).

Embodiment 35

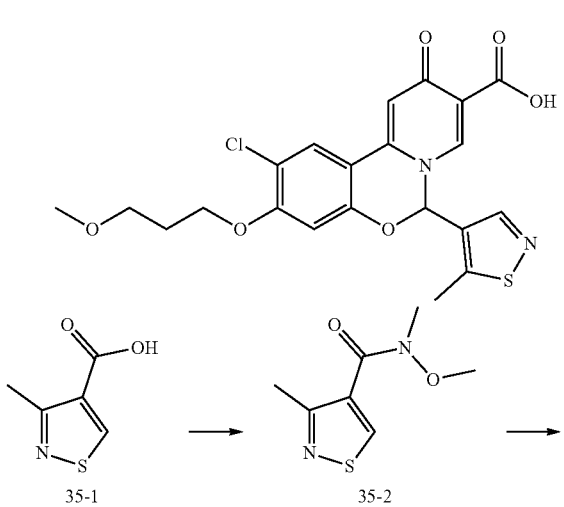

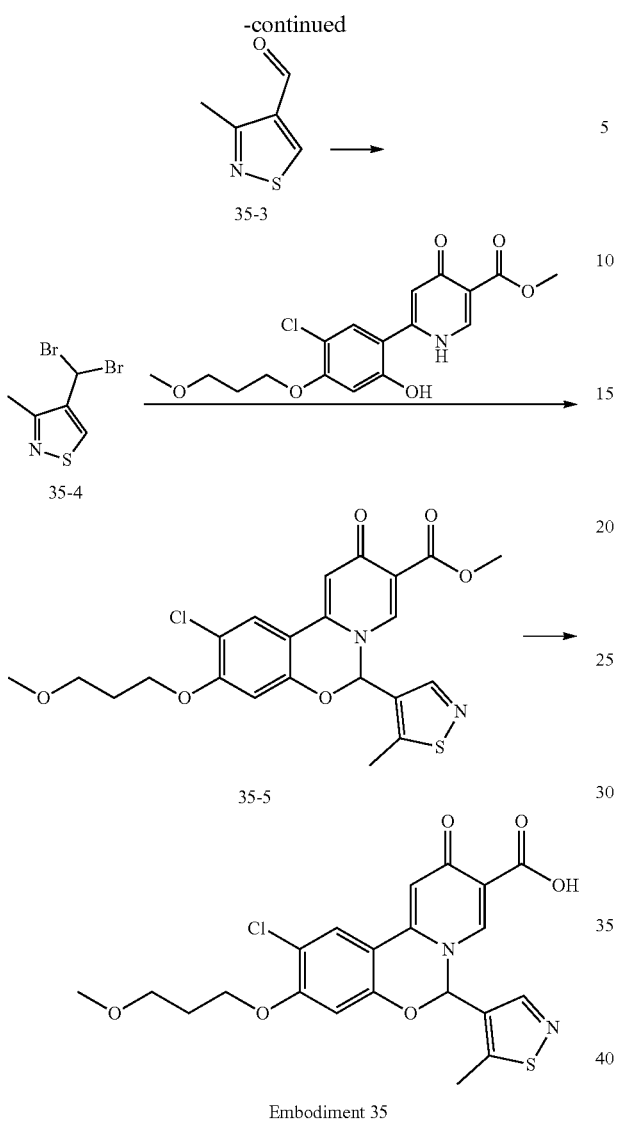

Embodiment 35

Step A: The mixture of 35-1 (20.00 g, 139.7 mmol) and HATU (79.68 g, 209.55 mmol) was dissolved in dichloromethane (250.00 mL), then triethylamine (49.48 g, 488.95 mmol, 67.78 mL) was added. The mixture was stirred at 25° C. for 10 mins, N-methoxymethylamine hydrochloride (27.25 g, 279.40 mmol) was then added. After the addition, the reaction system was charged by nitrogen for 3 times, then stirred at 25° C. for 3 hours under nitrogen atmosphere. The reaction mixture was extracted by dichloromethane (150 mL*3). The organic phase was then washed with water (250 mL*3) and saturated brine (200 mL*2), dried over anhydrous sodium sulfate, then filtered and concentrated under reduced pressure. The crude product was purified by silica gel chromatography (eluent: PE/EtOAc=1/0-1/1), giving compound 35-2.

$^1$H NMR (400 MHz, CDCl$_3$) δ 8.88 (s, 1H), 3.47 (s, 3H), 3.30 (s, 3H), 2.55 (s, 3H).

Step B: 35-2 (1.70 g, 9.13 mmol) was dissolved in dichloromethane (20.00 mL) and cooled down to −78° C. DIBAL-H (1 mol, 27.39 mL) was added dropwise at −78° C. The mixture was stirred for 2 hours. Then the mixture was quenched by adding dropwise methanol (2.2 mL) at −78° C., then stirred for 10 mins, and the dry ice acetone bath was removed. Water (1.2 mL), sodium hydroxide (4 mol, 1.2 mL) and water (3 mL) were added into the mixture. After the addition, the mixture was stirred at 25° C. for 15 mins, dried over MgSO$_4$, then filtered and concentrated under reduced pressure to give compound 35-3.

$^1$H NMR (400 MHz, CDCl$_3$) δ 10.05 (s, 1H), 9.18-9.28 (m, 1H), 2.67 (s, 3H).

Step C: Triphenyl phosphite solution (2.93 g, 9.44 mmol, 2.48 mL) was dissolved in dichloromethane (20.00 mL), liquid bromine (1.51 g) and triethylamine (1.00 g, 9.91 mmol, 1.37 mL) were added into the system at −60° C. Then 35-3 (600.00 mg, 4.72 mol) was added at −60° C. The mixture was stirred at 25° C. for 3 hours. The reaction mixture was quenched by 5 mL saturated sodium hyposulphite solution at 25° C., and then extracted by 60 mL EtOAc (20 mL*3). The organic phases were combined and washed with 90 mL saturated sodium chloride solution (30 mL*3), and dried over anhydrous sodium sulfate, filtered and concentrated under reduced pressure. The residue was purified by silica gel chromatography (eluent: PE/EtOAc=1/0) to give compound 35-4.

$^1$H NMR (400 MHz, CDCl$_3$) δ 8.86 (s, 1H), 6.73 (s, 1H), 2.58-2.68 (m, 3H).

Embodiment 35 was obtained according to the method of Step D, E in embodiment 13.

Embodiment 35: $^1$H NMR (400 MHz, CDCl$_3$) δ 15.45 (br s, 1H), 8.20-8.54 (m, 2H), 7.74 (s, 1H), 7.05 (s, 1H), 6.91 (br s, 1H), 6.63 (s, 1H), 4.16 (t, J=6.15 Hz, 2H), 3.59 (t, J=5.90 Hz, 2H), 3.37 (s, 3H), 2.67 (br s, 3H), 2.13 (quin, J=5.99 Hz, 2H).

Embodiments 36 to 40 were obtained according to the method in embodiment 35.

Embodiment 36

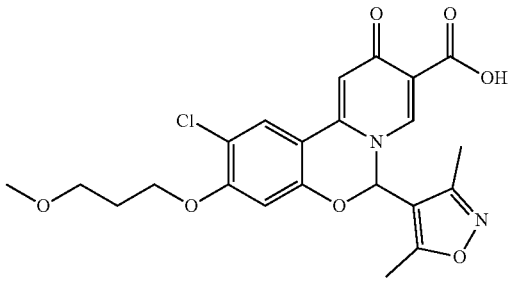 [SMILES: COCCCOc1cc2c(cc1Cl)-c1cc(=O)c(C(=O)O)cn1C(c1c(C)noc1C)O2]

$^1$H NMR (400 MHz, CDCl$_3$) δ 8.60 (s, 1H), 8.20 (s, 1H), 8.02 (s, 1H), 6.68 (s, 1H), 6.53 (s, 1H), 4.03-4.11 (m, 2H), 3.44-3.57 (m, 2H), 3.24 (s, 3H), 2.32-2.35 (m, 3H), 2.11 (s, 3H), 1.94 (t, J=6.24 Hz, 2H).

Embodiment 37

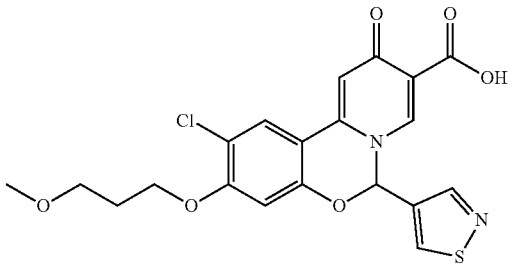 [SMILES: COCCCOc1cc2c(cc1Cl)-c1cc(=O)c(C(=O)O)cn1C(c1cnsc1)O2]

$^1$H NMR (400 MHz, CDCl$_3$) δ 15.36 (br s, 1H), 8.60-8.41 (m, 3H), 7.70 (s, 1H), 7.02 (s, 1H), 6.70 (s, 1H), 4.18 (br t, J=6.1 Hz, 2H), 3.60 (br t, J=5.6 Hz, 2H), 3.51 (s, 3H), 2.17-2.13 (m, 2H).

Embodiment 38

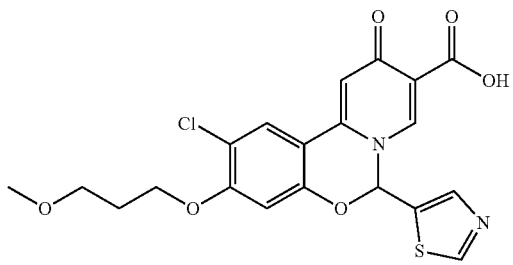 [SMILES: COCCCOc1cc2c(cc1Cl)-c1cc(=O)c(C(=O)O)cn1C(c1cncs1)O2]

$^1$H NMR (400 MHz, CDCl$_3$) δ 15.34 (br s, 1H), 8.89 (br s, 1H), 8.50 (br s, 1H), 7.81 (br s, 1H), 7.70 (s, 1H), 7.14 (br s, 1H), 7.00 (s, 1H), 6.67 (br s, 1H), 4.16 (br t, J=5.77 Hz, 2H), 3.58 (br t, J=5.83 Hz, 2H), 3.35 (s, 3H), 2.09-2.14 (m, 2H)

Embodiment 39 (39_A and 39_B)

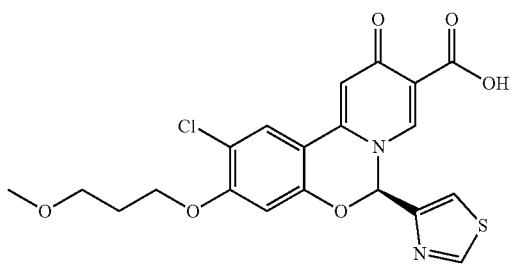

embodiment 39_A or 39_B

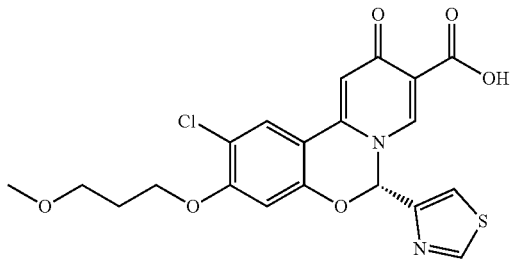

embodiment 39_B or 39_A

The pre-hydrolysis compound of embodiment 39 was separated by chiral HPLC column (column: AD (250 mm*30 mm, 10 μm); mobile phase: [0.1% NH$_3$H$_2$O EtOH]; elution gradient: 60%-60%, 4.12 min; 220 min) to give the isomers with two configurations, which were hydrolyzed to give embodiment 39_A (t=1.594 min), ee value (enantiomeric excess):100% and embodiment 39_B (t=2.593 min), ee value (enantiomeric excess): 98%. SFC (supercritical fluid chromatography) method: AD-3S_4_40_3ML. Column: Chiralpak AD-3 100×4.6 mm I.D., 3 μm Mobile phase: 40% iso-propanol (0.05% DEA) in CO$_2$. Flow rate: 3 mL/min. Wavelength: 220 nm.

Embodiment 39_A $^1$H NMR (400 MHz, CDCl$_3$) δ 15.48 (s, 1H), 8.82 (d, J=1.88 Hz, 1H), 8.48 (s, 1H), 7.66 (s, 1H), 7.39 (d, J=1.63 Hz, 1H), 6.95 (s, 1H), 6.92 (s, 1H), 6.73 (s, 1H), 4.17 (t, J=6.21 Hz, 2H), 3.59 (dt, J=2.20, 5.87 Hz, 2H), 3.36 (s, 3H), 2.13 (quin, J=6.05 Hz, 2H).

Embodiment 39_B $^1$H NMR (400 MHz, CDCl$_3$) δ 15.50 (br s, 1H), 8.81 (d, J=1.51 Hz, 1H), 8.49 (s, 1H), 7.66 (s, 1H), 7.39 (s, 1H), 6.88-7.00 (m, 2H), 6.73 (s, 1H), 4.17 (br t, J=6.21 Hz, 2H), 3.53-3.66 (m, 2H), 3.36 (s, 3H), 2.13 (quin, J=5.99 Hz, 2H).

Embodiment 40 (40_A and 40_B)

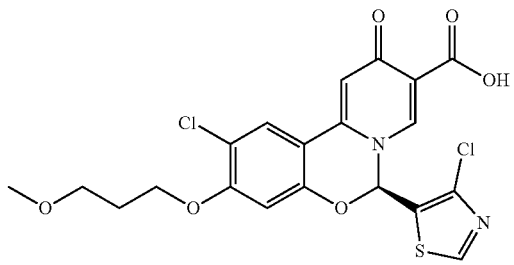

embodiment 40_A or 40_B

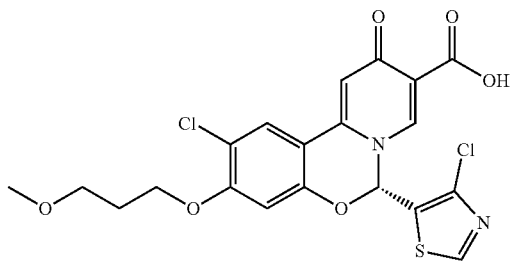

embodiment 40_B or 40_A

Embodiment 40 was separated by HPLC (column: AD (250 mm*30 mm, 10 μm); mobile phase: [0.1% NH$_3$H$_2$O IPA]: 45%-45% in CO$_2$, 2 min; 1000 min) to give the isomers with two configurations, embodiment 40_A (t=1.540 min), ee value (enantiomeric excess): 96.4% and embodiment 40_B (t=2.067 min), ee value (enantiomeric excess): 93.5%.

Embodiment 40_A: $^1$H NMR (400 MHz, CD$_3$CD) δ 9.02 (s, 1H), 8.65 (br s, 1H), 8.41 (s, 1H), 8.08 (br s, 1H), 7.67 (s, 1H), 7.17 (br s, 1H), 6.95 (s, 1H), 4.58 (br s, 3H), 4.21 (br t, J=5.9 Hz, 2H), 3.61 (t, J=6.1 Hz, 2H), 2.12-2.07 (m, 2H).

Embodiment 40_B: $^1$H NMR (400 MHz, CD$_3$CD) δ 9.02 (s, 1H), 8.66 (s, 1H), 8.42 (s, 1H), 8.09 (br s, 1H), 7.67 (s, 1H), 7.20 (br s, 1H), 6.97-6.93 (m, 1H), 6.95 (s, 1H), 4.58 (br s, 3H), 4.21 (br t, J=6.2 Hz, 2H), 3.61 (t, J=6.0 Hz, 2H), 2.10 (br t, J=6.1 Hz, 2H).

Embodiment 41

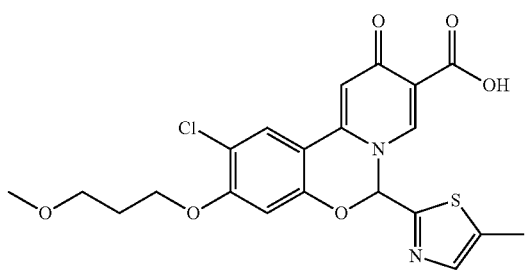

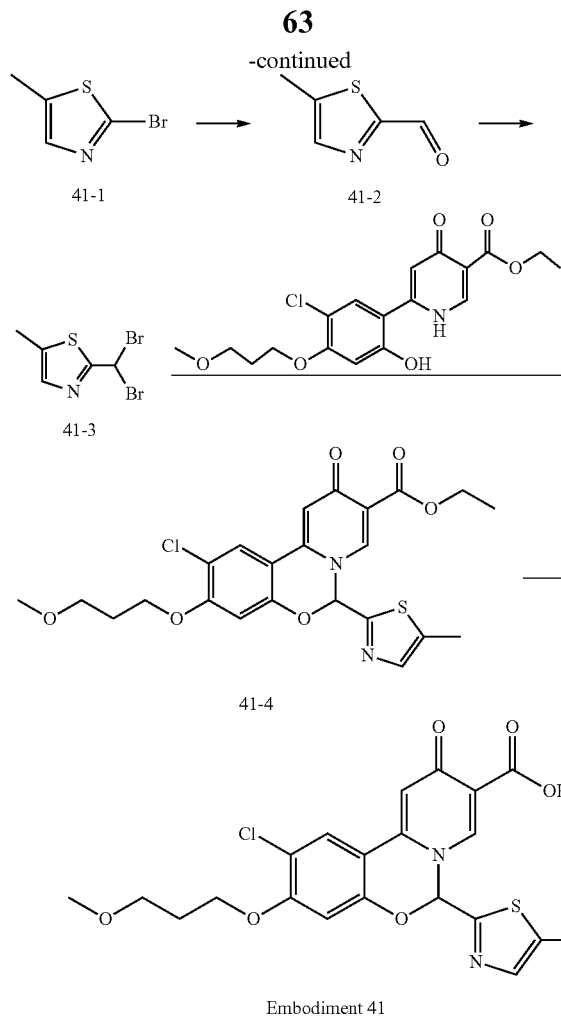

Embodiment 41

Step A: 41-1 (2.00 g, 11.23 mmol) was dissolved in tetrahydrofuran (120 mL), then cooled down to −60° C. n-Butyllithium (2.5 mol/L, 4.72 mL) was slowly added dropwise at −60° C., and then N,N-dimethylformamide (1.30 mL, 16.85 mmol) was added, the reaction was stirred at −60° C. for 1 hours, and then heated to 25° C. and stirred for 3 hours. The reaction was quenched by water, and then extracted by dichloromethane (50 mL*3), the organic phase was washed with saturated brine (35 mL*2), dried over anhydrous sodium sulfate, then filtered and concentrated in vacuum to give the compound 41-2.

$^1$H NMR (400 MHz, CDCl$_3$):δ 9.78 (s, 1H), 7.68 (s, 1H), 2.49 (d, J=1.0 Hz, 3H).

Step B: Triphenyl phosphite (52.22 g, 168.3 mmol) was dissolved in dichloromethane (300 mL) and then cooled down to −60° C. Bromine (8.67 mL, 168.3 mmol) was slowly added dropwise at 0° C., then triethylamine (18.73 g, 185.13 mmol, 25.66 mL) and 41-2 (10.7 g, 84.15 mmol) were added into the reaction sequentially, the reaction mixture was stirred at −60° C. for 1 hours, and then the cooling bath was removed, the reaction was stirred at 25° C. for further 3 hours. The reaction was quenched by water, and extracted by dichloromethane (500 mL*3), the organic phase was washed saturated brine (350 mL*2), dried over anhydrous sodium sulfate, then filtered and concentrated in vacuum. The product was purified by chromatography (silicon dioxide, PE:EtOAc=100:0) to give compound 41-3.

$^1$H NMR (400 MHz, CDCl$_3$) δ 7.25 (s, 1H), 6.85 (s, 1H), 2.49 (s, 3H).

Step C: 41-3 (3.52 g, 9.23 mmol) and 41-3 (5.00 g, 18.45 mmol) were dissolved in N,N-dimethylformamide (15 mL), then potassium carbonate (7.01 g, 50.74 mmol) was added. The mixture was stirred at 100° C. for 16 hours. The reaction was quenched by water, and then extracted by dichloromethane (50.00 mL*3), the organic phase was washed with brine (35.00 mL*2), dried over anhydrous sodium sulfate, then filtered and concentrated in vacuum. The product was purified by chromatography (silicon dioxide, PE:EtOAc=0:100) to compound 41-4.

Step D: 41-4 (300.00 mg, 611.05 μmol) was dissolved in methanol (6.00 mL), then sodium hydroxide solution (4.00 mol/L, 611.05 μL) was added, the mixture was stirred at 25° C. for 0.5 hours. The reaction mixture was concentrated in vacuum, then N,N-dimethylformamide (2.00 mL) was added, and adjusted by formic acid to pH=3-4, the resulting mixture was purified by preparative HPLC to give embodiment 41.

$^1$HNMR (400 MHz, CDCl$_3$) δ 15.45 (br s, 1H), 8.55 (s, 1H), 7.67 (s, 1H), 7.39 (s, 1H), 6.98 (s, 2H), 6.75 (s, 1H), 4.25-4.16 (m, 2H), 3.66-3.57 (m, 2H), 3.39 (s, 3H), 2.47 (s, 3H), 2.16 (quin, J=6.1 Hz, 2H).

Embodiments 42 and 43 may be obtained according to the method in embodiment 41.

Embodiment 42

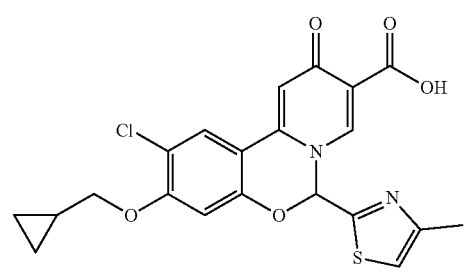 [SMILES: Cc1csc(C2Oc3cc(OCC4CC4)c(Cl)cc3-c3cc(=O)c(C(=O)O)cn32)n1]

$^1$H NMR (400 MHz, CDCl$_3$) δ 15.46 (br s, 1H), 8.55 (s, 1H), 7.68 (s, 1H), 7.01-6.96 (m, 3H), 6.71 (s, 1H), 3.97 (d, J=6.8 Hz, 2H), 2.38 (s, 3H), 1.41-1.30 (m, 1H), 0.77-0.71 (m, 2H), 0.47-0.42 (m, 2H).

Embodiment 43

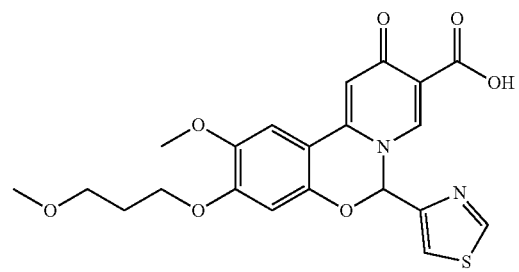 [SMILES: COCCCOc1cc2c(cc1OC)-c1cc(=O)c(C(=O)O)cn1C(c1cscn1)O2]

$^1$H NMR (400 MHz, CDCl$_3$): δ 15.62 (br s, 1H), 8.83 (br s, 1H), 8.45 (br s, 1H), 7.40 (br s, 1H), 7.01 (br s, 1H), 6.95 (br s, 1H), 6.87 (br s, 1H), 6.70 (br s, 1H), 4.16 (br s, 2H), 3.88 (br s, 3H), 3.56 (br s, 2H), 3.35 (br s, 3H), 2.13 (br s, 2H).

Embodiment 44

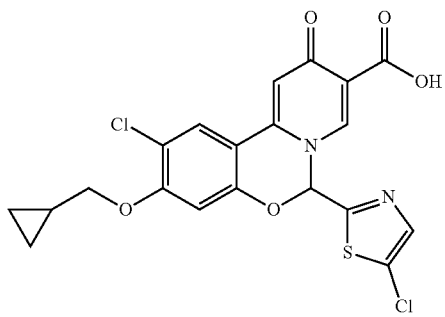

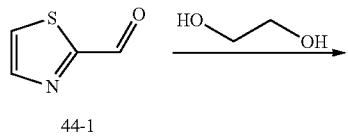

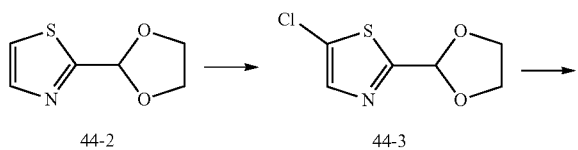

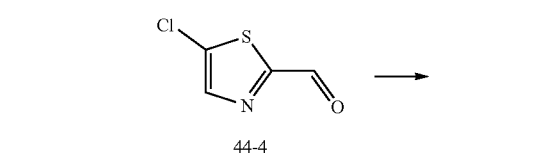

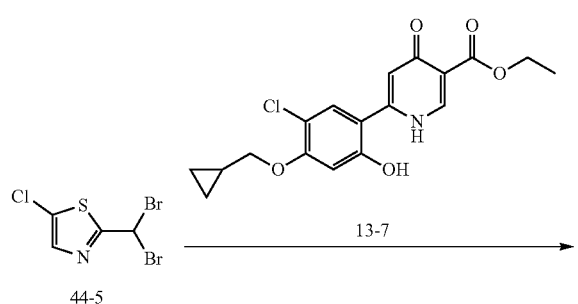

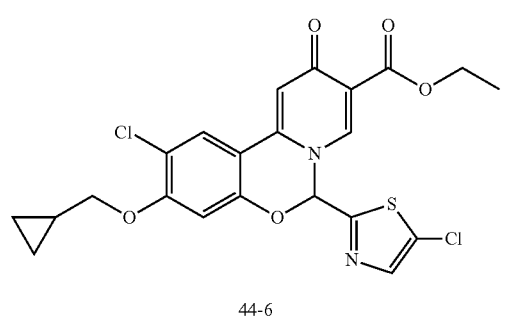

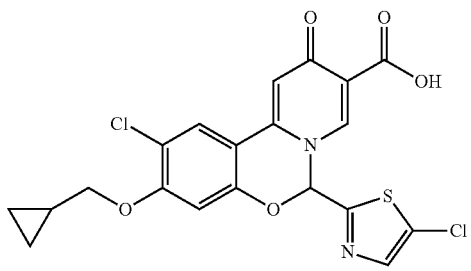

Embodiment 44

Step A: 44-1 (25.00 g, 220.97 mmol) was dissolved in toluene (250.00 mL), then p-toluenesulfonic acid monohydrate (12.61 g, 66.29 mmol) and glycol (41.15 g, 662.91 mmol) were added. The mixture was stirred at 130° C. for 16 hours using a water separator. Then 50 mL saturated sodium bicarbonate solution and 450 mL (150 m L*3) methyl tert-butyl ether were used. The organic phase was washed with 300 mL saturated brine (100 mL*3), dried over sodium sulfate, then filtered and concentrated under reduced pressure giving 44-2.

$^1$HNMR (400 MHz, CDCl$_3$) δ7.76 (d, J=3.2 Hz, 1H), 7.31 (d, J=3.2 Hz, 1H), 6.10 (s, 1H), 4.11-4.00 (m, 4H).

Step B: 44-2 (24.60 g, 156.50 mmol) was dissolved in tetrahydrofuran (615.00 mL) and cooled down to −78° C., N-butyllithium (2.5 mol, 75.12 mL) was slowly added dropwise into the solution, then stirred for 30 mins after addition, and then tetrachloromethane (75.40 mL) was added, the reaction mixture was stirred at 0° C. for 1 hours. The reaction was quenched by 100 mL saturated ammonium chloride, and extracted by water 100 mL and EtOAc 600 mL (200 mL*3), dried over sodium sulfate, then filtered and concentrated under reduced pressure, the residue was purified by silica gel chromatography (eluent: PE/EtOAc=1/0-10/1), giving 44-3.

$^1$HNMR (400 MHz, CDCl$_3$) δ=7.62 (s, 1H), 6.03 (s, 1H), 4.16-4.07 (m, 4H).

Step C: 44-3 (13.30 g, 69.40 mmol) was dissolved in tetrahydrofuran (37.00 mL), hydrochloric acid (1 mol, 36.78 mL) was added thereto. The mixture was stirred for 3 hours at 75° C. The reaction mixture was neutralized by saturated sodium bicarbonate, and extracted by 50 mL water and 600 mL EtOAc (200 mL*3). The organic phases were combined and dried over anhydrous sodium sulfate, then filtered and concentrated under reduced pressure, the residue was purified by silica gel chromatography (eluent: PE/EtOAc=30/1-20/1), giving 44-4.

Embodiment 44 was obtained according to the method of Step D, E, F in embodiment 13.

Embodiment 44: $^1$H NMR (400 MHz, DMSO-d6) δ 8.97 (br s, 1H), 8.32 (s, 1H), 8.30-8.24 (m, 1H), 8.27 (br s, 1H), 7.94 (s, 1H), 7.82 (s, 1H), 7.48 (br s, 1H), 7.12 (s, 1H), 4.04 (br dd, J=7.2, 11.6 Hz, 2H), 1.25 (br d, J=8.4 Hz, 1H), 0.61 (br d, J=7.9 Hz, 2H), 0.38 (br s, 2H).

Embodiment 45 (45_A and 45_B)
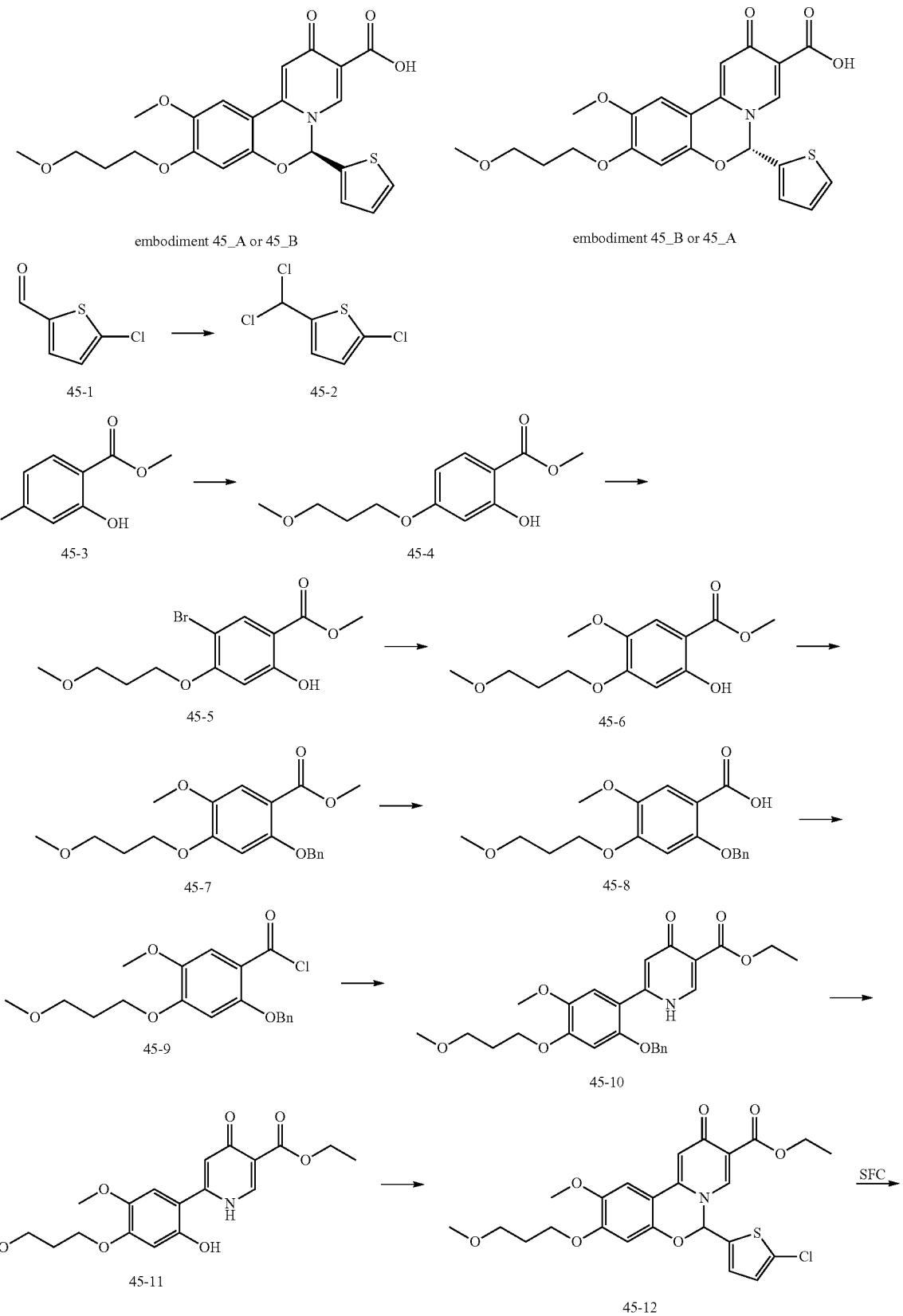

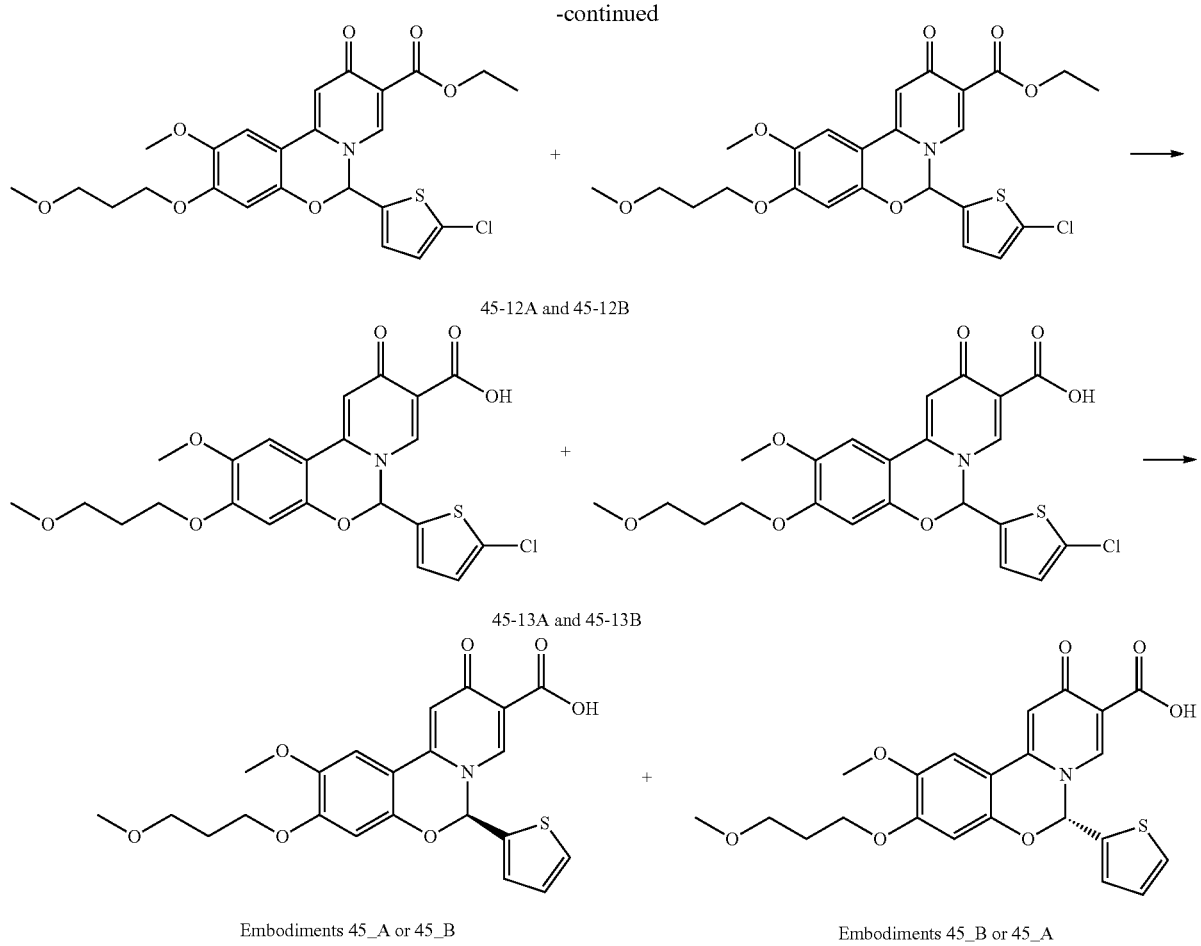

45-12A and 45-12B 45-13A and 45-13B

Embodiments 45_A or 45_B     Embodiments 45_B or 45_A

Step A: 45-1 (18.12 mL, 170.53 mmol) was dissolved in dichloromethane (425.00 mL), then pyridine (2.76 mL, 34.11 mmol) was added at −10° C., and then phosphorus pentachloride (35.51 g, 170.53 mmol) was added in one time. The reaction mixture was stirred at −10° C. for 1 hour, and then sodium dicarbonate (42.98 g, 511.59 mmol) was added. The mixture was stirred at −10° C. for 0.25 hours. The reaction mixture was filtered, the filtrate was dried over anhydrous magnesium sulfate, filtered, and the filtrate was then concentrated under reduced pressure and evaporated to dryness, giving 45-2.

$^1$H NMR (400 MHz, CDCl$_3$) δ 7.02 (d, J=3.9 Hz, 1H), 6.87 (s, 1H), 6.80 (d, J=4.0 Hz, 1H).

Step B: 45-3 (50.00 g, 297.35 mmol), potassium carbonate (41.10 g, 297.35 mmol) were dissolved in N,N-dimethylformamide (250.00 mL), 1-bromo-3-methoxypropane (45.50 g, 297.35 mmol) was dissolved in N,N-dimethylformamide (150.00 mL) and was added dropwise into the system above at 90° C. in hour. The reaction mixture was stirred at 90° C. for 0.5 hours. Water (500 mL) was added, then extracted by EtOAc (500 mL*2), the organic phases were combined and washed with water (1000 mL*3) and brine (500 mL), dried over anhydrous sodium sulfate, then filtered and concentrated under reduced pressure. The residue was purified by a silica gel column (eluent: PE/EtOAc=1/0), giving 45-4.

Step C: Liquid bromine (9.44 mL, 183.14 mmol) was dissolved in chloroform (150 mL) and was added dropwise into 45-4 (40.00 g, 166.49 mmol) in chloroform solution (570 mL) at 0° C., the system was stirred at 25° C. for 0.5 hours. After concentration under reduced pressure and evaporation to dryness, the residue was purified by a silica gel column (eluent: PE/EtOAc=1/0-50/1), giving 45-5.

Step D: The sheared sodium metal (10.50 g, 456.84 mmol) was added in batches under nitrogen atmosphere into anhydrous methanol (250.00 mL), the system was stirred at 50° C. for 3 hours. The system was added into the system of 45-5 (45.00 g, 114.21 mmol) and copper chloride (7.68 g, 57.10 mmol) in N,N-dimethylformamide (225.00 mL) in one time at 25° C., the reaction mixture was stirred at 110° C. for 16 hours under nitrogen atmosphere. The reaction mixture was quenched by 6 mol/L hydrochloric acid (180 mL), and extracted by EtOAc (500 mL*2), the organic phases were combined, washed with water (500 mL*2) and brine (400 mL), dried over anhydrous sodium sulfate, then filtered and concentrated under reduced pressure. The residue was purified by a silica gel column (eluent: PE/EtOAc=50/1-10/1), giving 45-6.

Step E: 45-6 (17.00 g, 62.90 mmol) was dissolved in N,N-dimethylformamide (100.00 mL), potassium carbonate (13.04 g, 94.35 mmol) and benzyl bromide (11.83 g, 69.19 mmol, 8.22 mL) were added. The system was stirred at 25° C. for 16 hours. Then water (200 mL*3) was added and extracted by EtOAc (200 mL*2), the organic phases were combined and washed with water (200 mL*2) and brine (200 mL), dried over anhydrous sodium sulfate, then filtered and concentrated under reduced pressure, giving 45-7.

Step F: 45-7 (22.79 g, 63.24 mmol) was dissolved in methanol (60.00 mL) and tetrahydrofuran (60.00 mL), potassium hydroxide solution (6 mol/L, 61.55 mL) was added, then stirred at 45° C. for 2 hours. The reaction mixture was adjusted by 1 mol/L hydrochloric acid to pH=3-4, the suspension was filtered to give the residue. The residue was used PE/EtOAc=10/1 (50 mL), then filtered, concentrated under reduced pressure and dried, giving 45-8.

$^1$H NMR (400 MHz, CDCl$_3$) δ 10.85 (br s, 1H), 7.64 (s, 1H), 7.48-7.39 (m, 5H), 6.71 (s, 1H), 5.27 (s, 2H), 4.17 (t, J=6.5 Hz, 2H), 3.89 (s, 3H), 3.58 (t, J=5.9 Hz, 2H), 3.38 (s, 3H), 2.13 (quin, J=6.2 Hz, 2H).

Step G: 45-8 (20.00 g, 57.74 mmol) was dissolved in dichloromethane (200.00 mL), then oxalyl chloride (7.58 mL, 86.61 mmol) and N,N-dimethylformamide (4.44 μL, 57.74 μmol) were added. The system was stirred at 25° C. for 2 hours, concentrated under reduced pressure and evaporated to dryness to give compound 45-9.

Step H: 45-9 (21.06 g, 57.73 mmol) and ethyl 2-acetyl-3-dimethylaminoacrylate (13.90 g, 75.05 mmol) were dissolved in tetrahydrofuran (200.00 mL) and the mixture was added dropwise into lithium hexamethyldisilazide (1 mol/L, 150.00 mL) at −70 to −60° C. After the addition, acetic acid (115.55 mL, 2.02 mol/L) and ammonium acetate (5.78 g, 75.05 mmol) were added. The system was stirred at 65° C. for 1 hour. After saturated sodium bicarbonate solution (1000 mL) was added, the mixture was then extracted by EtOAc (200 mL), the organic phase was washed with water (200 mL) and brine (100 mL), dried over anhydrous sodium sulfate and filtered, then concentrated under reduced pressure to dryness. The residue was washed with MTBE (50 mL) and filtered to give compound 45-10.

$^1$H NMR (300 MHz, CDCl$_3$) δ 11.03 (s, 1H), 9.02 (s, 1H), 7.71 (s, 1H), 7.64 (s, 1H), 7.46-7.31 (m, 5H), 6.69 (s, 1H), 5.11 (s, 2H), 4.48 (q, J=7.2 Hz, 2H), 4.14 (t, J=6.6 Hz, 2H), 3.93 (s, 3H), 3.58 (t, J=5.9 Hz, 2H), 3.38 (s, 3H), 2.11 (quin, J=6.3 Hz, 2H), 1.46 (t, J=7.1 Hz, 3H).

Step I: 45-10 (20.00 g, 42.78 mmol) was dissolved in tetrahydrofuran (250.00 mL), and palladium on carbon (10%, 1 g) was added under nitrogen atmosphere, the system was charged by hydrogen in vacuum 3 times, then stirred at 25° C. for 16 hours under hydrogen atmosphere (15 Psi). After filtration, the filtrate was concentrated under reduced pressure to give compound 45-11.

$^1$H NMR (400 MHz, CDCl$_3$) δ 14.24 (br s, 1H), 11.27 (s, 1H), 8.86 (s, 1H), 7.23 (s, 1H), 7.16 (s, 1H), 6.56 (s, 1H), 4.49 (q, J=7.1 Hz, 2H), 4.17 (t, J=6.5 Hz, 2H), 3.90 (s, 3H), 3.59 (t, J=6.1 Hz, 2H), 3.38 (s, 3H), 2.15 (quin, J=6.3 Hz, 2H), 1.47 (t, J=7.2 Hz, 3H).

Step J: 45-11 (5.00 g, 13.25 mmol) was dissolved in dimethyl sulfoxide (50.00 mL), then cesium carbonate (17.27 g, 53.00 mmol) and 2-chloro-5-(dichloromethyl)thiophene (13.35 g, 66.25 mmol) were added. The system was stirred at 100° C. for 16 hours. The reaction mixture was diluted by water (100 mL), then extracted by dichloromethane (100 mL), the organic phase was washed with water (100 mL*2) and saturated brine (100 mL), dried over anhydrous sodium sulfate, then filtered and evaporated under reduced pressure to dryness. The residue was purified by a silica gel column (eluent: PE/EtOAc=10/1-1/1 to dichloromethane/ethanol=100/1-30/1) to give compound 45-12.

Step K: 45-12 (200.00 mg, 395.28 μmol) was purified by chiral HPLC (column: OJ (250 mm*30 mm, 10 m); mobile phase: [0.1% NH$_3$H$_2$O MeOH]; elution gradient: 30%-30%, 2.3 min; 90 min) to give embodiment 45-12A (t=2.194 min) and 45-12B (t=2.544 min).

Step L: Embodiment 45-12A (71.00 mg, 140.32 mmol) was dissolved in tetrahydrofuran (2.00 mL) and methanol (2.00 mL), then sodium hydroxide solution (4 mol/L, 1.00 mL) was added, the system was stirred at 25° C. for 0.5 hours. The reaction mixture was adjusted by 1 mol/L hydrochloric acid to pH=3, and extracted by dichloromethane (20 mL*2), the organic phases were combined and dried over anhydrous sodium sulfate, then filtered and concentrated under reduced pressure, giving embodiment 45_13A.

Step M: Embodiment 45_13A (65.00 mg, 136.01 mmol) was dissolved in tetrahydrofuran (15.00 mL), palladium on carbon (10%, 30 mg) was added under nitrogen atmosphere, the suspension was charged with hydrogen for several times, the system was stirred at 25° C. for 16 hours under hydrogen atmosphere (15 Psi). The reaction mixture was filtered, the filtrate was concentrated under reduced pressure to dryness, the residue was purified by silica gel plate (silicon dioxide, dichloromethane/methanol=15:1), giving embodiment 45_A (t=1.941 min), ee value (enantiomeric excess): 100%.

Method of determination for the ee value (enantiomeric excess): OD-3S_3_40_3ML Column: Chiralcel OD-3 100× 4.6 mm I.D., 3 μm Mobile phase: 40% methanol (0.05% DEA) in CO$_2$ Flow rate: 3 mL/min Wavelength: 220 nm.

Embodiment 45_B (t=3.040 min), ee value (enantiomeric excess): 100%.

Embodiment 45_A: $^1$H NMR (400 MHz, CDCl$_3$) δ 15.66 (br s, 1H), 8.41 (br s, 1H), 7.48 (d, J=4.9 Hz, 1H), 7.09-7.03 (m, 3H), 7.01 (s, 1H), 6.97-6.93 (m, 1H), 6.67 (s, 1H), 4.16 (t, J=6.5 Hz, 2H), 3.92 (s, 3H), 3.57 (t, J=5.9 Hz, 2H), 3.37 (s, 3H), 2.14 (quin, J=6.2 Hz, 1H), 2.18-2.11 (m, 1H).

Embodiment 45_B: $^1$H NMR (400 MHz, CDCl$_3$) δ 15.63 (br s, 1H), 8.37 (br s, 1H), 7.49 (br d, J=4.4 Hz, 1H), 7.06 (br s, 3H), 7.00 (s, 1H), 6.91 (br s, 1H), 6.68 (s, 1H), 4.16 (t, J=6.5 Hz, 2H), 3.93 (s, 3H), 3.57 (t, J=5.9 Hz, 2H), 3.37 (s, 3H), 2.15 (quin, J=6.2 Hz, 2H).

Embodiment 46 to embodiment 48 may be obtained according to the method in embodiment 45.

Embodiment 46 (46_A and 46_B)

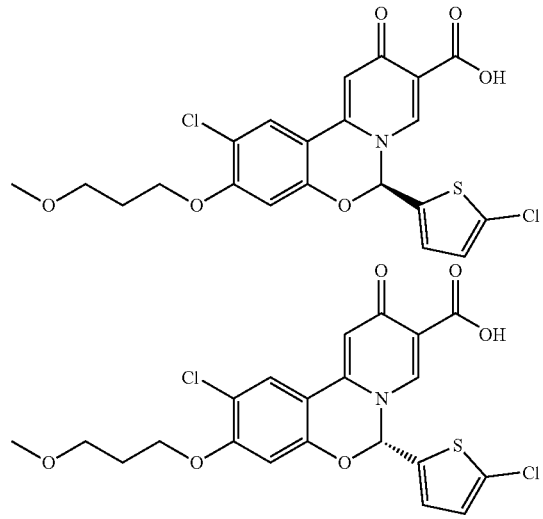

The pre-hydrolysis compound of embodiment 46 was separated by chiral HPLC (column: OJ (250 mm*30 mm, 10 m); mobile phase: [0.1% NH$_3$H$_2$O-MeOH]; elution gradient: 30%-30%, 3 min; 40 min) to give isomers with two configurations, t=2.592 min and t=2.829 min. After hydrolysis, embodiment 46_A (t=2.396 min), ee value (enantiomeric excess): 95.7% and embodiment 46_B (t=2.887 min), ee value (enantiomeric excess): 100%, were obtained respectively. Methods for determination of ee value (enantiomeric excess): OD-3S_3_40_3ML Column: Chiralcel OD-3 100×4.6 mm I. D., 3 m Mobile phase: 40% methanol (0.05% DEA) in $CO_2$. Flow rate: 3 mL/min Wavelength: 220 nm.

Embodiment 46_A: $^1$H NMR (400 MHz, $CDCl_3$) δ 15.42 (br s, 1H), 8.50-8.44 (m, 1H), 7.62 (s, 1H), 6.91 (s, 2H), 6.74 (d, J=3.8 Hz, 1H), 6.69 (d, J=3.5 Hz, 1H), 6.61 (s, 1H), 4.10 (br t, J=6.0 Hz, 2H), 3.52 (t, J=5.8 Hz, 2H), 3.29 (s, 3H), 2.06 (quin, J=6.0 Hz, 2H).

Embodiment 46_B: $^1$H NMR (400 MHz, $CDCl_3$) δ 15.44 (br s, 1H), 8.49 (s, 1H), 7.62 (s, 1H), 6.93 (s, 1H), 6.91 (s, 1H), 6.75-6.72 (m, 1H), 6.70 (d, J=3.8 Hz, 1H), 6.61 (s, 1H), 4.14-4.07 (m, 2H), 3.52 (t, J=5.9 Hz, 2H), 3.29 (s, 3H), 2.06 (quin, J=6.1 Hz, 2H).

Embodiment 47 (47_A and 47_B)

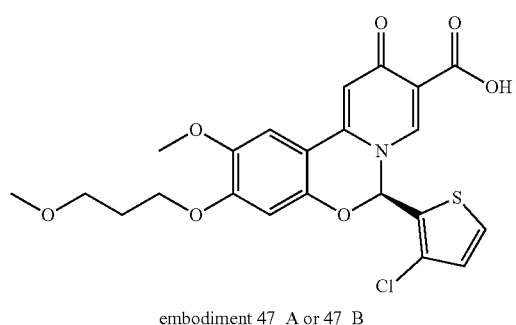

embodiment 47_A or 47_B

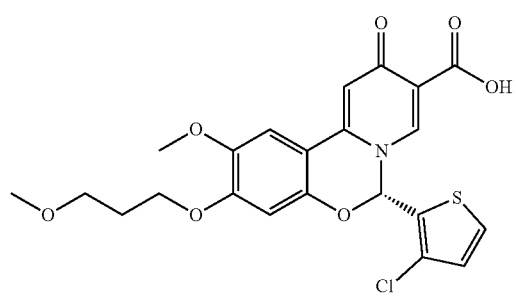

embodiment 47_B or 47_A

The pre-hydrolysis compound of embodiment 47 was separated by chiral HPLC (column: AS (250 mm*30 mm, 10 m); mobile phase: [0.1% $NH_3H_2O$-MeOH]; elution gradient: 45%-45%, 2.3 min; 90 min) to give the isomers with two configurations, (t=2.110 min) and (t=2.574 min), after hydrolysis, the embodiment 47_A (t=2.705 min), ee value (enantiomeric excess): 99% and embodiment 47_B (t=1.818 min), ee value (enantiomeric excess): 100% were obtained respectively. Method of ee value determination (enantiomeric excess): OD-3S_3_40_3ML Column: Chiralcel OD-3 100×4.6 mm I.D., 3 μm Mobile phase: 40% methanol (0.05% DEA) in $CO_2$ Flow rate: 3 mL/min Wavelength: 220 nm.

Embodiment 48

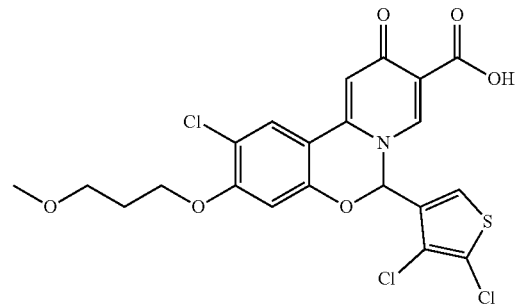 [SMILES: COCCCOc1cc2c(cc1Cl)-c1cc(=O)c(C(=O)O)cn1C(c1csc(Cl)c1Cl)O2]

$^1$H NMR (400 MHz, DMSO-d6) δ 8.88 (br s, 1H), 8.29 (br d, J=7.8 Hz, 1H), 7.62-7.44 (m, 2H), 7.25 (s, 1H), 6.91 (s, 1H), 4.15 (br t, J=6.1 Hz, 2H), 3.48 (br s, 2H), 3.23 (s, 3H), 1.96 (quin, J=6.2 Hz, 2H).

Embodiment 49 (49_A and 49_B)

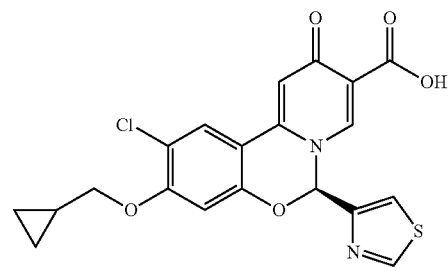

embodiment 49_A or 49_B

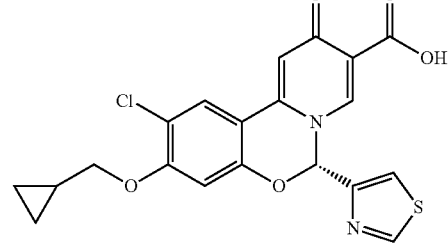

embodiment 49_B or 49_A

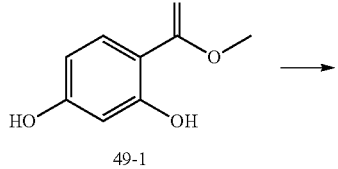

49-1

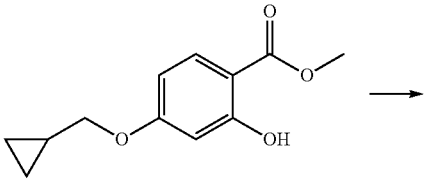

49-2

-continued

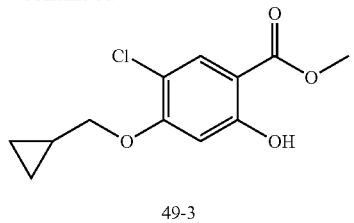

49-3

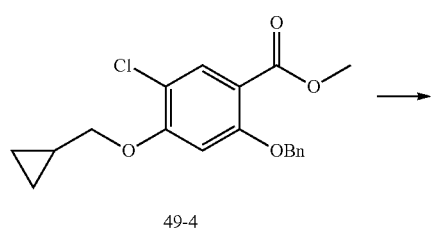

49-4

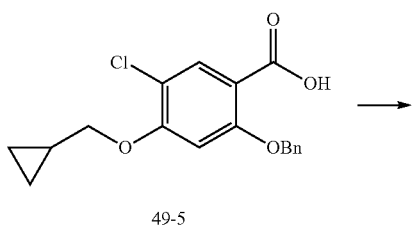

49-5

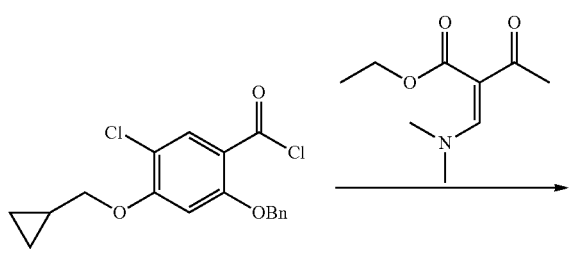

49-6

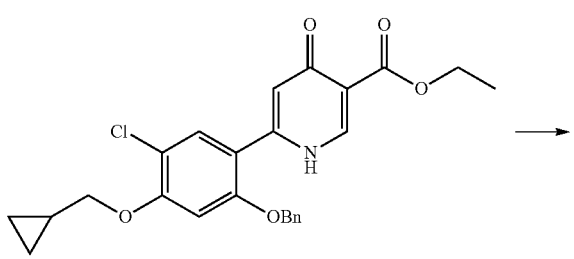

49-7

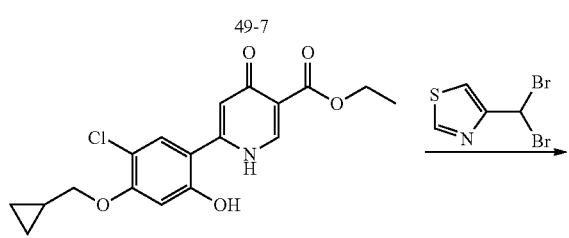

49-8

-continued

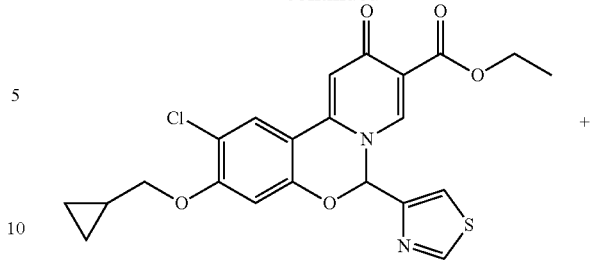

49_9A

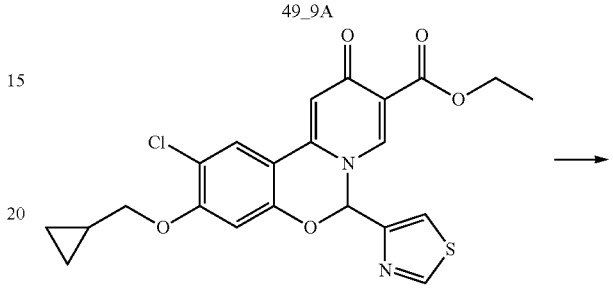

49_9B

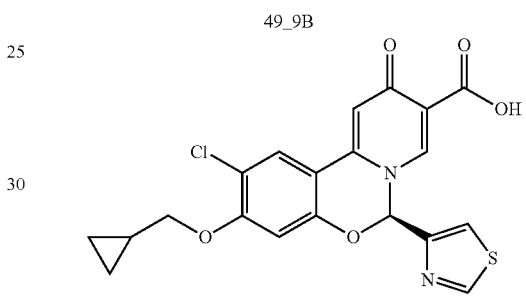

Embodiment 49_A or 49_B

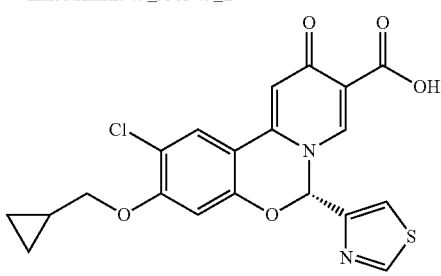

Embodiment 49_B or 49_A

Step A: 49-1 (50.01 g, 297.41 mmol) was dissolved in DMF (300 mL), then cooled down to 0° C. and potassium carbonate (41.10 g, 297.41 mmol) was added. The mixture was heated to 90° C. and then bromomethyl cyclopropane (40.15 g, 297.41 mmol) was added dropwise in about 1 hour, and then the mixture was stirred at 90° C. for 1 hour. Then the solution was added into 200 mL water, followed by extraction with EtOAc (400 mL*3), the organic phase was collected and washed with water (150 mL) and saturated brine (100 mL*3), then concentrated under reduced pressure to give a white solid. The white solid was purified by silica gel chromatography (eluent: PE/EtOAc=30/1-20/1) to give compound 49-2.

$^1$H NMR (400 MHz, CDCl$_3$) δ 10.87 (s, 1H), 7.65 (d, J=8.8 Hz, 1H), 6.40-6.34 (m, 2H), 3.83 (s, 3H), 3.74 (d, J=6.9 Hz, 2H), 1.23-1.15 (m, 1H), 0.62-0.55 (m, 2H), 0.28 (q, J=5.0 Hz, 2H).

Step B: 49-2 (47.00 g, 211.48 mmol) was dissolved in acetonitrile (200.00 mL) and cooled down to 0° C., N-chlorosuccinimide (28.52 g, 213.59 mmol) was then added. The mixture was heated to 90° C. and stirred for 2 hours. The reaction mixture was concentrated under reduced pressure to give a yellow residue, and the yellow residue obtained was dissolved in EtOAc (400 mL), then water (300 mL) was added thereto, the solution was stirred at 25° C. for 2 mins. The organic phase was separated, and washed with saturated brine (100 mL*3), then dried over anhydrous sodium sulfate, concentrated under reduced pressure, triturated with PE/dichloromethane (30/1) to give compound 49-3.

Step C: Potassium carbonate (62.78 g, 454.26 mmol) was added into 49-3 (53.00 g, 206.48 mmol) and benzyl bromide (38.85 g, 227.13 mmol) in DMF (400.00 mL) solution. The mixture was then stirred at 25° C. for 1 hour. EtOAc (800 mL) and water (150 mL) were added into the solution, which was then stirred at 20° C. for 10 mins, the organic phase was separated and washed with water (130 mL*2) and saturated brine (130 mL*2), then dried over anhydrous sodium sulfate, and dried under reduced pressure to give compound 49-4.

Step D: Potassium hydroxide (74.07 g, 1.32 mol) was added into the mixture of 49-4 (60.00 g, 173.01 mmol) in methanol (300.00 mL) and water (100.00 mL). The mixture was stirred at 50° C. for 2 hours. Then the mixture was concentrated under reduced pressure to 100 mL, then washed with EtOAc/PE (4/1 100 mL). The aqueous phase was separated, then adjusted by 1 mol/L diluted hydrochloric acid to pH=3-4 to give a suspension. The suspension was filtered and gave a solid. The solid obtained was triturated by water (100 mL) and filtered, and then recrystallized in the mixture of n-heptane/EtOAc to give compound 49-5.

$^1$H NMR (400 MHz, CDCl$_3$) δ 8.18-8.16 (m, 1H), 7.48-7.43 (m, 5H), 6.58 (s, 1H), 5.29 (s, 2H), 3.92 (d, J=6.8 Hz, 2H), 1.29 (br s, 1H), 0.72-0.68 (m, 2H), 0.44-0.39 (m, 2H).

Step E: Oxalyl chloride (19.83 g, 156.26 mmol) was added dropwise into 49-5 (26.00 g, 78.13 mmol) in dichloromethane (30 mL) solution. After addition, the mixture was stirred at 28° C. for 2 hours. Then the mixture was concentrated under reduced pressure to give compound 49-6.

Step F: compound 49-6 (27.00 g, 76.87 mmol) and (2Z)-2-(dimethylaminomethylene)-3-ethyl oxobutyrate (14.50 g, 78.30 mmol) in tetrahydrofuran (300 mL) solution were added dropwise into lithium hexamethyldisilazide (1 mol/L, 195.75 mL) in tetrahydrofuran (20 mL) solution (more than 5 mins) at −70° C. After addition, the cooling bath was removed, and the mixture was stirred for further 5 mins. Ammonium acetate (9.05 g, 117.45 mmol) and acetic acid (164.09 g, 2.73 mol) were added into the mixture, and most of the tetrahydrofuran was removed by rotary evaporator, and the residue was stirred for 1.5 hours at 60-65° C. After the reaction mixture was cooled down, water (100 mL) and EtOAc (300 mL) were added. Then the mixture was stirred for further 10 mins and then separated. The organic phase was washed with water (100 mL*3) and saturated sodium dicarbonate (100 mL) solution, then dried and concentrated to give a yellow residue. The yellow residue was purified by silica gel chromatography (eluent: PE/EtOAc=10/1) to give compound 49-7.

$^1$H NMR (400 MHz, CDCl$_3$) δ 11.06 (br s, 1H), 9.00 (s, 1H), 8.06 (s, 1H), 7.62 (s, 1H), 7.41-7.32 (m, 5H), 6.58 (s, 1H), 5.19-5.15 (m, 2H), 4.47 (q, J=7.1 Hz, 2H), 3.87 (d, J=6.7 Hz, 2H), 1.46 (t, J=7.2 Hz, 3H), 1.32-1.22 (m, 1H), 0.69-0.62 (m, 2H), 0.41-0.35 (m, 2H).

Step G: Palladium on carbon (1.00 g, 10%) was added into 49-7 (26.00 g, 57.28 mmol) in tetrahydrofuran (500.00 mL) solution (the reaction system was pre-charged by N$_2$). Then the solution was stirred at 25° C. for 2 hours under hydrogen atmosphere (30 psi). The brown suspension was filtered to give a yellow liquid. Then the solution was concentrated under reduced pressure to give a yellow residue, then triturated with PE/EtOAc (4/1 60 mL) twice, filtered to give compound 49-8.

$^1$H NMR (400 MHz, CDCl$_3$) δ 14.48 (s, 1H), 11.18 (s, 1H), 8.78 (s, 1H), 7.64 (s, 1H), 7.19 (s, 1H), 6.43 (s, 1H), 4.40 (q, J=7.1 Hz, 2H), 3.84 (d, J=6.7 Hz, 2H), 1.38 (t, J=7.2 Hz, 3H), 1.35-1.20 (m, 1H), 0.64-0.54 (m, 2H), 0.37-0.31 (m, 2H).

Step H, I may be obtained according to the method in embodiment 13.

The pre-hydrolysis compound of embodiment 49 was separated by chiral HPLC column (column: AS (250 mm*30 mm, 10 m); mobile phase: [0.1% NH$_3$H$_2$O-MeOH]; elution gradient: 30%-30%, 4.4 min; 600 min) to give isomers with two configurations (49-9A and 49-9B), then the embodiment 49_A (t=3.885 min), ee value (enantiomeric excess): 100% and embodiment 49_B (t=4.831 min), ee value (enantiomeric excess): 100% were obtained respectively. Method for determination of the ee value (enantiomeric excess): AD-3S_3_40_3ML_8 MIN Column: Chiralpak AD-3 100× 4.6 mm I.D., 3 μm Mobile phase: 40% methanol (0.05% DEA) in CO$_2$ Flow rate: 3 mL/min Wavelength: 220 nm.

Embodiment 49_A: $^1$H NMR (400 MHz, CDCl$_3$) δ 16.16 (s, 1H), 9.08 (d, J=1.96 Hz, 1H), 8.97 (s, 1H), 8.24 (s, 1H), 7.82 (d, J=0.86 Hz, 1H), 7.79 (s, 1H), 7.47 (s, 1H), 7.07 (s, 1H), 3.95-4.08 (m, 2H), 1.22-1.31 (m, 1H), 0.58-0.65 (m, 2H), 0.32-0.40 (m, 2H).

Embodiment 49_B: $^1$H NMR (400 MHz, CDCl$_3$) δ 16.14 (br s, 1H), 9.07 (d, J=1.83 Hz, 1H), 8.96 (s, 1H), 8.23 (s, 1H), 7.80 (br d, J=15.89 Hz, 2H), 7.45 (s, 1H), 7.06 (s, 1H), 3.98-4.07 (m, 2H), 1.23-1.32 (m, 1H), 0.58-0.68 (m, 2H), 0.32-0.44 (m, 2H).

Embodiment 50 (50_A and 50_B)

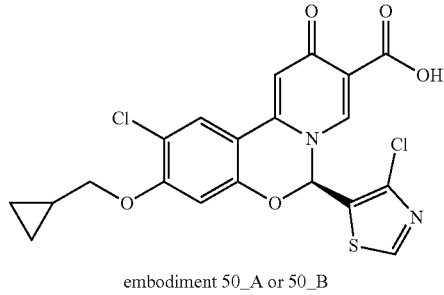

embodiment 50_A or 50_B

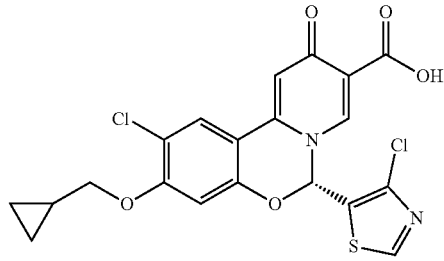

embodiment 50_B or 50_A

Embodiment 50 was prepared according to the method in embodiment 13.

The pre-hydrolysis compound of embodiment 50 was separated by chiral HPLC (column: OJ (250 mm*30 mm, 10 m); mobile phase: [0.1% NH₃H₂O-MeOH]; elution gradient: 40%-40%, 3 min; 700 min) to give isomers with two configurations, t=3.277 min and t=3.598 min, the embodiment 50_A (t=4.408 min), ee value (enantiomeric excess): 95.5% and embodiment 50_B (t=4.145 min), ee value (enantiomeric excess): 84.9% were obtained respectively. The ee value (enantiomeric excess) determination method: OD-3S_3_5_40_3 ML Column: Chiralcel OD-3 100×4.6 mm I.D., 3 μm Mobile phase: methanol (0.05% DEA) in CO₂ from 5% to 40% Flow rate: 3 mL/min Wavelength: 220 nm.

Embodiment 50_A: ¹H NMR (400 MHz, DMSO-d6) δ 9.11 (s, 1H), 8.88 (br s, 1H), 8.38 (s, 1H), 7.96 (s, 1H), 7.54 (br s, 1H), 7.01 (s, 1H), 4.06-3.94 (m, 2H), 1.28-1.20 (m, 1H), 0.62-0.56 (m, 2H), 0.38-0.32 (m, 2H).

Embodiment 50_B: ¹H NMR (400 MHz, DMSO-d6) δ 15.86 (br s, 1H), 9.11 (s, 1H), 8.89 (s, 1H), 8.39 (s, 1H), 7.96 (s, 1H), 7.55 (s, 1H), 7.01 (s, 1H), 4.06-3.94 (m, 2H), 1.24 (br t, J=7.0 Hz, 1H), 0.63-0.56 (m, 2H), 0.63-0.56 (m, 1H), 0.38-0.33 (m, 2H).

Embodiment 51 (51_A and 51_B)

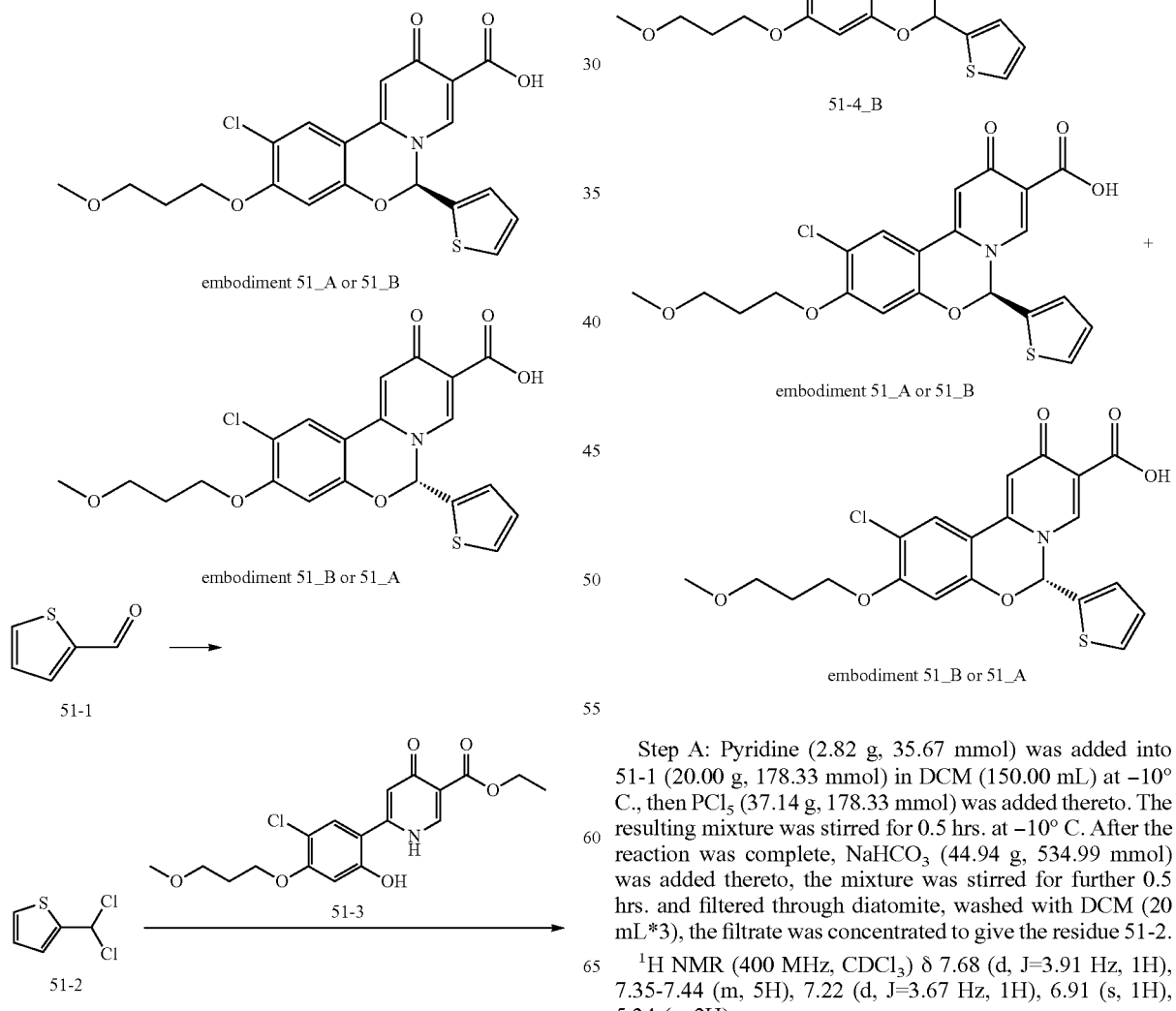

Step A: Pyridine (2.82 g, 35.67 mmol) was added into 51-1 (20.00 g, 178.33 mmol) in DCM (150.00 mL) at −10° C., then PCl₅ (37.14 g, 178.33 mmol) was added thereto. The resulting mixture was stirred for 0.5 hrs. at −10° C. After the reaction was complete, NaHCO₃ (44.94 g, 534.99 mmol) was added thereto, the mixture was stirred for further 0.5 hrs. and filtered through diatomite, washed with DCM (20 mL*3), the filtrate was concentrated to give the residue 51-2.

¹H NMR (400 MHz, CDCl₃) δ 7.68 (d, J=3.91 Hz, 1H), 7.35-7.44 (m, 5H), 7.22 (d, J=3.67 Hz, 1H), 6.91 (s, 1H), 5.34 (s, 2H).

Step B: The solution of 51-3 (10.00 g, 26.19 mmol), $Cs_2CO_3$ (38.40 g, 117.86 mmol) and 51-2 (21.88 g, 130.95 mmol) in $SOCl_2$ (100.00 mL) was stirred for 16 hrs. at 100° C. After the reaction was complete, the reaction was quenched by water (50 mL), then diluted with water (150 mL), extracted with DCM (100 mL*3). The organic phases were combined and washed with saturated brine (100 mL*3), dried over anhydrous sodium sulfate, and concentrated under reduced pressure to give the residue, which was purified by silica gel chromatography (eluent: DCM/EtOH=100/1 to 8/1) to give compound 51-4. Then the obtained solid was separated by chiral HPLC (column: AS (250 mm*30 mm, 10 m); mobile phase: [0.1% $NH_3H_2O$-EtOH]; elution gradient: 40%-40%, 4.3 min; 120 min) to give 51-4_A (t=2.516 min) and 51-4_B (t=5.098 min).

Step C The hydrolysis was operated according to the method in embodiment 13.

Compound 51_A was obtained by hydrolysis on 51-4_A. (t=3.842 min), ee value (enantiomeric excess): 100%; and 51-4_B was obtained by hydrolysis on compound 51_B (t=2.682 min), ee value (enantiomeric excess): 100%. Method for determination of the ee value (enantiomeric excess): OD-3S_3_40_3ML Column: Chiralcel OD-3 100× 4.6 mm I.D., 3 m Mobile phase: 40% MeOH (0.05% DEA) $CO_2$ Flow rate: 3 mL/min Wavelength: 220 nm.

Compound 51_A: $^1$H NMR (400 MHz, $CDCl_3$) δ 15.40 (s, 1H), 8.32 (s, 1H), 7.62 (s, 1H), 7.41 (dd, J=1.28, 4.83 Hz, 1H), 6.93-6.98 (m, 2H), 6.91 (s, 1H), 6.88 (s, 1H), 6.62 (s, 1H), 4.09 (t, J=6.24 Hz, 2H), 3.51 (t, J=5.87 Hz, 2H), 3.28 (s, 3H), 2.05 (quin, J=6.08 Hz, 2H)

Compound 51_B: $^1$H NMR (400 MHz, $CDCl_3$) δ 15.46 (s, 1H), 8.38 (s, 1H), 7.69 (s, 1H), 7.48 (dd, J=1.47, 4.89 Hz, 1H), 7.00-7.04 (m, 2H), 6.98 (s, 1H), 6.93 (s, 1H), 6.69 (s, 1H), 4.16 (t, J=6.24 Hz, 2H), 3.58 (t, J=5.93 Hz, 2H), 3.35 (s, 3H), 2.12 (quin, J=6.05 Hz, 2H).

Experiment 1: HBV In Vitro Test

1. Experimental Objective:

The content of HBV DNA in HepG2. 2. 15 cell culture supernatant was detected by a real-time quantitative qPCR assay (real time-qPCR), and the content of HBV surface antigen was detected by enzyme-linked immunosorbent assay (ELISA), the compound $EC_{50}$ value was used as an index to evaluate the inhibitory effect of the compound on HBV.

2. Experiment Material:

2.1. Cell Line: HepG2. 2. 15 Cells

HepG2. 2. 15 cell culture medium (DMEM/F12, Invitrogen-11330032; 10% serum, Invitrogen-10099141; 100 units/mL penicillin and 100 μg/mL streptomycin, Hyclone-SV30010; 1% non-essential amino acids, Invitrogen-11140050; 2 mM L-GLUTAMINE, Invitrogen-25030081; 300 μg/mL Geneticin, Invitrogen-10131027

2.2. Reagents:

Trypsin (Invitrogen-25300062)
DPBS (Corning-21031CVR)
DMSO (Sigma-D2650-100ML)
High-throughput DNA purification kit (QIAamp 96 DNA Blood Kit, Qiagen-51162)
Quantitative quick start universal probe reagent (FastStart Universal Probe Master, Roche-04914058001)
Hepatitis B surface antigen quantitative detection kit (Antu Bio, CL 0310)

2.3. Consumables and Instruments:

96-well cell culture plate (Corning-3599)
$CO_2$ incubator (HERA-CELL-240)
Optical sealing film (ABI-4311971)
Quantitative PCR 96-well plate (Applied Biosystems-4306737)
Fluorescence quantitative PCR machine (Applied Biosystems-7500 real time PCR system)

3. Experimental Procedures and Methods:

3.1. HepG2. 2. 15 cells ($4\times10^4$ cells/well) was plated into a 96-well plate and cultured overnight at 37° C., 5% $CO_2$.

3.2. The next day, the compound was diluted to 8 concentrations, 3-folds gradients dilution. The compound of different gradients were added into the culture well, double duplicated the wells. The final concentration of the DMSO was 0.5% in the culture solution. 10 μM ETV was used as 100% inhibition control; 0.5% of DMSO was used as 0% inhibition control.

3.3. On the fifth day, the culture solution was replaced by fresh culture solution containing the compound.

3.4. On the eighth day, the culture solution in the culture well was collected, and the content of hepatitis B virus S antigen was measured by ELISA with partial samples; and still partial samples was taken for extraction of DNA using high-throughput DNA purification kit (Qiagen-51162).

3.5. Preparation of PCR reaction solution was shown in table 1:

TABLE 1

Preparation of PCR reaction solution

| project | Volume needed for 1 well (μL) | Volume needed for 80 well (μL) |
|---|---|---|
| Quantitative quick start universal probe reagent | 12.5 | 1000 |
| Pre-primer (10 μL) | 1 | 80 |
| Post-primer (10 μL) | 1 | 80 |
| probe (10 μL) | 0.5 | 40 |

Pre-primer sequence: GTGTCTGCGGCGTTTTATCA
Post-primer sequence: GACAAACGGGCAACATACCTT
Probe sequence: 5' + FAM + CCTCTKCATCCTGCTGCTATGCCTCATC + TAMRA-3'

3.6. 15 μL reaction mixture was added into each well of the 96-well PCR plate, then in each well was added 10 μL sample DNA or standard product of HBV DNA.

3.7. The qPCR plate was sealed with optical sealing film, centrifuged at 1500 rpm for 2 minutes, and then the HBV copy number of each sample was quantitatively detected by fluorescence quantitative qPCR. The operation procedure of qPCR is as follows

| Temperature (° C.) | denaturation | cycles | Acquisition mode |
|---|---|---|---|
| 95 | 0:10:00 | 1 | None |
| 95 | 0:00:15 | 40 | None |
| 60 | 0:01:00 | | Single time |

3.8. Data analysis:

Calculation of the Inhibition Percentage

% Inh.=(1−value in the sample/DMSO control group value)×100%.

The dose-response curves was fitted by GraphPad Prism software, and the 50% inhibited concentration $EC_{50}$ value of the compound against HBV was calculated.

3.9. Content determination of hepatitis B virus S antigen measured by ELISA

Specific steps should refer to the product manual, and a brief description of the steps were as follows:

50 μL sample and standard sample were taken and added into the reaction plate respectively, then 50 μL enzyme conjugate was added into each of the wells, shaked to mix well, then kept in warm bath at 37° C. for 60 min, and the plate was washed with cleansing solution for 5 times, 50 μL luminescent substrate was added into each wells, mixed well and reacted at r.t. for 10 min in the dark, the chemiluminescence intensity was finally detected with ELISA. The inhibition percentage of each compound was calculated by the following formula: inhibition rate (%)=(1−value in sample/DMSO control group value)×100%. The dose-response curves was fitted by GraphPad Prism software, and the 50% inhibited concentration $EC_{50}$ value of the compound against HBV was calculated.

4. Experimental Results: Refer to Table 2 and 3.

TABLE 2

| HBV-DNA experimental results | |
|---|---|
| Test compound | $EC_{50}$ (nM) |
| 1 | 11.82 |
| 2 | 34.5 |
| 3 | 27.61 |
| 4 | 14.98 |
| 5 | 15.05 |
| 6 | 6.04 |
| 7 | 211.2 |
| 8 | 20.84 |
| 9 | 74.06 |
| 10 | 50.96 |
| 11 | 40.8 |
| 12 | 78.06 |
| 13_A | 300 |
| 13_B | 7.33 |
| 14 | 6.88 |
| 15 | 8.2 |
| 16 | 45.29 |
| 17 | 254.1 |
| 18 | 40.82 |
| 19 | 3.88 |
| 20 | 11.02 |
| 21 | 7.12 |
| 22 | 20.65 |
| 23 | 85.88 |
| 24 | 59.32 |
| 25 | 18.71 |
| 26 | 152.2 |
| 27 | 23.57 |
| 28 | 277.7 |
| 29 | 4.113 |
| 30 | 18.52 |
| 31 | 90.54 |
| 32 | 35.22 |
| 33 | 12.64 |
| 34 | 21.27 |
| 35 | 25.15 |
| 37 | 10.59 |
| 38 | 20.35 |
| 39_A | 3.51 |
| 39_B | 764.9 |
| 40_A | 15.18 |
| 40_B | >1000 |
| 41 | 17.76 |
| 42 | 2.19 |
| 43 | 19.36 |
| 44 | 128.9 |
| 45_A | 77.10 |
| 45_B | 0.22 |
| 46_A | 79.66 |
| 46_B | 43.01 |
| 47_A | 0.44 |

TABLE 2-continued

| HBV-DNA experimental results | |
|---|---|
| Test compound | $EC_{50}$ (nM) |
| 47_B | 26.88 |
| 48 | >1000 |
| 49_A | 2.54 |
| 49_B | 333.9 |
| 50_A | 0.69 |
| 50_B | 2.82 |
| 51_A | 1.13 |
| 51_B | 147.2 |

Conclusion: the representative compound of the present disclosure can effectively reduce the content of HBV-DNA, which shows significant inhibitory effect on HBV.

TABLE 3

| HBsAg experimental results | |
|---|---|
| Test compound | $EC_{50}$ (nM) |
| 1 | 27.65 |
| 2 | 55.78 |
| 3 | 47.62 |
| 4 | 31.88 |
| 5 | 49.95 |
| 6 | 20.33 |
| 7 | 299.3 |
| 8 | 66.22 |
| 9 | 137.5 |
| 10 | 102.4 |
| 11 | 73.89 |
| 12 | 212.7 |
| 13_A | 300 |
| 13_B | 7.33 |
| 14 | 6.88 |
| 15 | 8.2 |
| 16 | 45.29 |
| 17 | 254.1 |
| 18 | 73.7 |
| 19 | 20.9 |
| 20 | 22.47 |
| 21 | 16.27 |
| 22 | 38.23 |
| 23 | 127 |
| 24 | 35.5 |
| 25 | 35.92 |
| 26 | 101.3 |
| 27 | 39.15 |
| 28 | 152.5 |
| 29 | 12.19 |
| 30 | 28.2 |
| 31 | 202.7 |
| 32 | 71.05 |
| 33 | 10.25 |
| 34 | 29.63 |
| 35 | 11.03 |
| 37 | 26.58 |
| 38 | 12.32 |
| 39_A | 6.75 |
| 39_B | >1000 |
| 40_A | 1.45 |
| 40_B | 10.08 |
| 41 | 57.97 |
| 42 | 7.88 |
| 43 | 15.42 |
| 44 | 212.2 |

TABLE 3-continued

HBsAg experimental results

| Test compound | EC$_{50}$ (nM) |
|---|---|
| 45_A | 104.6 |
| 45_B | 1.09 |
| 46_A | 122.9 |
| 46_B | 73.96 |
| 47_A | 0.84 |
| 47_B | 46.01 |
| 48 | 103.3 |
| 49_A | 4.62 |
| 49_B | 965.9 |
| 50_A | 1.31 |
| 50_B | 3.62 |
| 51_A | 1.54 |
| 51_B | 349.7 |

Conclusion: the compound of the present disclosure can effectively reduce the content of HBV surface antigen (HBsAg), which shows significant inhibitory effect against HBV.

What is claimed is:

1. A compound represented by formula (I) or a pharmaceutically acceptable salt thereof,

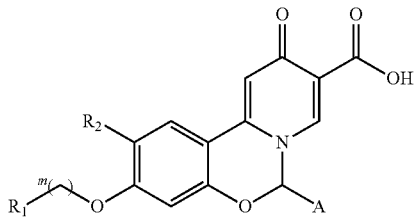

wherein, $R_1$ is selected from H, OH, CN, NH$_2$, or selected from the group consisting of C$_{1-5}$ alkyl, C$_{1-5}$ heteroalkyl, C$_{2-5}$ alkynyl, C$_{3-6}$ cycloalkyl and 3-6 membered heterocycloalkyl, each of which is optionally substituted by 1, 2 or 3 R;

$R_2$ is selected from H, halogen, or selected from the group consisting of C$_{1-3}$ alkyl and C$_{1-3}$ heteroalkyl, each of which is optionally substituted by 1, 2 or 3 R;

m is selected from the group consisting of 0, 1, 2, 3, 4 and 5;

A is selected from the group consisting of phenyl and 5-6 membered heteroaryl, each of which is optionally substituted by 1, 2 or 3 R;

R is selected from the group consisting of H, halogen, OH, CN, $NH_2$, =O, $CH_3$, $CH_3CH_2$, $CH_3O$, $CF_3$, $CHF_2$ and $CH_2F$;

the "hetero" in the $C_{1-5}$ heteroalkyl, 3-6 membered heterocycloalkyl, $C_{1-3}$ heteroalkyl and 5-6 membered heteroaryl, is independently selected from the group consisting of N, —O—, =O, —S—, —NH—, —(C=O)—, —(S=O)— and —(S=O)$_2$—;

in any one of the cases above, the number of the heteroatom or the heteroatom group is independently selected from 1, 2 or 3.

2. The compound or the pharmaceutically acceptable salt thereof as defined in claim 1, wherein R is selected from the group consisting of H, F, Cl, Br, OH, $CH_3$, $CH_3O$, $CF_3$, $CHF_2$ and $CH_2F$.

3. The compound or the pharmaceutically acceptable salt thereof as defined in claim 1, wherein $R_1$ is selected from H, OH, CN, $NH_2$, or selected from the group consisting of $CH_3$, $CH_3CH_2$, $CH_3CH_2CH_2$, $CH_3CH_2CH_2CH_2$, $CH_3O$, $CH_3CH_2O$, $CH_3S$, $CH_3S(=O)$, $CH_3S(=O)_2$, $CH_3SCH_2$, $CH_3CH_2S$, $CH_3NH$,

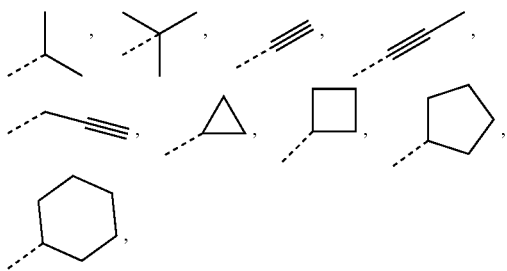

pyrrolidinyl, piperidyl, tetrahydropyranyl, morpholinyl, 2-pyrrolidonyl and 3-pyrrolidonyl, each of which is optionally substituted by 1, 2 or 3 R.

4. The compound or the pharmaceutically acceptable salt thereof as defined in claim 3, wherein Ri is selected from H, OH, CN, $NH_2$, or selected from the group consisting of $CH_3$, $CH_3CH_2$, $CH_3CH_2CH_2$, $CH_3CH_2CH_2CH_2$, $CH_3O$, $CH_3CH_2O$, $CH_3S$, $CH_3S(=O)$, $CH_3S(=O)_2$, $CH_3SCH_2$, $CH_3CH_2S$, $CH_3NH$,

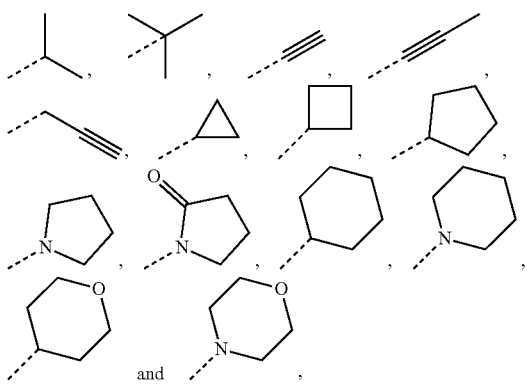

each of which is optionally substituted by 1, 2 or 3 R.

5. The compound or the pharmaceutically acceptable salt thereof as defined in claim 4, wherein $R_1$ is selected from the group consisting of H, OH, $CH_3$, $CHF_2$, $CH_3O$,

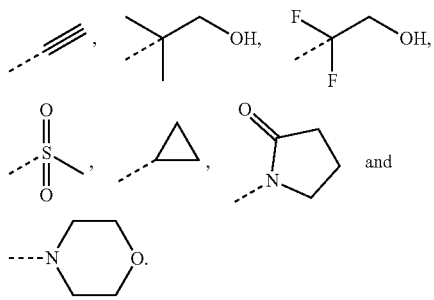

6. The compound or the pharmaceutically acceptable salt thereof as defined in claim 1, wherein $R_2$ is selected from H, F, Cl, Br, or selected from the group consisting of $CH_3$, $CH_3CH_2CH_3O$, $CH_3CH_2O$ and

each of which is optionally substituted by 1, 2 or 3 R.

7. The compound or the pharmaceutically acceptable salt thereof as defined in claim 6, wherein $R_2$ is selected from the group consisting of Cl and $CH_3O$.

8. The compound or the pharmaceutically acceptable salt thereof as defined in claim 1, wherein A is selected from the group consisting of phenyl, thienyl, thiazolyl, isothiazolyl, oxazolyl and isoxazolyl, each of which is optionally substituted by 1, 2 or 3 R.

9. The compound or the pharmaceutically acceptable salt thereof as defined in claim 8, wherein A is selected from the group consisting of

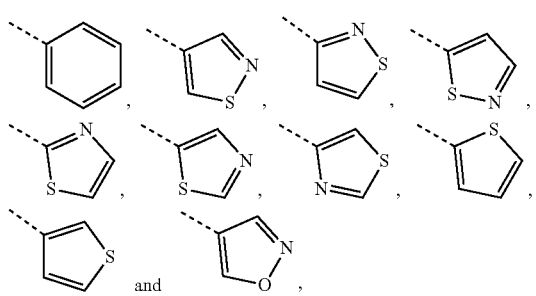

each of which is optionally substituted by 1, 2 or 3 R.

10. The compound or the pharmaceutically acceptable salt thereof as defined in claim 9, wherein A is selected from the group consisting of

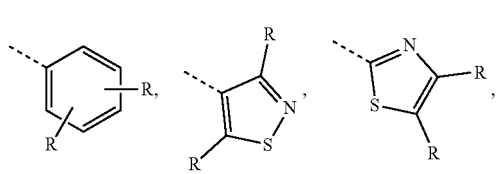

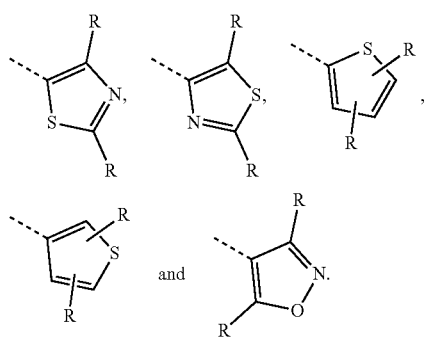

11. The compound or the pharmaceutically acceptable salt thereof as defined in claim 10, wherein A is selected from the group consisting of

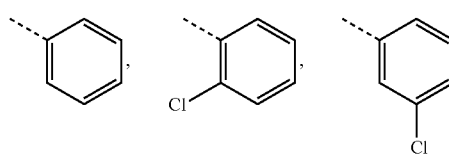

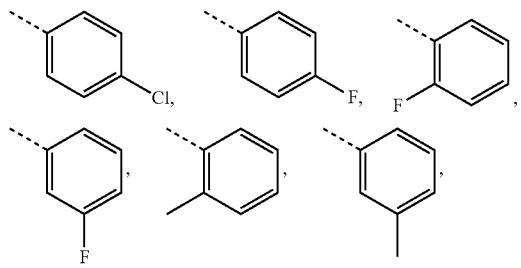

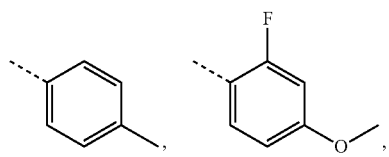

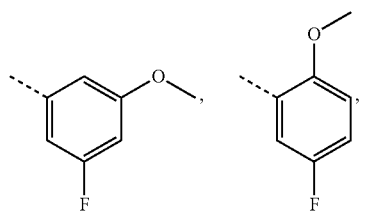

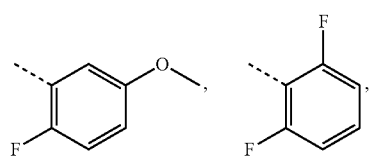

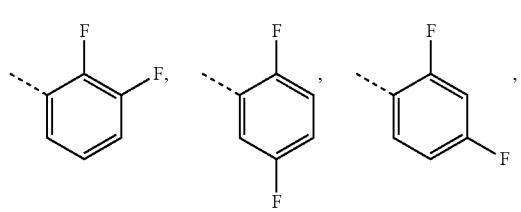

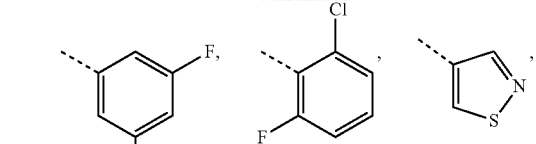

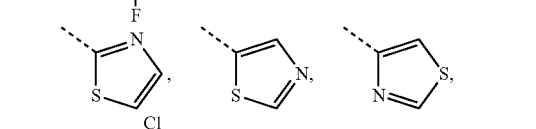

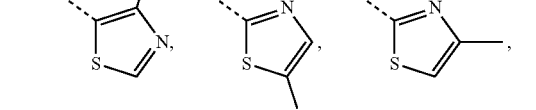

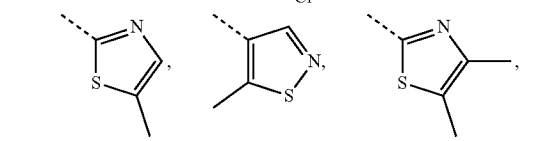

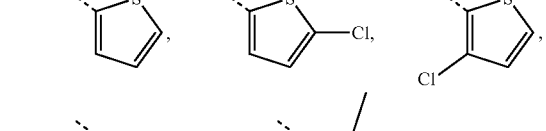

12. The compound or the pharmaceutically acceptable salt thereof as defined in claim 1, wherein in is 3.

13. The compound or the pharmaceutically acceptable salt thereof as defined in claim 12, wherein $R_2$ is selected from the group consisting of Cl and $CH_3O$.

14. The compound or the pharmaceutically acceptable salt thereof as defined in claim 13, wherein $R_1$ is $CH_3O$.

15. The compound or the pharmaceutically acceptable salt thereof as defined in claim 1, wherein m is 1.

16. The compound or the pharmaceutically acceptable salt thereof as defined in claim 15, wherein $R_2$ is Cl.

17. The compound or the pharmaceutically acceptable salt thereof as defined in claim 16, wherein R is

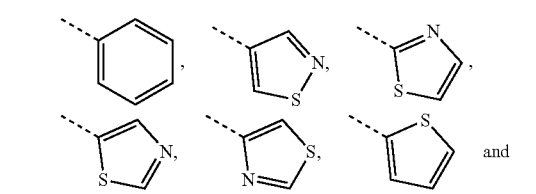

18. The compound or the pharmaceutically acceptable salt thereof as defined in claim 4, wherein A is selected from the group consisting of

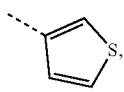
each of which is optionally substituted by 2 or 3 R.
19. The compound or the pharmaceutically acceptable salt thereof as defined in claim 1, which is selected from the group consisting of
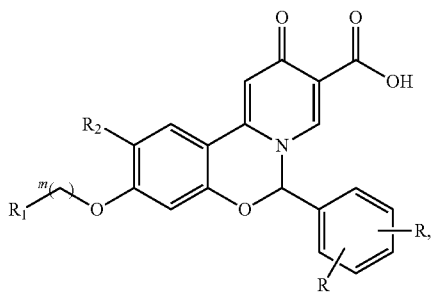
(II)
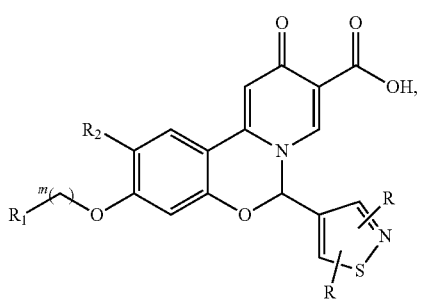
(III)
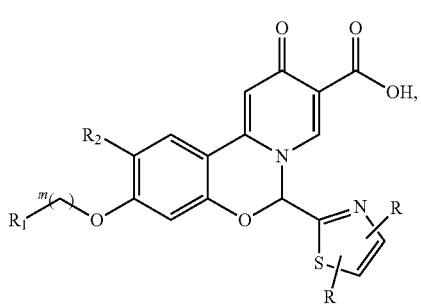
(IV)
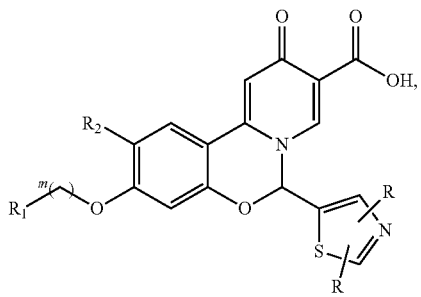
(V)
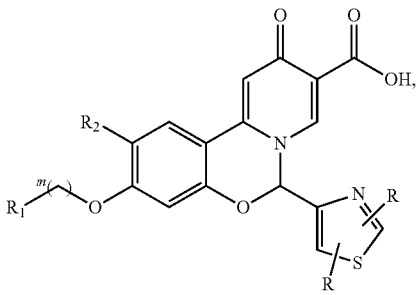
(VI)
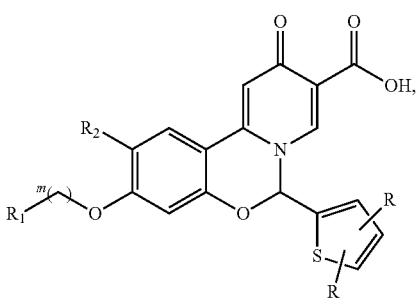
(VII)
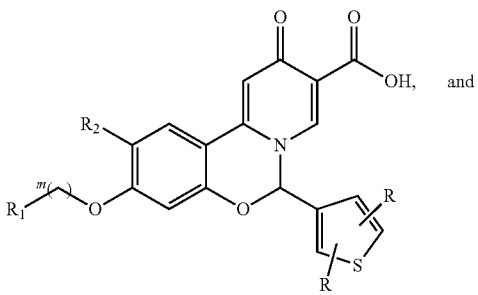
(VIII) and
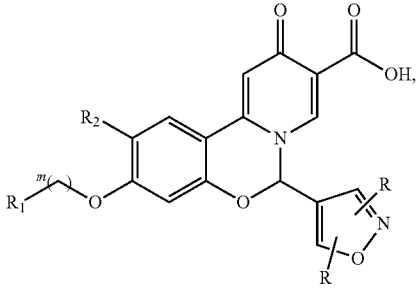
(IX)
wherein,
$R_1$, $R_2$, R and m are as defined in claim 1.
20. The compound or the pharmaceutically acceptable salt thereof, which is selected from the group consisting of
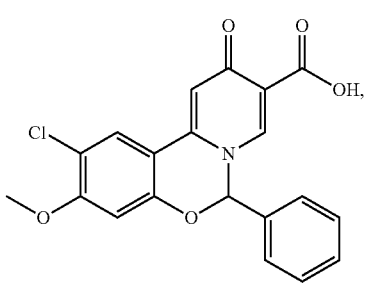

93
-continued
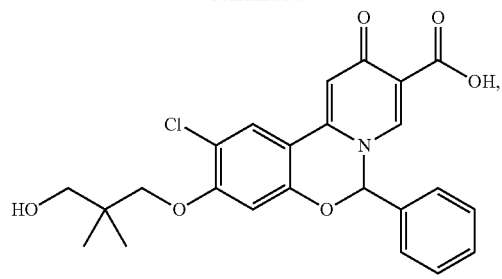
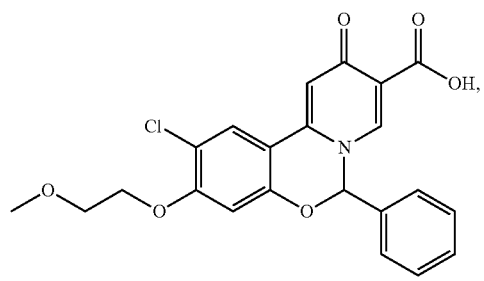
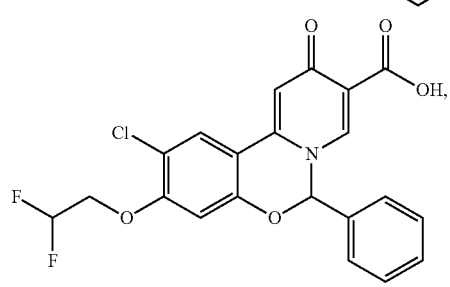
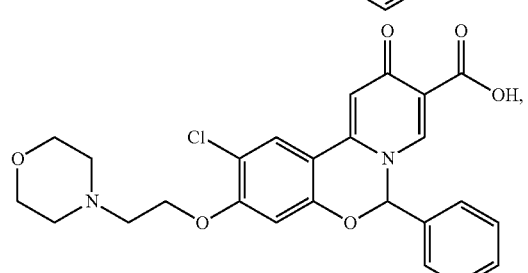
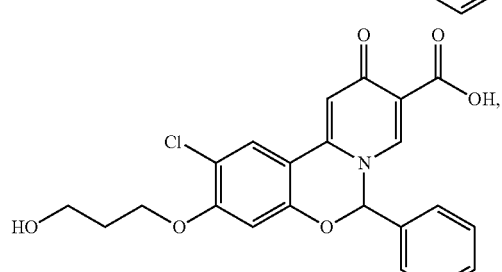
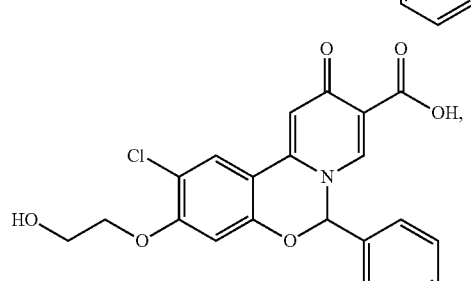
94
-continued
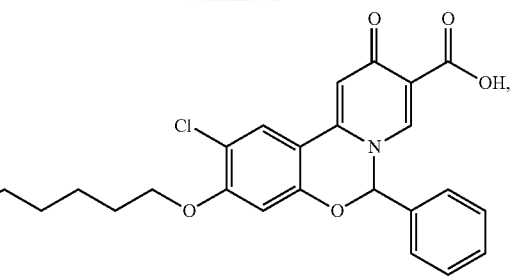
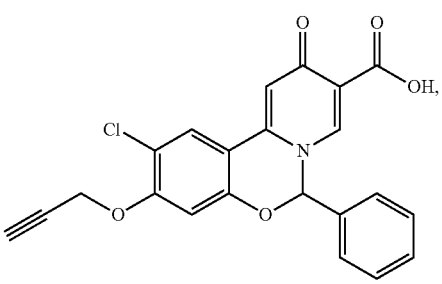
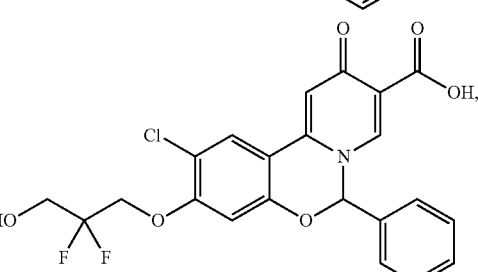
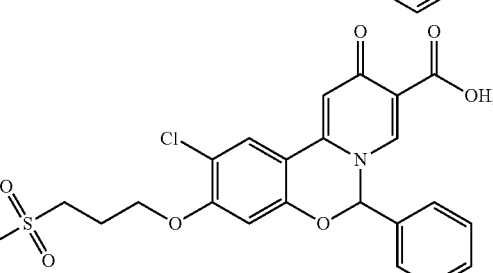
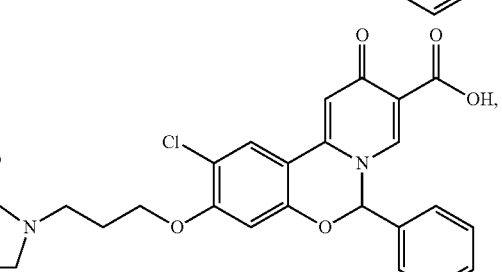
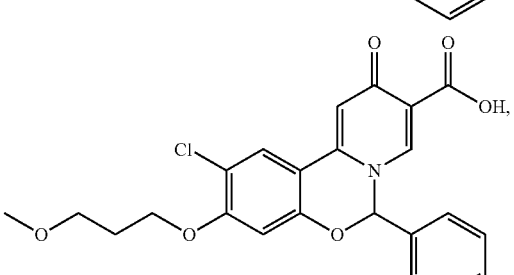

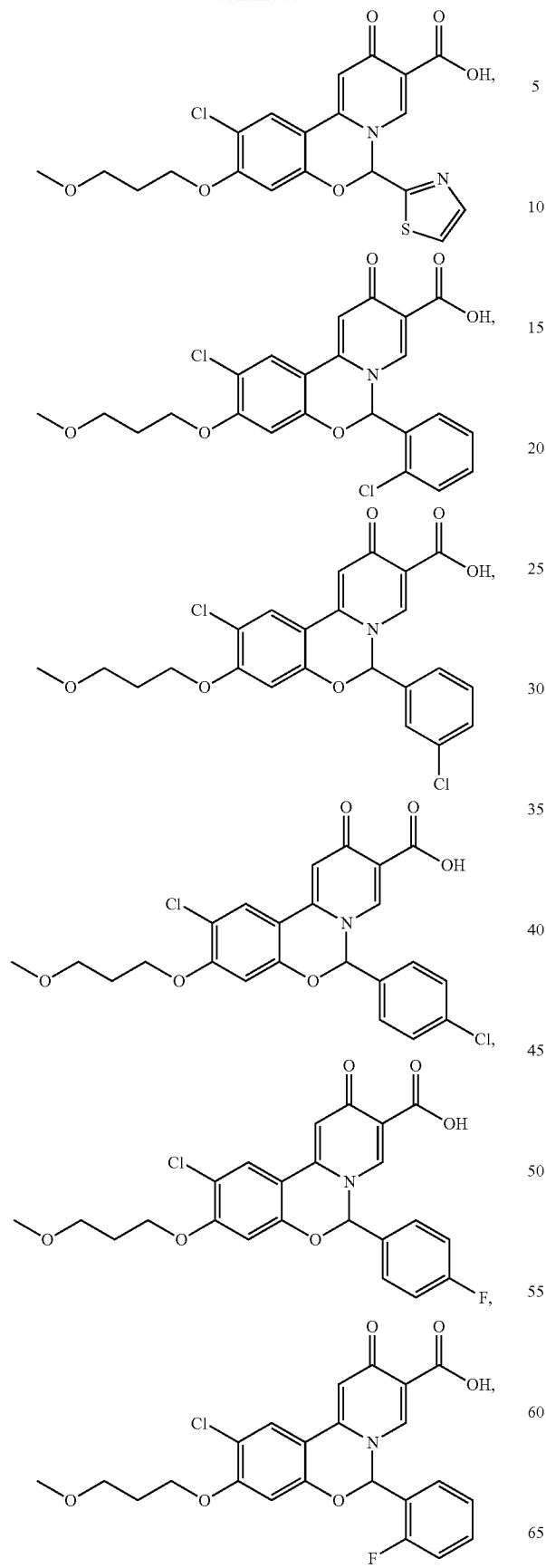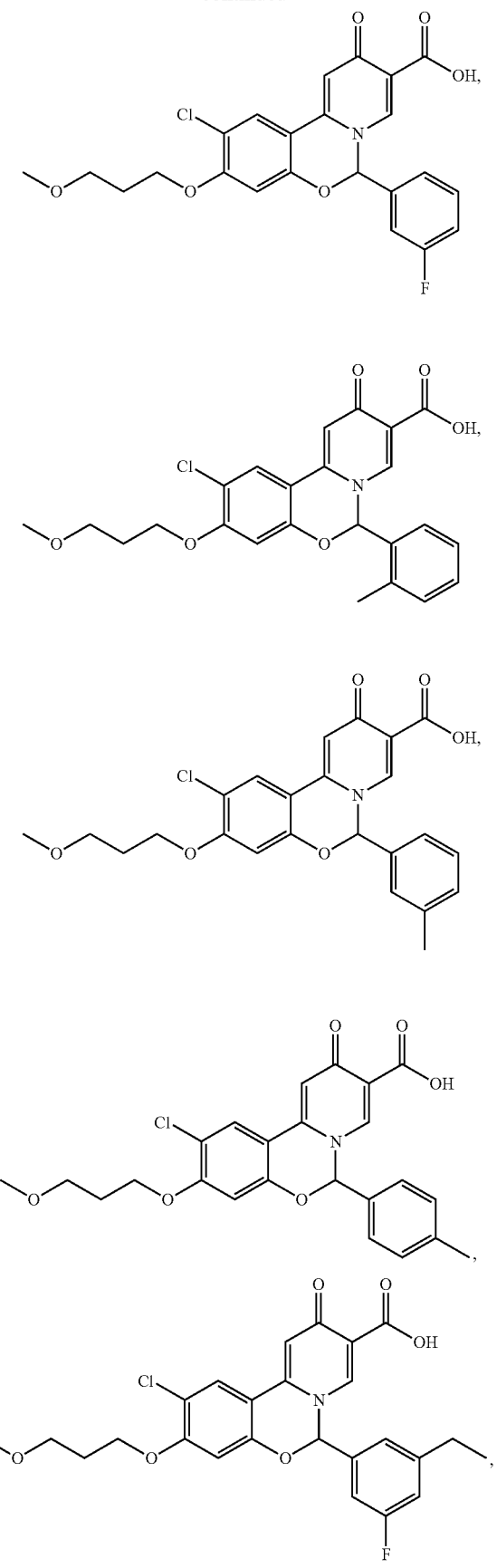

97
-continued
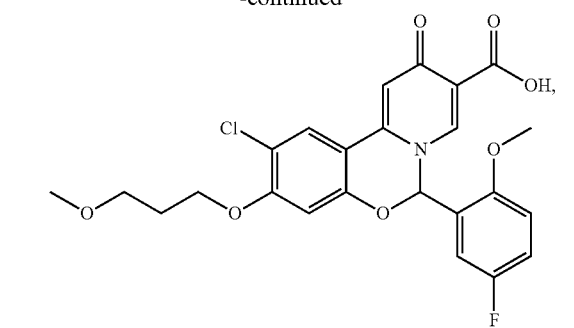
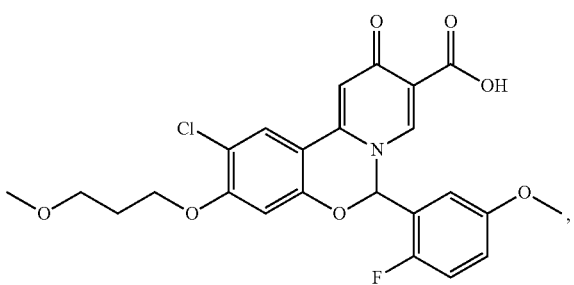
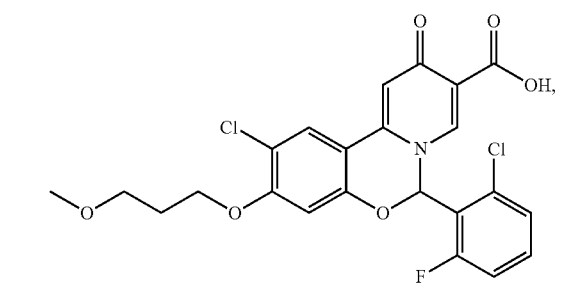
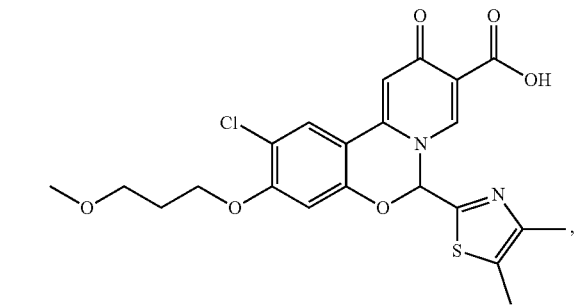
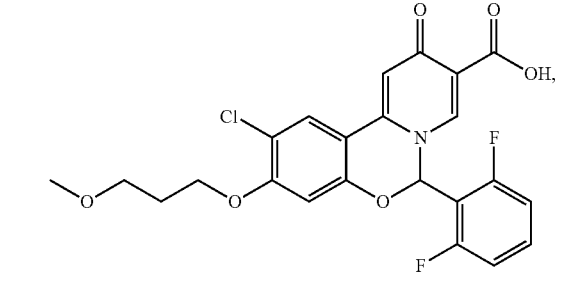
98
-continued
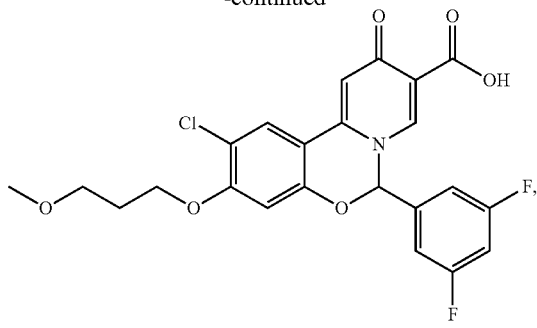
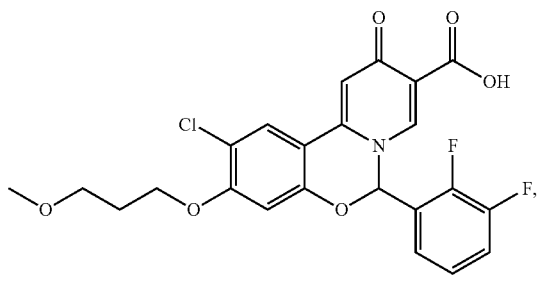
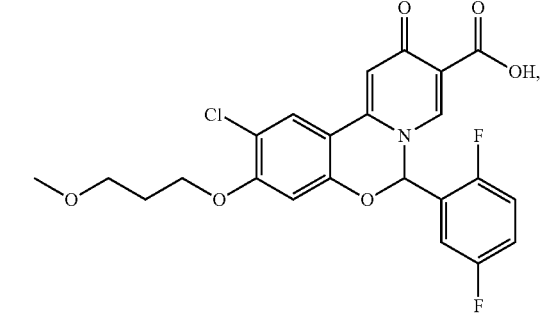
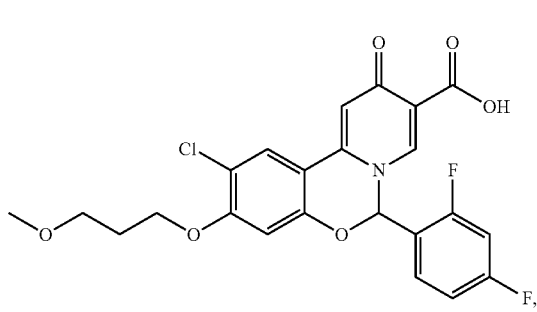
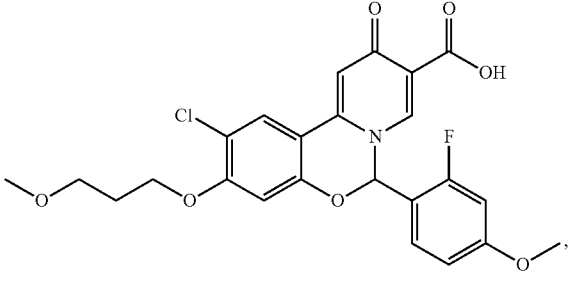

99
-continued
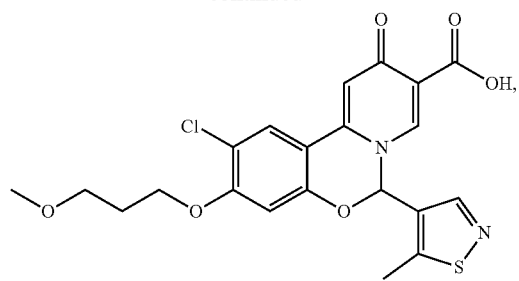
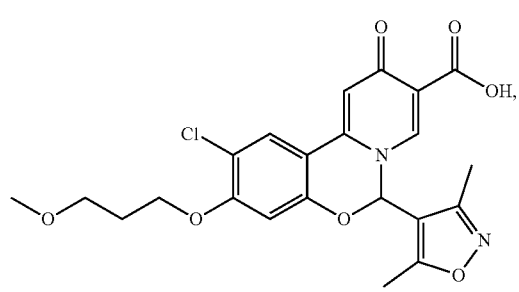
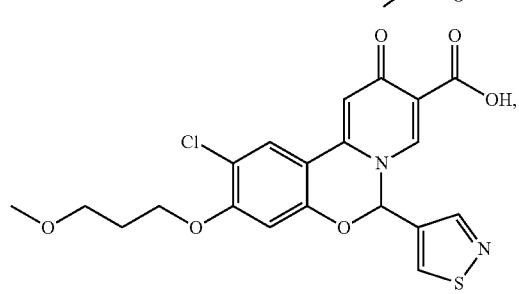
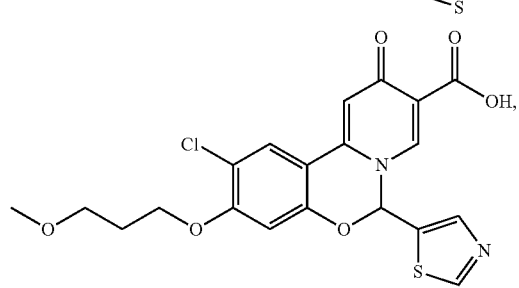
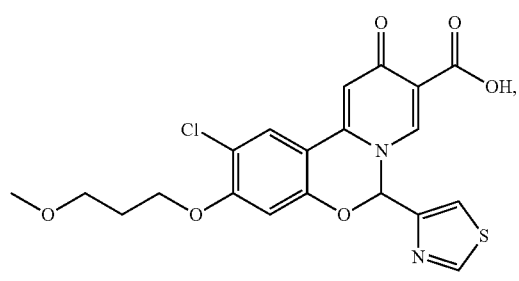
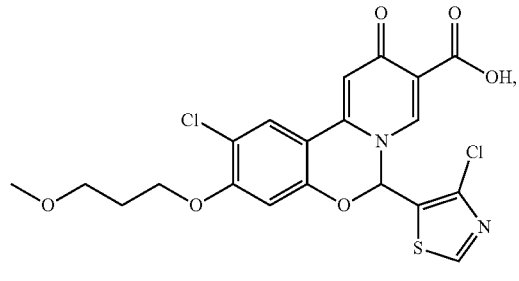
100
-continued
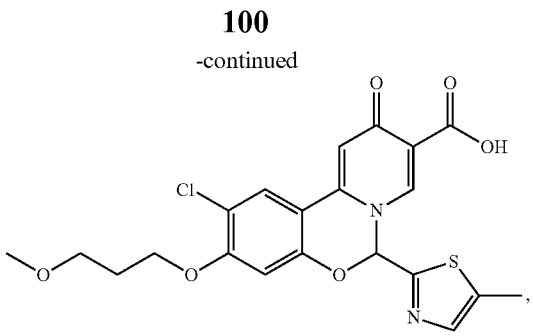
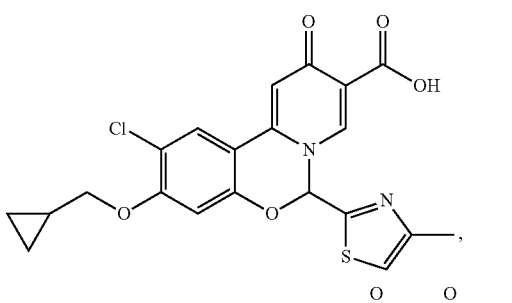
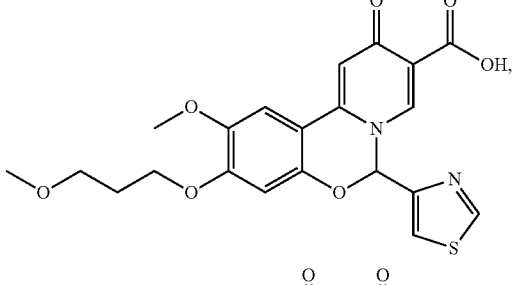
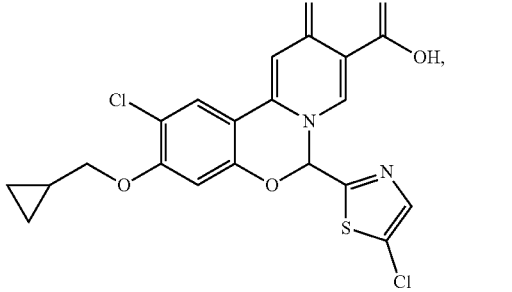
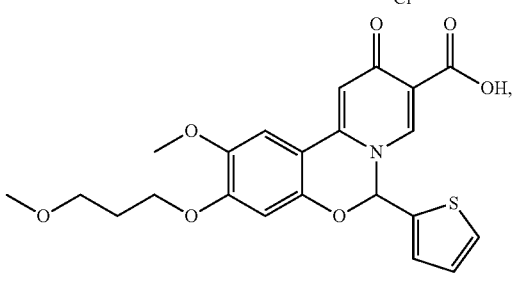
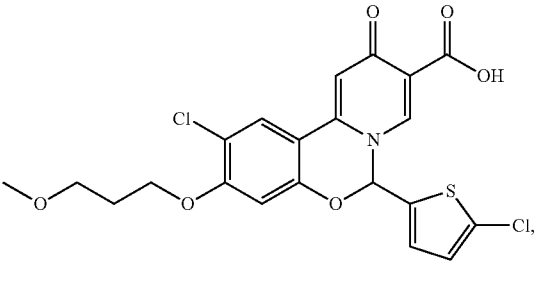

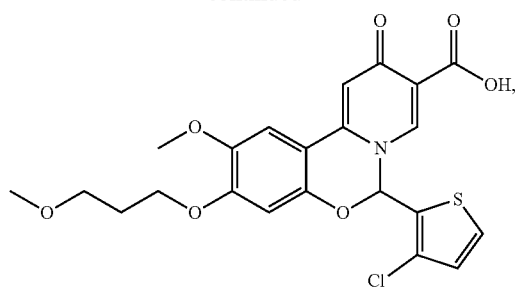
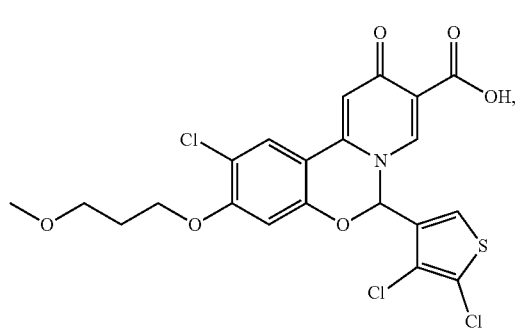
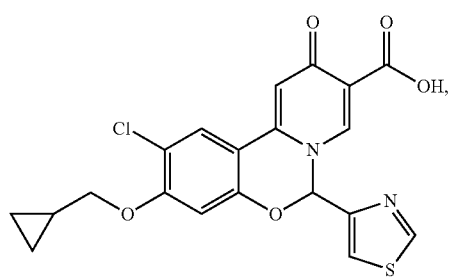
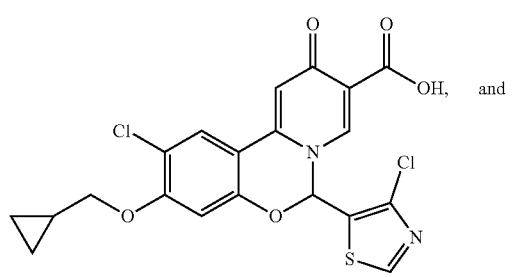 and
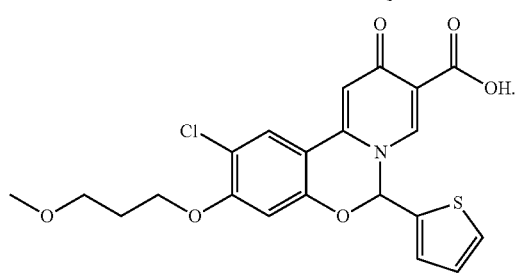
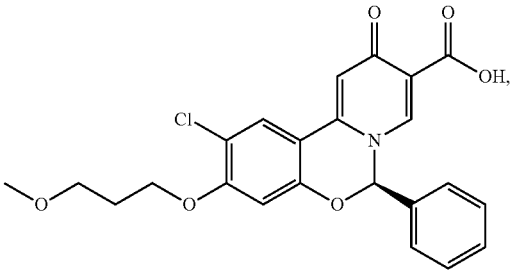
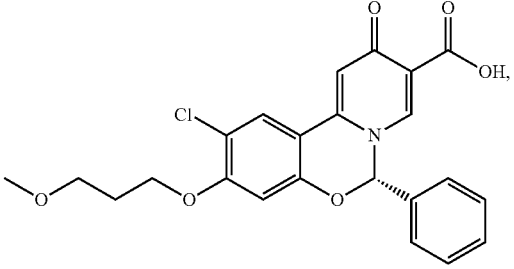
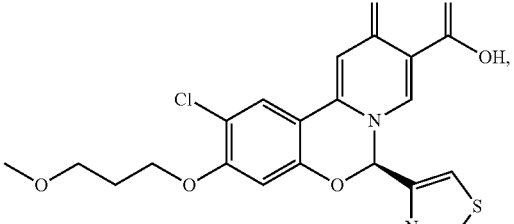
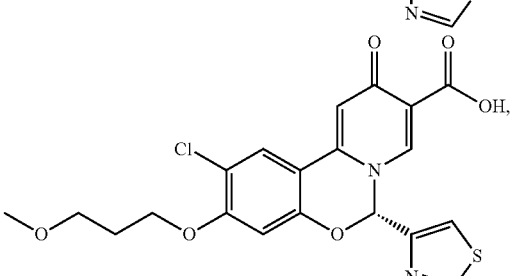
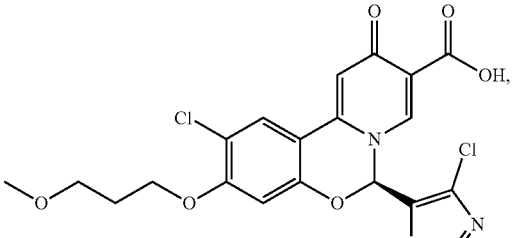
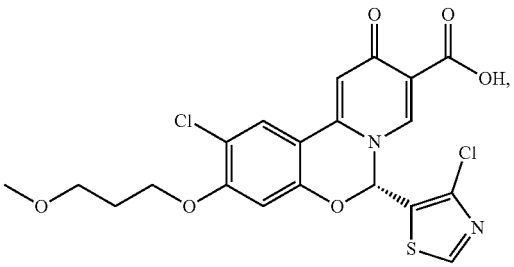
21. The compound or the pharmaceutically acceptable salt thereof as defined claim 20, which is selected from the group consisting of

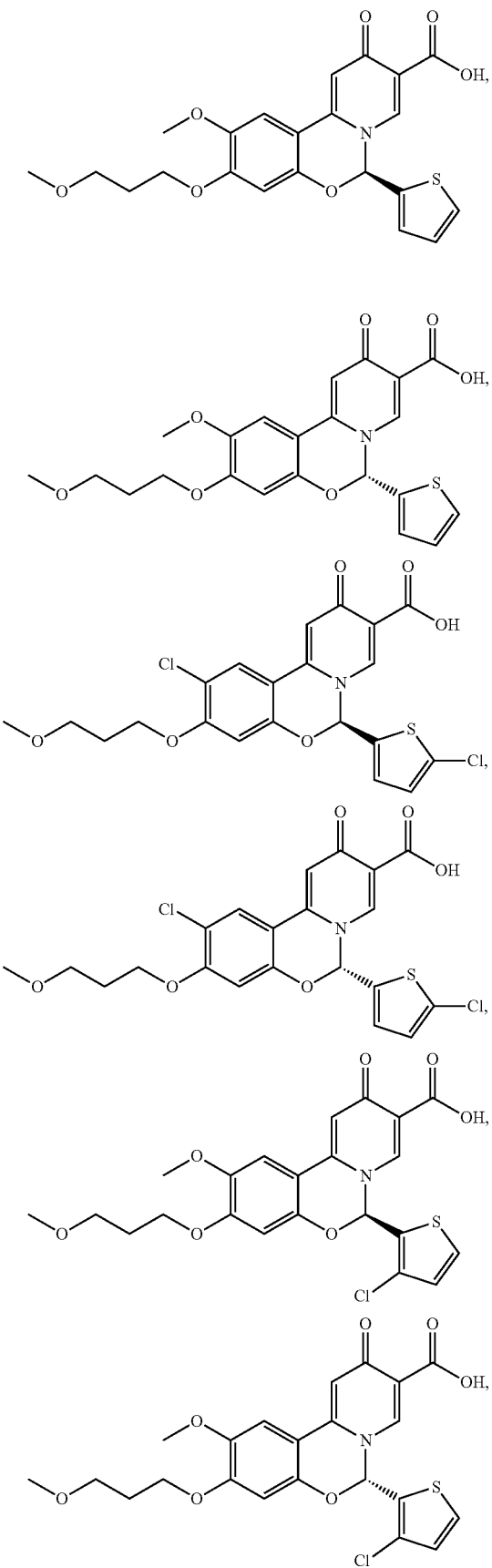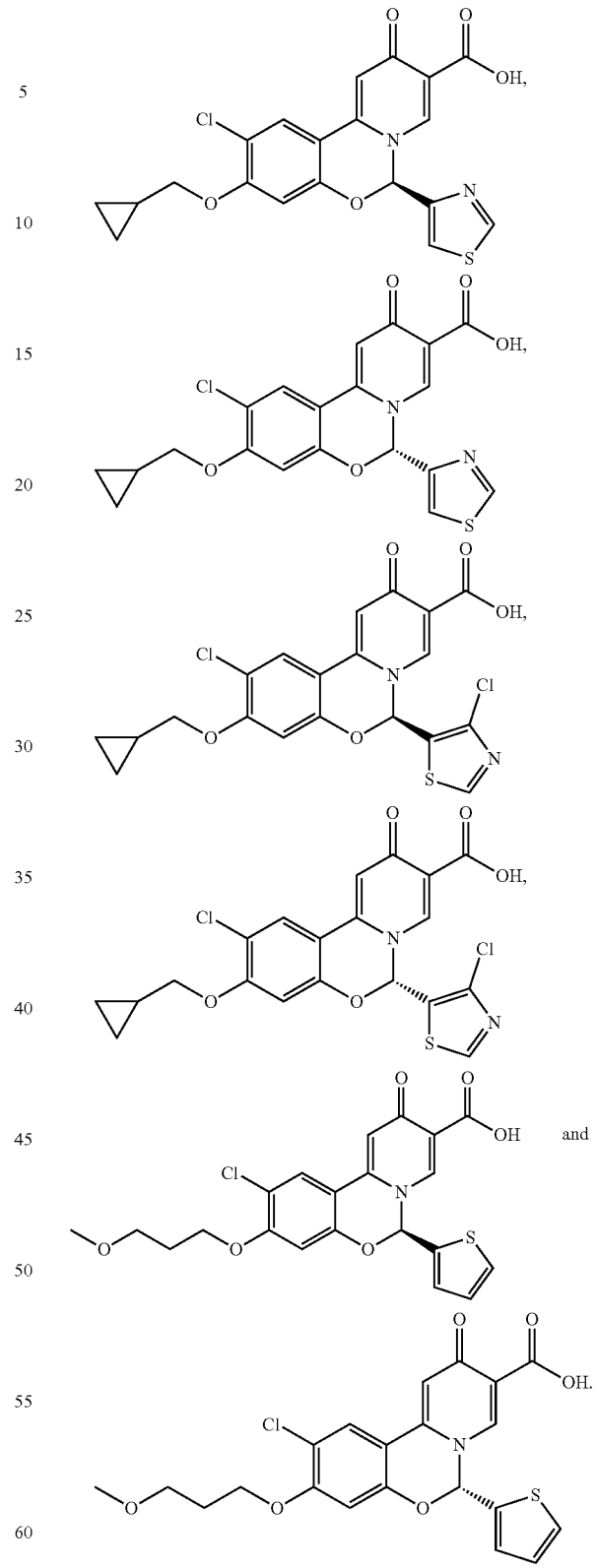
22. A pharmaceutical composition comprising a therapeutically effective amount of the compound or the pharmaceutically acceptable salt thereof as defined in claim 1 and a pharmaceutically acceptable carrier.

23. A method of treating hepatitis B comprising administering to a patient in need thereof a pharmaceutical composition comprising a compound of Formula (I) as in claim 1.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Pre-primer

<400> SEQUENCE: 1
gtgtctgcgg cgttttatca                                              20

<210> SEQ ID NO 2
<211> LENGTH: 21
<212> TYPE: DNA
<213> ORGANISM: Artificial Sequence
<220> FEATURE:
<223> OTHER INFORMATION: Post-primer

<400> SEQUENCE: 2
gacaaacggg caacatacct t                                            21

<210> SEQ ID NO 3
<211> LENGTH: 28
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: FAM modification
<220> FEATURE:
<221> NAME/KEY: misc_feature
<222> LOCATION: (28)..(28)
<223> OTHER INFORMATION: TAMRA modification

<400> SEQUENCE: 3
cctctkcatc ctgctgctat gcctcatc                                     28
```